US007678379B2

(12) United States Patent
Maeurer

(10) Patent No.: US 7,678,379 B2
(45) Date of Patent: Mar. 16, 2010

(54) MYCOBACTERIUM TUBERCULOSIS EPITOPES AND METHODS OF USE THEREOF

(75) Inventor: Markus Joseph Maeurer, Stockholm (SE)

(73) Assignee: Beckman Coulter, Inc., Fullerton, CA (US)

( * ) Notice: Subject to any disclaimer, the term of this patent is extended or adjusted under 35 U.S.C. 154(b) by 572 days.

(21) Appl. No.: 11/156,365

(22) Filed: Jun. 17, 2005

(65) Prior Publication Data

US 2006/0040332 A1 Feb. 23, 2006

Related U.S. Application Data

(60) Provisional application No. 60/580,559, filed on Jun. 17, 2004, provisional application No. 60/622,505, filed on Oct. 27, 2004.

(51) Int. Cl.
*A61K 39/385* (2006.01)
*A61K 39/02* (2006.01)
*A61K 39/04* (2006.01)
*C08H 1/00* (2006.01)
*A61K 38/00* (2006.01)

(52) U.S. Cl. .............................. 424/197.11; 424/193.1; 424/190.1; 424/234.1; 424/248.1; 530/403; 530/802; 530/806; 530/825; 514/2

(58) Field of Classification Search ................ 530/300, 530/350, 825; 514/2; 424/234.1, 190.1, 424/248.1
See application file for complete search history.

(56) References Cited

U.S. PATENT DOCUMENTS

| 4,017,597 | A | 4/1977 | Reynolds | 435/7.92 |
|---|---|---|---|---|
| 4,048,298 | A | 9/1977 | Niswender | 436/500 |
| 4,120,945 | A | 10/1978 | Gutcho et al. | 436/531 |
| 4,208,479 | A | 6/1980 | Zuk et al. | 435/7.9 |
| 4,228,237 | A | 10/1980 | Hevey et al. | 435/5 |
| 4,478,946 | A | 10/1984 | Van der Merwe et al. | 435/7.92 |
| 4,912,030 | A | 3/1990 | Weiss et al. | 435/5 |
| 5,187,065 | A | 2/1993 | Schutzer | 435/7.32 |
| 5,514,557 | A | 5/1996 | Moghaddam | 435/7.24 |
| 5,534,416 | A | 7/1996 | Millard et al. | 436/34 |
| 5,583,031 | A | 12/1996 | Stern | 435/69.1 |
| 5,599,720 | A | 2/1997 | Ekins | 436/501 |
| 5,635,363 | A | 6/1997 | Altman et al. | 435/7.24 |
| 5,734,023 | A | 3/1998 | Nag et al. | 530/403 |
| 5,759,774 | A | 6/1998 | Hackett et al. | 435/2 |
| 5,919,639 | A | 7/1999 | Humphreys et al. | 435/7.24 |
| 5,956,532 | A | 9/1999 | Arita | 396/72 |
| 6,037,135 | A | 3/2000 | Kubo et al. | 435/7.24 |
| 6,046,013 | A | 4/2000 | Tidey et al. | 435/7.21 |
| 6,225,042 | B1 | 5/2001 | Cai et al. | 435/2 |
| 6,270,772 | B1 | 8/2001 | Burrows et al. | 424/193.1 |
| 6,355,479 | B1 | 3/2002 | Webb et al. | 435/325 |
| 6,413,517 | B1 | 7/2002 | Sette et al. | 424/185.1 |
| 6,419,931 | B1 | 7/2002 | Vitiello et al. | 424/201.1 |
| 6,485,913 | B1 | 11/2002 | Becker et al. | 506/13 |
| 6,727,093 | B2 | 4/2004 | Diamond | 435/325 |
| 2002/0006903 | A1 | 1/2002 | Schneck et al. | |
| 2002/0106708 | A1 | 8/2002 | Thomas et al. | |
| 2002/0146746 | A1 | 10/2002 | Nixon et al. | |
| 2003/0044389 | A1 | 3/2003 | Brown et al. | |
| 2003/0044415 | A1 | 3/2003 | Savage | |
| 2003/0124513 | A1 | 7/2003 | McSwiggen | |
| 2003/0166057 | A1 | 9/2003 | Hildebrand et al. | |
| 2003/0191286 | A1 | 10/2003 | Hildebrand et al. | |
| 2004/0072262 | A1 | 4/2004 | Montero-Julian et al. | |
| 2004/0137537 | A1 | 7/2004 | Montero-Julian et al. | |
| 2004/0253632 | A1 | 12/2004 | Rhode et al. | |
| 2005/0059107 | A1 | 3/2005 | Maillere et al. | |
| 2005/0095655 | A1 | 5/2005 | Montero-Julian et al. | |
| 2005/0287611 | A1 | 12/2005 | Nugent et al. | |

FOREIGN PATENT DOCUMENTS

| DE | 195 25 784 | 1/1997 |
|---|---|---|
| EP | 0 958 834 | 11/1999 |
| EP | 1 138 766 | 10/2001 |
| WO | WO 92/07952 | 5/1992 |
| WO | WO 94/11738 | 5/1994 |
| WO | WO 95/04817 | 2/1995 |
| WO | WO 97/00067 | 1/1997 |

(Continued)

OTHER PUBLICATIONS

Sorensen et al. Infect. Immun. 63: 1710-1717, 1995.*
Tully et al. Tully et al. J. Immunol. 174: 2174-2184, Feb. 15, 2005.*
Bodinier, M., et al., "Efficient detection and immunomagnetic sorting of specific T cells using multimers of MHC class I and peptide with reduced CD8 binding," *Nat. Med.* 6:707-710, Nature Publishing Company (2000).
Burgess, W.H., et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.* 111:2129-2138, Rockefeller University Press (1990).

(Continued)

*Primary Examiner*—S. Devi
(74) *Attorney, Agent, or Firm*—Holly O. Soehnge; Sterne, Kessler, Goldstein & Fox PLLC

(57) ABSTRACT

The invention provides novel Class I HLA-A2 and Class II HLA-DR4-restricted epitopes and methods for their use in detecting T-cells in peripheral blood specific for infection or latency of mycobacterial infection, including *M. tuberculosis* and *M. leprae* as others. For example, methods for diagnosing the presence of infection or exposure by *M. tuberculosis* utilize multimers of HLA monomers or modified monomers having a bound HLA-binding peptide to perform high throughput screening of patient PBLs. The methods can be used for monitoring the success of anti mycobacterial treatment in patients and to screen vaccines and drugs for effectiveness in treating or preventing exposure, infection and latency of mycobacteria in humans.

7 Claims, 30 Drawing Sheets

FOREIGN PATENT DOCUMENTS

Figure 1A:
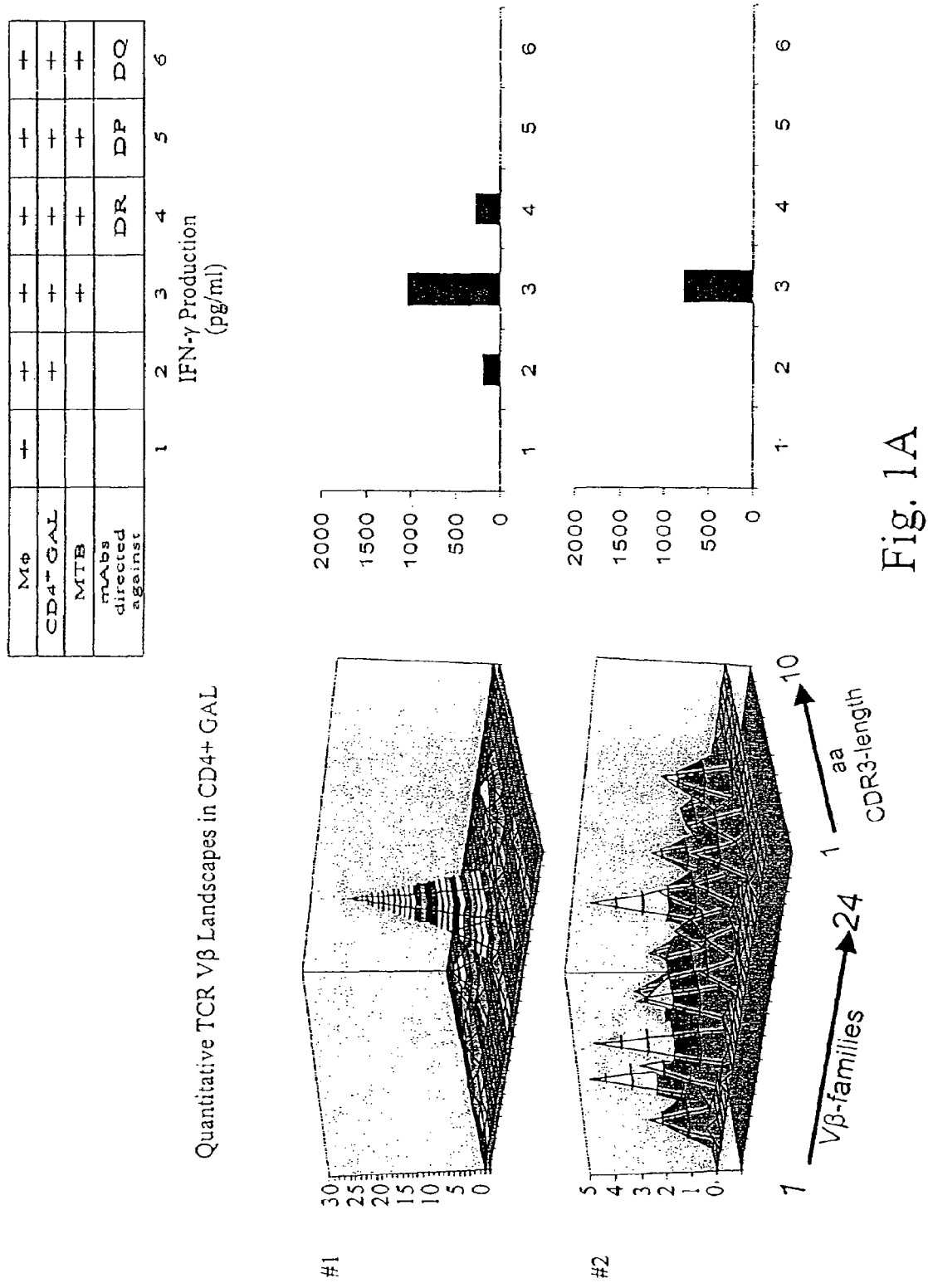

| WO | WO 97/09429 | * | 3/1997 |
|---|---|---|---|
| WO | WO 98/23960 | | 6/1998 |
| WO | WO 99/28748 A2 | | 6/1999 |
| WO | WO 99/50637 A2 | | 10/1999 |
| WO | WO 00/15665 | | 3/2000 |
| WO | WO 00/25813 A1 | | 5/2000 |
| WO | WO 01/90747 | | 11/2001 |
| WO | WO 03/040299 | | 5/2003 |
| WO | WO 2004/094458 | | 11/2004 |

OTHER PUBLICATIONS

Buus, S., et al., "The relation between major histocompatibility complex (MHC) restriction and the capacity of Ia to bind immunogenic peptides," *Science* 235:1353-1358, American Association for the Advancement of Science (1987).

Buus, S., "Description and prediction of peptide-MHC binding: the 'human MHC project'," *Curr. Opin. Immunol.* 11:209-213, Current Biology (1999).

Carbone, F.R., and Bevan, M.J., "Chapter 18: Major Histocompatibility Complex Control of T Cell Recognition," in *Fundamental Immunology 2nd Ed.*, Paul, W.E., ed., Raven Press Publishing, New York, NY, pp. 541-567 (1989).

Cason, J., et al., "Analysis of human lymphocyte transformation responses to graded doses of T cell mitogens by curve fitting," *J. Immunol. Methods* 102:109-117, North-Holland Publishing Co. (1987).

Celis, E., et al., "Induction of anti-tumor cytotoxic T lymphocytes in normal humans using primary cultures and synthetic peptide epitopes," *Proc. Natl. Acad. Sci. U.S.A.* 91:2105-2109, National Academy of Sciences (1994).

Chersi, A., et al., "Polystyrene beads coated with antibodies directed to HLA class I intracytoplasmic domain: the use in quantitative measurement of peptide-HLA class I binding by flow cytometry," *Hum. Immunol.* 61:1298-1306, Elsevier/North-Holland (2000).

Constantin, C.M., et al., "Major histocompatibility complex (MHC) tetramer technology: an evaluation," *Biol. Res. Nurs.* 4:115-127, Sage Publications, Inc. (2002).

Dornmair, K., et al., "Structural intermediates in the reactions of antigenic peptides with MHC molecules," *Cold Spring Harb. Symp. Quant. Biol.* 54:409-416, Cold Spring Harbor Laboratory Press (1989).

Eichmüller, S., et al., "A new method for double immunolabelling with primary antibodies from identical species," *J. Immunol. Methods* 190:255-265, North-Holland Publishing Co. (1996).

Geluk, A., et al., "Identification of major epitopes of *Mycobacterium tuberculosis* AG85B that are recognized by HLA-A*0201-restricted CD8+ T cells in HLA-transgenic mice and humans," *J. Immunol.* 165:6463-6471, American Association of Immunologists (2000).

Gerritsma, J.S.J, et al., "The Constant Domain of IgG Is a Possible Target Antigen for Immunotherapy of B Cell Malignancies in HLA-A1 Mismatch Transplantation," *Blood* 98:404a-405a, The American Society of Hematology (2001).

Godkin, A.J., et al., "Naturally processed HLA class II peptides reveal highly conserved immunogenic flanking region sequence preferences that reflect antigen processing rather than peptide-MHC interactions," *J. Immunol.* 166:6720-6727, American Association of Immunologists (2001).

Gorga, J.C., et al., "Purification and characterization of class II histocompatibility antigens from a homozygous human B cell line," *J. Biol. Chem.* 262:16087-16094, American Society for Biochemistry and Molecular Biology (1987).

Hansen, T.H., and Sachs, D.H., "Chapter 16: The Major Histocompatibility Complex," in *Fundamental Immunology 2nd Ed.*, Paul, W.E., ed., Raven Press Publishing, New York, NY, pp. 445-488 (1989).

Henderson, R.A., et al., "Direct identification of an endogenous peptide recognized by multiple HLA-A2.1-specific cytotoxic T cells," *Proc. Natl. Acad. Sci. U.S.A.* 90:10275-10279, National Academy of Sciences (1993).

Hengel, H., et al., "Frequency of herpes simplex virus-specific murine cytotoxic T lymphocyte precursors in mitogen- and antigen-driven primary in vitro T cell responses," *J. Immunol.* 139:4196-4202, American Association of Immunologists (1987).

Herr, W., et al., "Detection and quantification of blood-derived CD8+ T lymphocytes secreting tumor necrosis factor alpha in response to HLA-A2.1-binding melanoma and viral peptide antigens," *J. Immunol. Methods* 191:131-142, North-Holland Publishing Co. (1996).

Herr, W., et al., "The use of computer-assisted video image analysis for the quantification of CD8+ T lymphocytes producing tumor necrosis factor alpha spots in response to peptide antigens," *J. Immunol. Methods* 203:141-152 North-Holland Publishing Co. (1997).

Hickling, J.K., et al., "Varicella-zoster virus-specific cytotoxic T lymphocytes (Tc): detection and frequency analysis of HLA class I-restricted Tc in human peripheral blood," *J. Virol.* 61:3463-3469, American Society for Microbiology (1987).

Hörig, H., et al., "An in vitro study of the dynamic features of the major histocompatibility complex class I complex relevant to its role as a versatile peptide-receptive molecule," *Proc. Natl. Acad. Sci. U.S.A.* 94:13826-13831, National Academy of Sciences (1997).

Hugues, S., et al., "Generation and use of alternative multimers of peptide/MHC complexes," *J. Immunol. Methods* 268:83-92, North-Holland Publishing Co. (2002).

Hunkapiller, M.W., et al., "Isolation of microgram quantities of proteins from polyacrylamide gels for amino acid sequence analysis," *Methods Enzymol.* 91:227-236, Academic Press (1983).

Hunt, D.F., et al., "Characterization of peptides bound to the class I MHC molecule HLA-A2.1 by mass spectrometry," *Science* 255:1261-1263, American Association for the Advancement of Science (1992).

Jäger, E., et al., "Impact of antigen presentation on TCR modulation and cytokine release: implications for detection and sorting of antigen-specific CD8+ T cells using HLA-A2 wild-type or HLA-A2 mutant tetrameric complexes," *J. Immunol.* 168:2766-2772, American Association of Immunologists (2002).

Jensen, P.E., et al., "A europium fluoroimmunoassay for measuring peptide binding to MHC class I molecules," *J. Immunol. Methods* 215:71-80, North-Holland Publishing Co. (1998).

Kadival, G.V., et al., "Characterization of serologic and cell-mediated reactivity of a 38-kDa antigen isolated from *Mycobacterium tuberculosis*," *J. Immunol.* 139:2447-2451, American Association of Immunologists (1987).

Kawakami, Y., et al., "Cloning of the gene coding for a shared human melanoma antigen recognized by autologous T cells infiltrating into tumor," *Proc. Natl. Acad. Sci. U.S.A.* 91:3515-3519, National Academy of Sciences (1994).

Kawakami, Y., et al., "Identification of the immunodominant peptides of the MART-1 human melanoma antigen recognized by the majority of HLA-A2-restricted tumor infiltrating lymphocytes," *J. Exp. Med.* 180:347-352, Rockefeller University Press (1994).

Kuhns, J.J., et al., "Poor binding of a HER-2/neu epitope (GP2) to HLA-A2.1 is due to a lack of interactions with the center of the peptide," *J. Biol. Chem.* 274:36422-36427, American Society for Biochemistry and Molecular Biology (1999).

Lazar, E., et al., "Transforming growth factor alpha: mutation of aspartic acid 47 and leucine 48 results in different biological activities," *Mol. Cell. Biol.* 8:1247-1252, American Society for Microbiology (1988).

Maeurer, M.J., et al., "Improved detection of melanoma antigen-specific T cells expressing low or high levels of CD8 by HLA-A2 tetramers presenting a Melan-A/Mart-1 peptide analogue," *Int. J. Cancer* 97:64-71, Wiley-Liss (2002).

Male, D., "Chapter 2: Antibodies and Antigens," in *Immunology: An Illustrated Outline*, Bennet, D., ed., Gower Medical Publishing, London, England, p. 29 (1986).

Marin, M., et al., "Cloning and expression of a single-chain antibody fragment specific for a monomorphic determinant of class I molecules of the human major histocompatibility complex," *Hybridoma* 14:443-451, Mary Ann Liebert (1995).

Marx, J.L., "Histocompatibility restriction explained," *Science* 235:843-844, American Association for the Advancement of Science (1987).

Men, Y., et al., "Assessment of immunogenicity of human Melan-A peptide analogues in HLA-A*0201/Kb transgenic mice," *J. Immunol. 162*:3566-3573, American Association of Immunologists (1999).

Merriam-Webster Online Dictionary, "Reconstitute—Definition from the Merriam-Webster Online Dictionary," http://www.merriam-webster.com/dictionary/reconstitute, 1 page (accessed 2008).

Miller, J.E.W., et al., "Rapid determination of class I peptide binding motifs using codon-based random peptide phage display libraries," *J. Cell. Biochem. 18D*:292, Liss (1994).

Passmore, D., et al., "Preparative-scale purification and characterization of MHC class II monomers," *J. Immunol. Methods 155*:193-200, North-Holland Publishing Co. (1994).

Plytycz, B., and Seljelid, R., "MHC molecules and lymphocytes: evolutionary perspective," *Arch. Immunol. Ther. Exp. (Warsz) 46*:137-142, Birkhaüser (1998).

Robinson, M.A., and Kindt, T.J., "Chapter 17:Major Histocompatiblity Complex Antigens and Genes," in *Fundamental Immunology 2nd Ed.*, Paul, W.E., ed., Raven Press Publishing, New York, NY, pp. 489-540 (1989).

Roitt, I.M., et al., eds., "Chapter 5: Antibody Structure and Function," in *Immunology*, Gower Medical Publishing, London, England, p. 5.7, (1986).

Ruppert, J., et al., "Prominent role of secondary anchor residues in peptide binding to HLA-A2.1 molecules," *Cell 74*:929-937, Cell Press (1993).

Sadegh-Nasseri, S., and McConnell, H.M., "A kinetic intermediate in the reaction of an antigenic peptide and I-Ek," *Nature 337*:274-276, Nature Publishing Group (1989).

Samelson, L.E., et al., "T cell antigen receptor phosphorylation induced by an anti-receptor antibody," *J. Immunol. 139*:2708-2714, American Association of Immunologists (1987).

Sette, A., et al., "Structural characteristics of an antigen required for its interaction with Ia and recognition by T cells," *Nature 328*:395-399, Nature Publishing Group (1987).

Smith, J.D., et al., "Extensive peptide ligand exchange by surface class I major histocompatibility complex molecules independent of exogenous beta 2- microglobulin," *Proc. Natl. Acad. Sci. U.S.A. 89*:7767-7771, National Academy of Sciences (1992).

Springfrog, "Temperature Converter," accessed online at http://springfrog.com/converter/temperature.htm, 2 pages (accessed 2008).

Sugita, M., et al., "Assembly and retention of CD1b heavy chains in the endoplasmic reticulum," *J. Immunol. 159*:2358-2365, American Association of Immunologists (1997).

Sylvester-Hvid, C., et al., "Establishment of a quantitative ELISA capable of determining peptide—MHC class I interaction," *Tissue Antigens 59*:251-258, International Booksellers Publishers (2002).

Tao, M.H., and Morrison, S.L., et al., "Studies of aglycosylated chimeric mouse-human IgG. Role of carbohydrate in the structure and effector functions mediated by the human IgG constant region," *J. Immunol. 143*:2595-2601, American Association of Immunologists (1989).

Thorley-Lawson, D.A., and Israelsohn, E.S., "Generation of specific cytotoxic T cells with a fragment of the Epstein-Barr virus-encoded p63/latent membrane protein," *Proc. Natl. Acad. Sci. U.S.A. 84*:5384-5388, National Academy of Sciences (1987).

Tissot, A.C., et al., "Characterizing the functionality of recombinant T-cell receptors in vitro: a pMHC tetramer based approach," *J. Immunol. Methods 236*:147-165, North-Holland Publishing Co. (2000).

Tompkins, S.M., et al., "A europium fluoroimmunoassay for measuring binding of antigen to class II MHC glycoproteins," *J. Immunol. Methods 163*:209-216, North-Holland Publishing Co. (1993).

Tsien, R.Y., et al., "T-cell mitogens cause early changes in cytoplasmic free $Ca^{2+}$ and membrane potential in lymphocytes," *Nature 295*:68-71, Nature Publishing Group (1982).

Tsomides, T.J., et al., "An optimal viral peptide recognized by $CD8^+$ T cells binds very tightly to the restricting class I major histocompatibility complex protein on intact cells but not to the purified class I protein," *Proc. Natl. Acad. Sci. U.S.A. 88*:11276-11280, National Academy of Sciences (1991).

Turner, M.J., et al., "Purification of papain-solubilized histocompatibility antigens from a cultured human lymphoblastoid line, RPMI 4265," *J. Biol. Chem. 250*:4512-4519, American Society for Biochemistry and Molecular Biology (1975).

Valmori, D., et al., "Diversity of the fine specificity displayed by HLA-A*0201-restricted CTL specific for the immunodominant Melan-A/MART-1 antigenic peptide," *J. Immunol. 161*:6956-6962, American Association of Immunologists (1998).

Van der Burg, S.H., et al., "An HLA class I peptide-binding assay based on competition for binding to class I molecules on intact human B cells. Identification of conserved HIV-1 polymerase peptides binding to HLA-A*0301," *Hum. Immunol. 44*:189-198, Elsevier/North-Holland (1995).

Van der Burg, S.H., et al., "Immunogenicity of peptides bound to MHC class I molecules depends on the MHC-peptide complex stability," *J. Immunol. 156*:3308-3314, American Association of Immunologists (1996).

Wells, J.A., "Additivity of mutational effects in proteins," *Biochemistry 29*:8509-8517, American Chemical Society (1990).

Flad, T., et al., "Direct identification of major histocompatibility complex class I-bound tumor-associated peptide antigens of a renal carcinoma cell line by a novel mass spectrometric method," *Cancer Res. 58*:5803-5811, American Association for Cancer Research (1998).

Garboczi, D.N., et al., "HLA-A2-peptide complexes: refolding and crystallization of molecules expressed in *Escherichia coli* and complexed with single antigenic peptides," *Proc. Natl. Acad. Sci. USA 89*:3429-3433, National Academy of Sciences (1992).

Kozono, H., et al., "Production of soluble MHC class II proteins with covalently bound single peptides," *Nature 369*:151-154, Nature Publishing Group (1994).

Du Pasquier, R.A., et al., "Low Frequency of Cytotoxic T Lymphocytes against the Novel HLA-A*0201-Restricted JC Virus Epitope $VP1_{p36}$ in Patients with Proven or Possible Progressive Multifocal Leukoencephalopathy", *J. Virol. 77*:11918-11926, American Society for Microbiology (Nov. 2003).

Hermans, I.F., et al., "The VITAL assay: a versatile fluorometric technique for assessing CTL- and NKT-mediated cytotoxicity against multiple targets in vitro and in vivo", *J. Immunol. Methods 285*:25-40, North-Holland Publishing Co. (Feb. 2004).

Mallet-Designe, V.I., et al., "Detection of Low-Avidity $CD4^+$ T Cells Using Recombinant Artificial APC: Following the Antiovalbumin Immune Response", *J. Immunol. 170*:123-131, American Association of Immunologists (Jan. 2003).

Robert, B., et al., "Antibody-conjugated MHC class I tetramers can target tumor cells for specific lysis by T lymphocytes", *Eur. J. Immunol. 30*:3165-3170, VCH Verlagsgesellschaft (2000).

European Search Report for European Application No. EP 05 74 5499, completed on Apr. 24, 2008, European Patent Office, The Hague, Netherlands.

Vincenti, D., et al, "Identification of Early Secretory Antigen Target-6 Epitopes for the Immunodiagnosis of Active Tuberculosis", Molecular Medicine, vol. 9, No. 3/4, pp. 105-111, Mar./Apr. 2003.

* cited by examiner

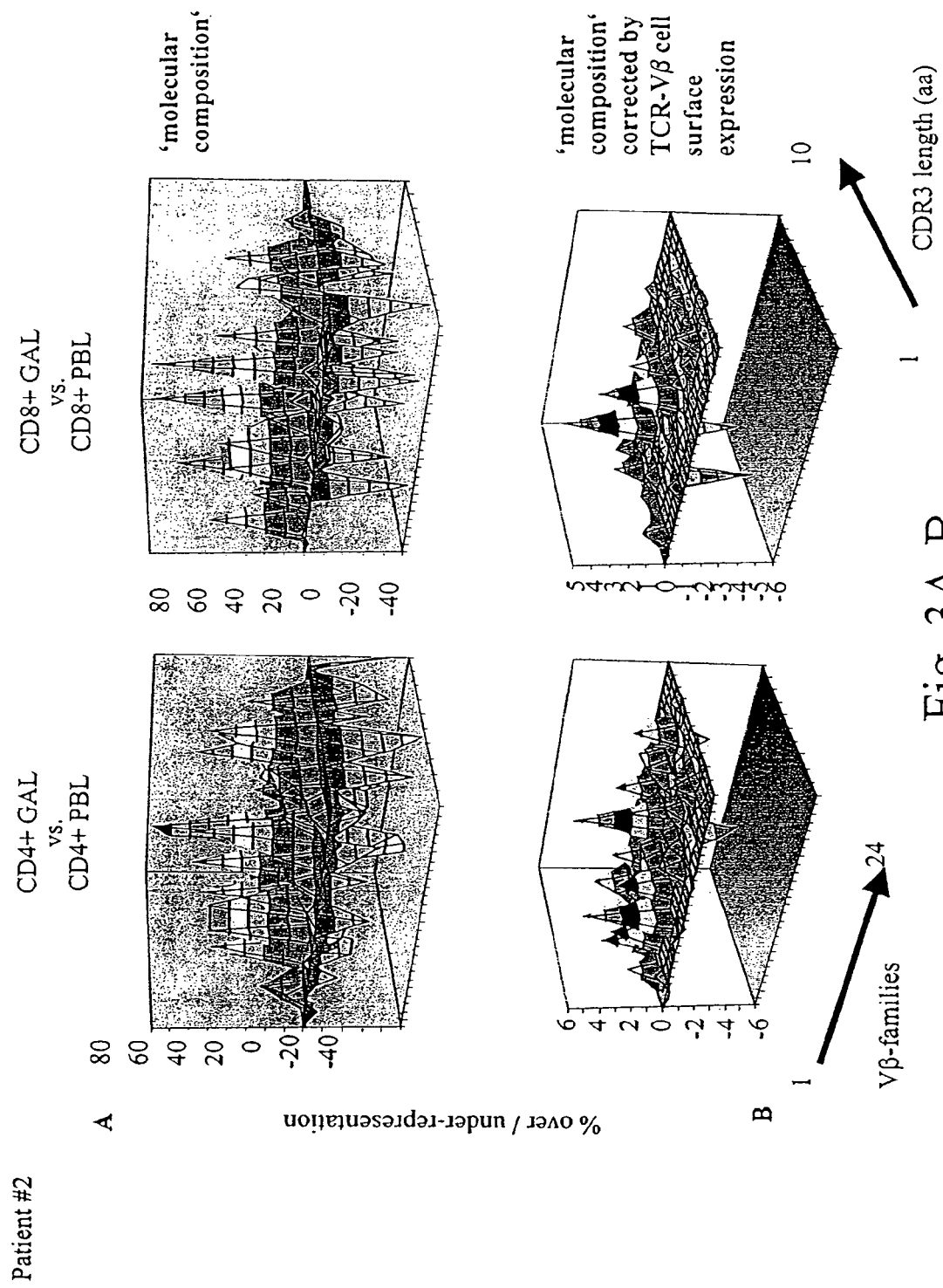
Fig. 3A-B

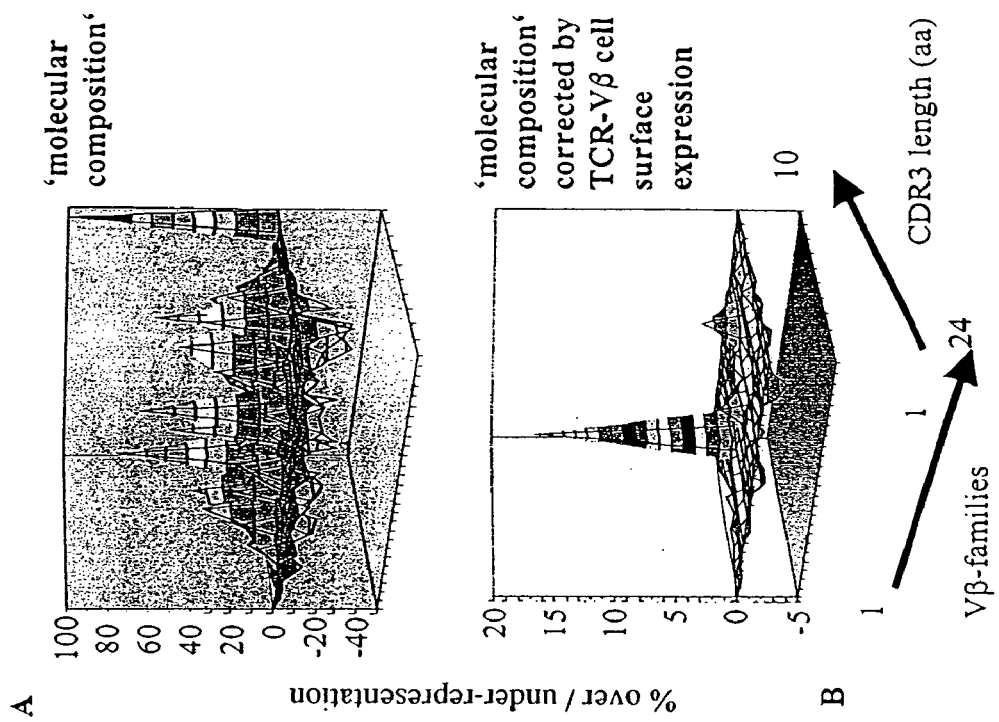
Fig. 4A-B

Patient #1
IFN-γ (pg/ml)
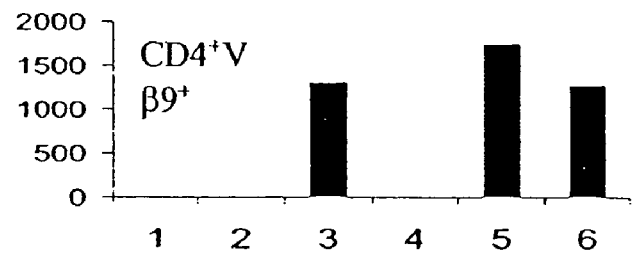
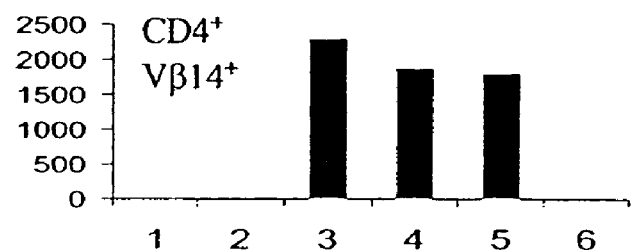
| | 1 | 2 | 3 | 4 | 5 | 6 |
|---|---|---|---|---|---|---|
| Mφ | + | + | + | + | + | + |
| CD4+ GAL | | + | + | + | + | + |
| MTB | | | + | + | + | + |
| mAbs directed against | | | | DR | DP | DQ |
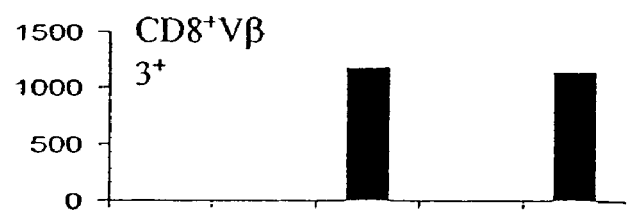
| | 1 | 2 | 3 | 4 | 5 |
|---|---|---|---|---|---|
| Mφ | + | + | + | + | + |
| CD8+ GAL | | + | + | + | + |
| MTB | | | + | + | + |
| mAbs directed against | | | | MHC-I | MHC-II |
Fig. 5A Patient #2
IFN-γ (pg/ml)
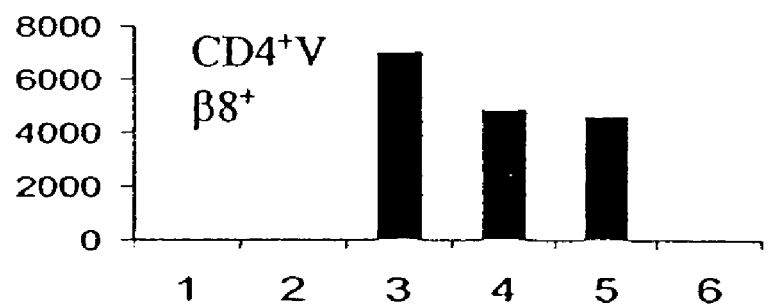
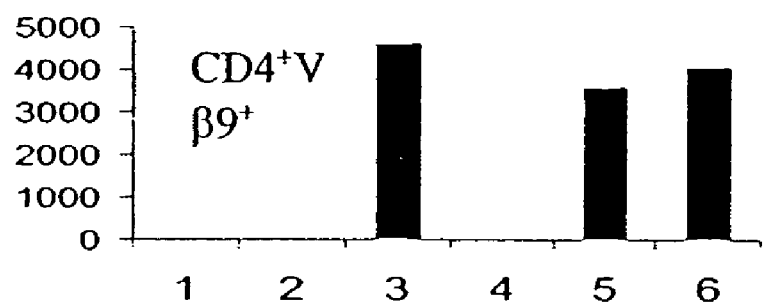
| | 1 | 2 | 3 | 4 | 5 | 6 |
|---|---|---|---|---|---|---|
| Mφ | + | + | + | + | + | + |
| CD4+ GAL | | + | + | + | + | + |
| MTB | | | + | + | + | + |
| mAbs directed against | | | | DR | DP | DQ |
Fig. 5B

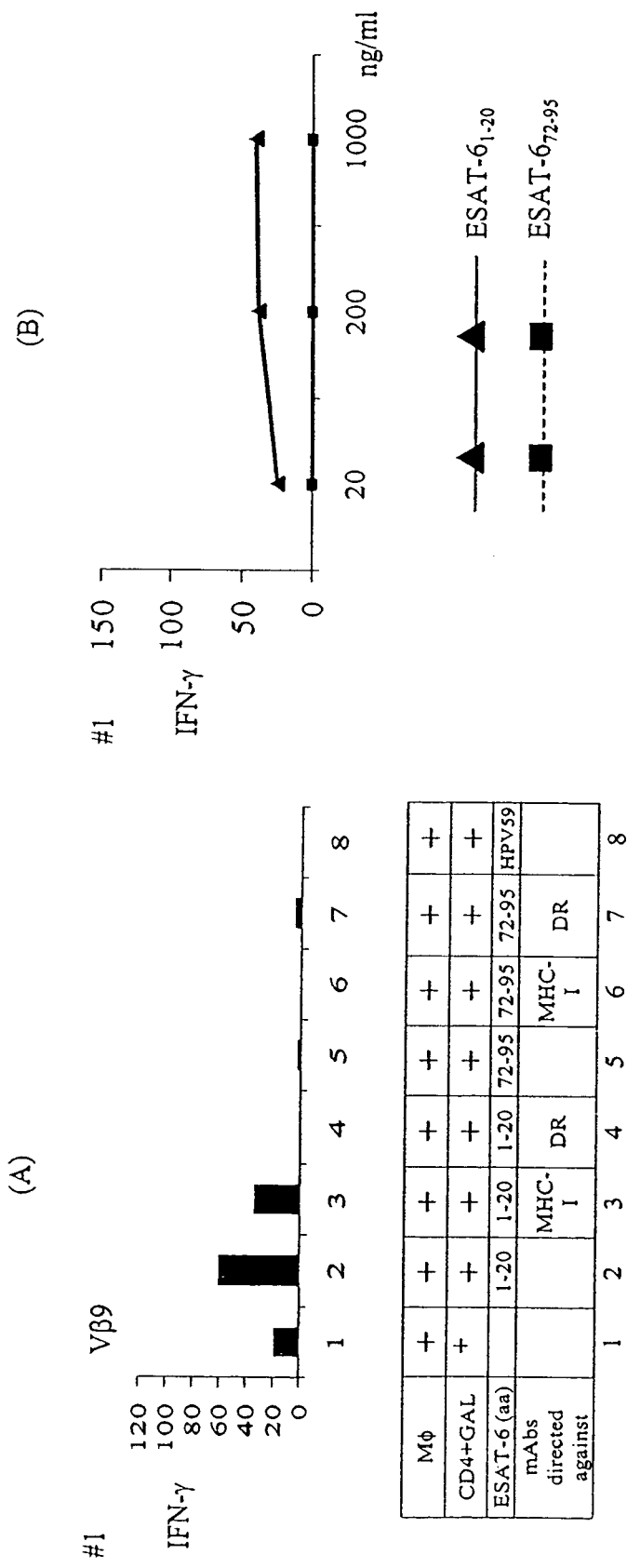
Fig. 6A-B

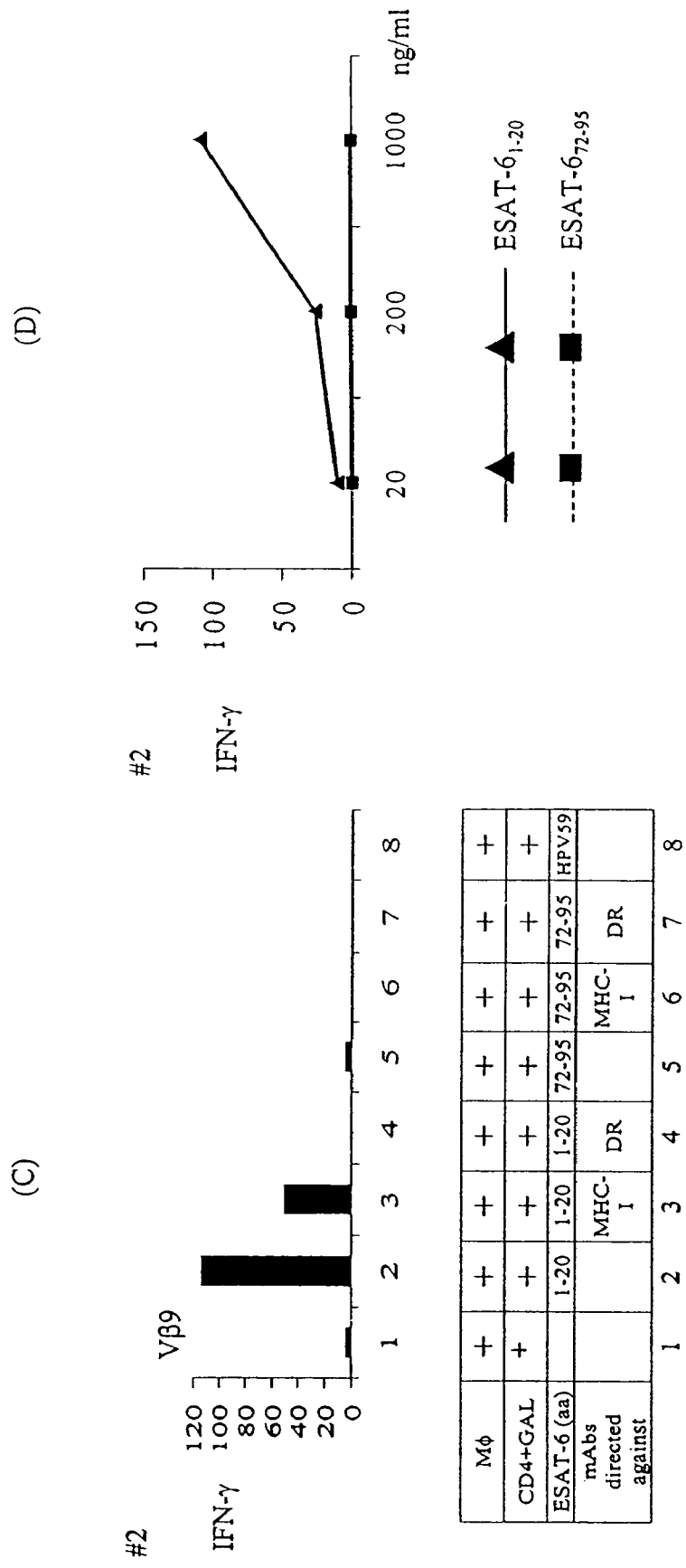
Fig. 6C-D

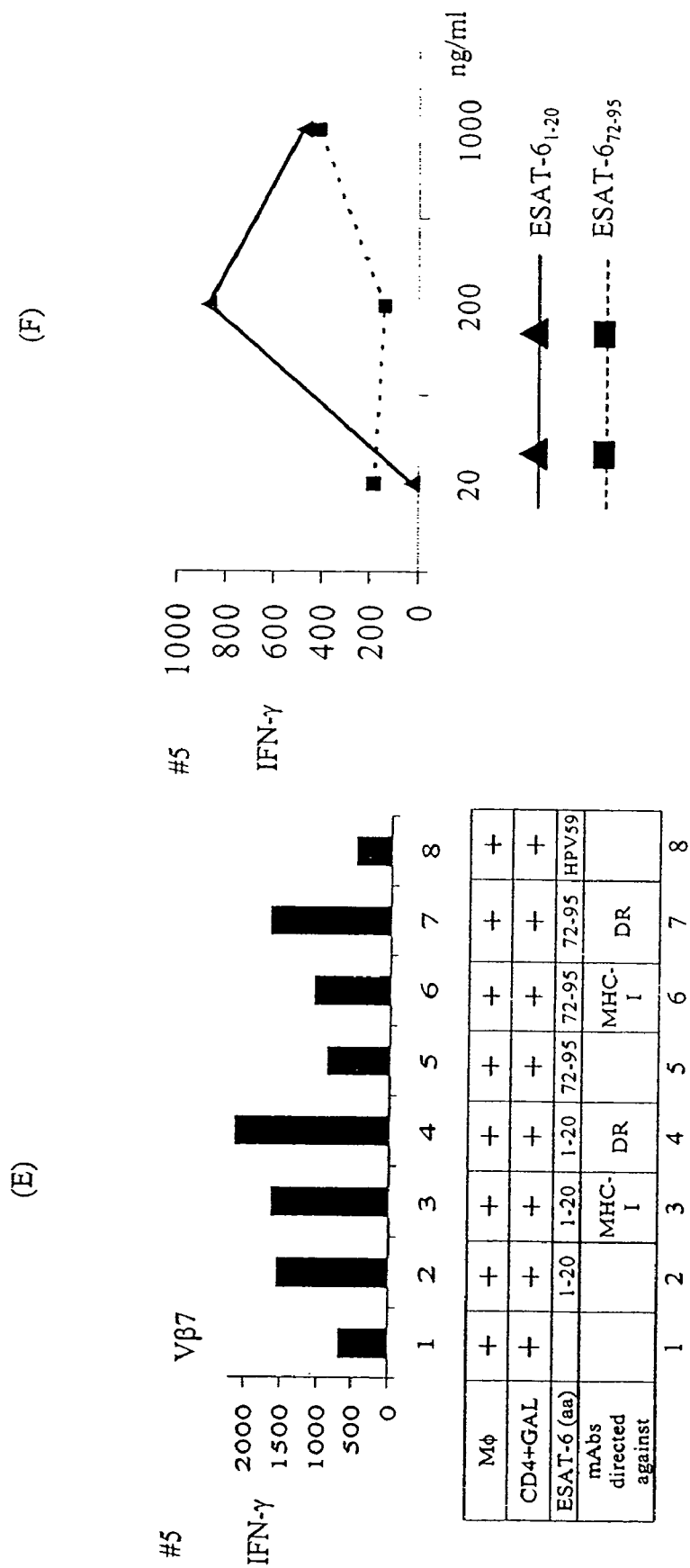
Fig. 6E-F

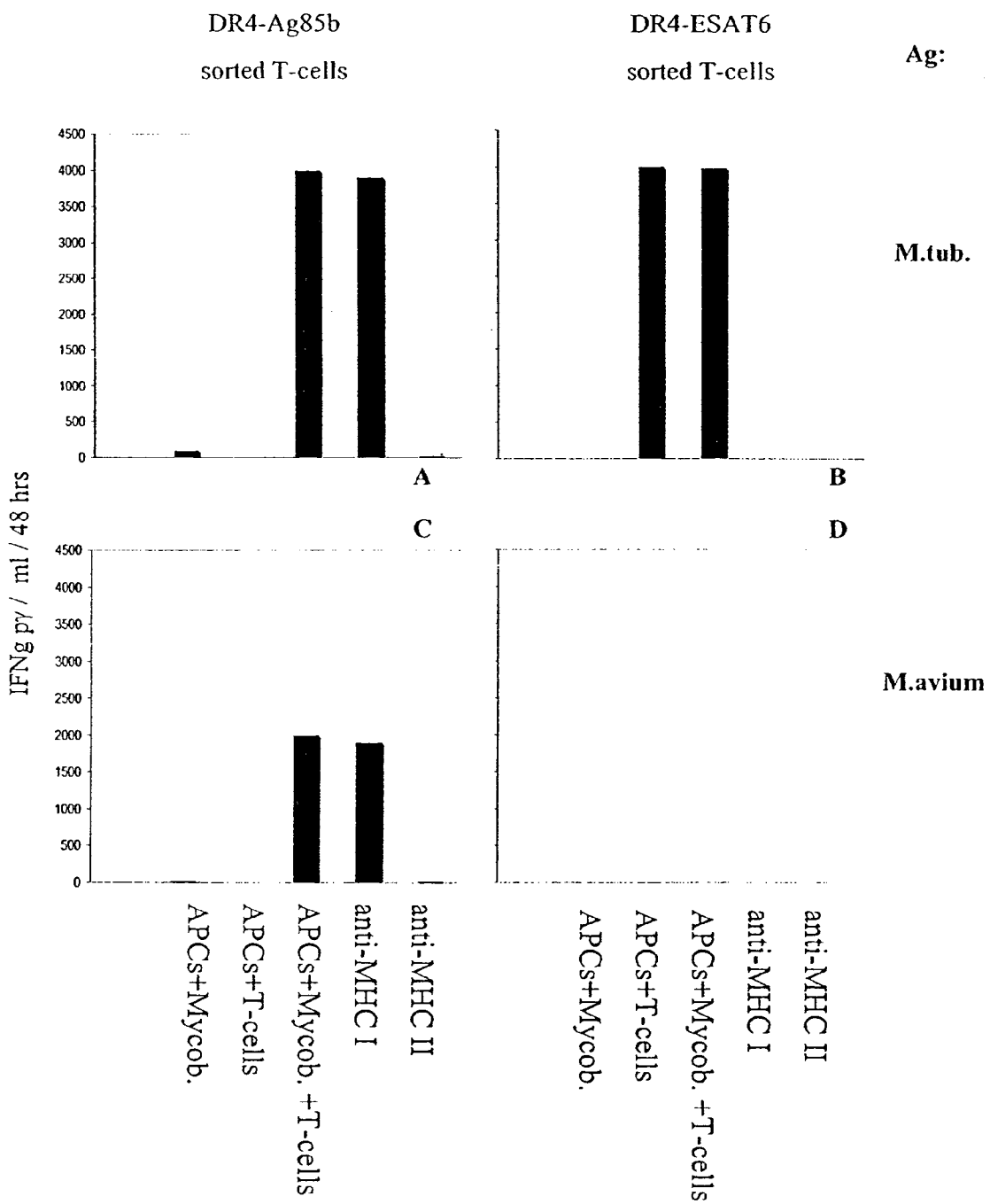
Fig. 10A-D

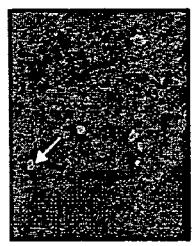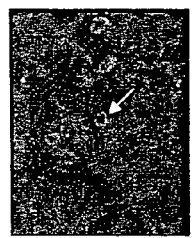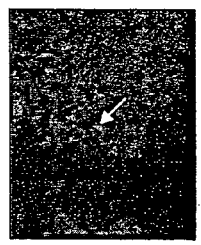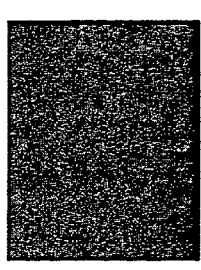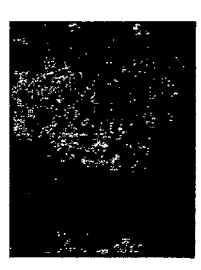
Fig. 14B
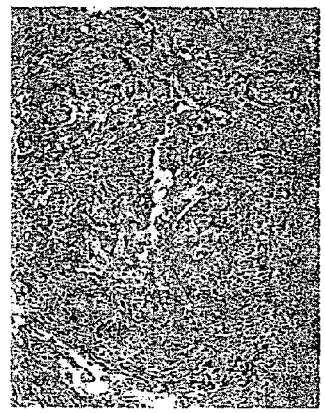
Fig. 14A

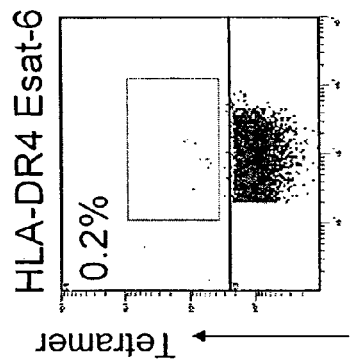
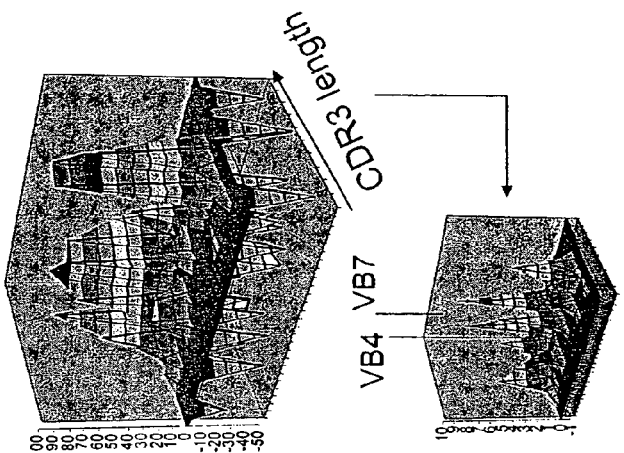
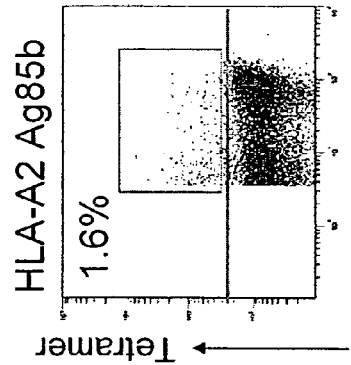
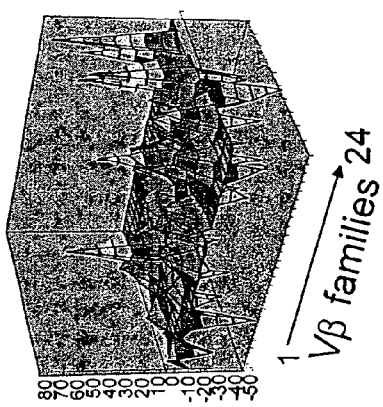
Fig. 15A Flow-guided tetramer analysis
Fig. 15B TCR CDR3 comparative analysis
Fig. 15C TCR CDR3 quantitative analysis

```
                              SEQUENCE LISTING

<160> NUMBER OF SEQ ID NOS: 27

<210> SEQ ID NO 1
<211> LENGTH: 10
<212> TYPE: PRT
<213> ORGANISM: Mycobacterium tuberculosis

<400> SEQUENCE: 1

Val Leu Thr Asp Gly Asn Pro Pro Glu Val
1               5                   10

<210> SEQ ID NO 2
<211> LENGTH: 9
<212> TYPE: PRT
<213> ORGANISM: Mycobacterium tuberculosis

<400> SEQUENCE: 2

Lys Leu Val Ala Asn Asn Thr Arg Leu
1               5

<210> SEQ ID NO 3
<211> LENGTH: 9
<212> TYPE: PRT
<213> ORGANISM: Mycobacterium tuberculosis

<400> SEQUENCE: 3

Leu Leu Asp Glu Gly Lys Gln Ser Leu
1               5

<210> SEQ ID NO 4
<211> LENGTH: 9
<212> TYPE: PRT
<213> ORGANISM: Artificial sequence
<220> FEATURE:
<223> OTHER INFORMATION: CMVpp65 antigen epitope

<400> SEQUENCE: 4

Asn Leu Val Pro Met Val Ala Thr Val
1               5

<210> SEQ ID NO 5
<211> LENGTH: 9
<212> TYPE: PRT
<213> ORGANISM: Artificial sequence
<220> FEATURE:
<223> OTHER INFORMATION: Melanoma associated antigen gp100

<400> SEQUENCE: 5

Tyr Leu Glu Pro Gly Pro Val Thr Val
1               5

<210> SEQ ID NO 6
<211> LENGTH: 15
<212> TYPE: PRT
<213> ORGANISM: Mycobacterium tuberculosis

<400> SEQUENCE: 6

Gln Met Pro Tyr Gln Pro Val Gln Ser Pro Thr Gln Val Glu Ala
```

```
1               5                  10                 15
```

<210> SEQ ID NO 7
<211> LENGTH: 15
<212> TYPE: PRT
<213> ORGANISM: Mycobacterium tuberculosis

<400> SEQUENCE: 7

```
Pro Val Glu Tyr Leu Gln Tyr Pro Ser Pro Ser Met Gly Arg Asp
1               5                   10                  15
```

<210> SEQ ID NO 8
<211> LENGTH: 15
<212> TYPE: PRT
<213> ORGANISM: Mycobacterium tuberculosis

<400> SEQUENCE: 8

```
Phe Ala Gly Ile Glu Ala Ala Ala Ser Ala Ile Gln Gly Asn Val
1               5                   10                  15
```

<210> SEQ ID NO 9
<211> LENGTH: 11
<212> TYPE: PRT
<213> ORGANISM: Homo sapiens

<400> SEQUENCE: 9

```
Pro Ser Pro Asn Gln Thr Ser Leu Tyr Phe Cys
1               5                   10
```

<210> SEQ ID NO 10
<211> LENGTH: 29
<212> TYPE: DNA
<213> ORGANISM: Homo sapiens

<400> SEQUENCE: 10

```
gcagcagttc tcgggccggg gcggtgggt                                          29
```

<210> SEQ ID NO 11
<211> LENGTH: 10
<212> TYPE: PRT
<213> ORGANISM: Homo sapiens

<400> SEQUENCE: 11

```
Ala Ser Ser Ser Arg Ala Gly Ala Val Gly
1               5                   10
```

<210> SEQ ID NO 12
<211> LENGTH: 14
<212> TYPE: PRT
<213> ORGANISM: Homo sapiens

<400> SEQUENCE: 12

```
Glu Gln Phe Phe Gly Pro Gly Thr Arg Leu Thr Val Leu Glu
1               5                   10
```

<210> SEQ ID NO 13
<211> LENGTH: 11
<212> TYPE: PRT
<213> ORGANISM: Homo sapiens

<400> SEQUENCE: 13

```
Ala Ser Thr Asn Gln Thr Ser Met Tyr Leu Cys
1               5                   10
```

```
<210> SEQ ID NO 14
<211> LENGTH: 24
<212> TYPE: DNA
<213> ORGANISM: Homo sapiens

<400> SEQUENCE: 14
gccagcagtt taattcaagg gggc                                              24

<210> SEQ ID NO 15
<211> LENGTH: 8
<212> TYPE: PRT
<213> ORGANISM: Homo sapiens

<400> SEQUENCE: 15

Ala Ser Ser Leu Ile Gln Gly Gly
1               5

<210> SEQ ID NO 16
<211> LENGTH: 9
<212> TYPE: PRT
<213> ORGANISM: Homo sapiens

<400> SEQUENCE: 16

Asn Gln Pro Gln His Phe Gly Asp Gly
1               5

<210> SEQ ID NO 17
<211> LENGTH: 6
<212> TYPE: PRT
<213> ORGANISM: Homo sapiens

<400> SEQUENCE: 17

Ser Ala Leu Tyr Leu Cys
1               5

<210> SEQ ID NO 18
<211> LENGTH: 33
<212> TYPE: DNA
<213> ORGANISM: Homo sapiens

<400> SEQUENCE: 18
gccagcagcc aagatacggc gggggccttc cgg                                    33

<210> SEQ ID NO 19
<211> LENGTH: 11
<212> TYPE: PRT
<213> ORGANISM: Homo sapiens

<400> SEQUENCE: 19

Ala Ser Ser Gln Asp Thr Ala Gly Ala Phe Arg
1               5                   10

<210> SEQ ID NO 20
<211> LENGTH: 11
<212> TYPE: PRT
<213> ORGANISM: Homo sapiens

<400> SEQUENCE: 20

Glu Thr Gln Tyr Phe Gly Pro Gly Thr Arg Leu
1               5                   10

<210> SEQ ID NO 21
<211> LENGTH: 9
<212> TYPE: PRT
<213> ORGANISM: Mycobacterium tuberculosis
```

```
<400> SEQUENCE: 21

Gly Leu Pro Val Glu Tyr Leu Gln Val
1               5

<210> SEQ ID NO 22
<211> LENGTH: 9
<212> TYPE: PRT
<213> ORGANISM: Mycobacterium tuberculosis

<400> SEQUENCE: 22

Lys Leu Ile Ala Asn Asn Thr Arg Val
1               5

<210> SEQ ID NO 23
<211> LENGTH: 10
<212> TYPE: PRT
<213> ORGANISM: Mycobacterium tuberculosis

<400> SEQUENCE: 23

Phe Ile Tyr Ala Gly Ser Leu Ser Ala Leu
1               5                   10

<210> SEQ ID NO 24
<211> LENGTH: 9
<212> TYPE: PRT
<213> ORGANISM: Mycobacterium tuberculosis

<400> SEQUENCE: 24

Ala Ile Gln Gly Asn Val Thr Ser Ile
1               5

<210> SEQ ID NO 25
<211> LENGTH: 8
<212> TYPE: PRT
<213> ORGANISM: Mycobacterium tuberculosis

<400> SEQUENCE: 25

Ala Thr Ala Glu Leu Asn Asn Ala
1               5

<210> SEQ ID NO 26
<211> LENGTH: 20
<212> TYPE: PRT
<213> ORGANISM: Mycobacterium tuberculosis

<400> SEQUENCE: 26

Met Thr Glu Gln Gln Trp Asn Phe Ala Gly Ile Glu Ala Ala Ala Ser
1               5                   10                  15

Ala Ile Gln Gly
            20

<210> SEQ ID NO 27
<211> LENGTH: 24
<212> TYPE: PRT
<213> ORGANISM: Mycobacterium tuberculosis

<400> SEQUENCE: 27

Leu Ala Arg Thr Ile Ser Glu Ala Gly Gln Ala Met Ala Ser Thr Glu
1               5                   10                  15

Gly Asn Val Thr Gly Met Phe Ala
            20
```

MYCOBACTERIUM TUBERCULOSIS EPITOPES AND METHODS OF USE THEREOF

CROSS REFERENCE TO RELATED APPLICATIONS

This application claims the benefit of priority under 35 U.S.C §119(e) of U.S. Ser. No. 60/580,559, filed Jun. 17, 2004, and U.S. Ser. No. 60/622,505, filed Oct. 27, 2004, the entire contents of each of which are incorporated herein by reference.

FIELD OF THE INVENTION

The present invention relates generally to immunology and more specifically to identification of T-cell epitopes and methods of identifying human subjects infected with or exposed to a mycobacteria species.

BACKGROUND OF THE INVENTION

*Mycobacterium tuberculosis* (MTB) infects one-third of the world population and is responsible for 2-3 million deaths each year. Eight million people develop clinical disease each year. A protective vaccine is not yet available and multi-drug resistant MTB-strains pose a threat in developing and industrialized countries. Multiple defense mechanisms are available to contain the intracellular MTB infection to latency, including antigen reactive γδ+ T-cells, CD4+ T-cells which may differentiate into memory T-lymphocytes and CD8+ T-cells instrumental in maintaining anti-MTB control.

Latent MTB infection represents a major threat both for the infected individual and for spreading the infectious agent to other individuals. Weakened cellular immunity associated with age, malnutrition, immunosuppression, or coinfection with HIV leads to loss of MTB containment. Disease containment in TB involves a complex network of immune cells and their ability to mount and maintain effective immune responses. Our knowledge of all engaged immune events involved in maintaining latency of this disease in humans is yet to be complete. The importance of a coordinated cellular immunity to combat this intracellular pathogen is however indisputable. The essential role of MHC class II-restricted CD4+ as well as MHC class I-restricted CD8+ T-cells is well established (recently reviewed in). One of the major weapons of these T-cells is the production of cytokines, e.g. IFN-γ and TNF-α, that can activate macrophages and induce their production of bacteriocidal molecules. Nonclassically restricted CD8+ lymphocytes, CD4⁻CD8⁻ and CD1-restricted T-cells, γδ cells and NK cells have also been reported to recognize mycobacterial lipid antigens presented on CD1 molecules and to be involved in disease control.

This knowledge is derived largely from studies in mice. Most studies on latent or active human TB or exposure to TB to date are limited to the analysis of peripheral blood lymphocytes (PBLs) and do not address the immunological situation at the primary site of MTB infection, the lung. The investigation of latent TB is, moreover, hampered for lack of an appropriate animal model for this state of disease.

The tine-skin test (TST) assesses the presence of cellular immune reactivity directed against *mycobacterium* species as a response to intradermal PPD injection. It can not differentiate between infection with mycobacteria other than tuberculosis (MOTT), vaccination with *Bacille Calmette Guerin* (BCG) and clinically relevant *M. tuberculosis* infection. It also provides no information about the exact antigen-specificity and involvement of CD4 or CD8+ T-cells and their differentiation status or homing capacity. Several variables are important to determine effective containment of *mycobacterium* species: CD4+ T-cells appear to be crucial to fight off infection in acute infection, CD8+ T-cells are more likely to be involved in maintaining long-term anti-MTB immune responses. Also, different T-cell subsets are important to maintain a strong and long-lived immune response. A pool of 'precursor' T-cells, immediate acting 'effector' T-cells, or memory T-lymphocytes, which are free to leave the bloodstream and to enter the site of infection with different potentials of proliferation or cytokine production, may be advantageous in order to achieve maximum and long-lived protection. A precise dissection of immune responses in different target antigens has heretofore not been known, but would allow discrimination between patients with MTB, MOTT or *M. leprae* infection. Exclusively ESAT-6 is expressed in MTB (and *M. leprae*) but not in BCG, or MOTT which designates this protein as an attractive vaccine candidate and target to gauge bona fide MTB-specific T-cell responses. Conversely, HLA-DR4 restricted Ag85b epitopes may—in addition to MTB diagnostics—be useful to enumerate T-cells specific for *M. ulcerans*, the causative agent of Buruli ulcer or *M. avium intracellulare*, a frequent cause for infections in immunocompromised patients. Thus, the TST as well as the IFNγ response assay (IGRA) are not able to address the above mentioned facets of an MTB-specific and effective immune response, since both assay systems implement PPD (purified protein derivative), a mix of different target proteins and lipoproteins as the stimulating agents and do not implement defined antigen specific peptide epitopes. A similar situation is true for the ELISPOT assay, which requires in most cases a 72 hr incubation period and does not allow simultaneous T-cell enumeration and T-cell marker analysis associated with T-cell homing and differentiation.

A more recently developed method of detecting antigen-specific T cells utilizing tetramers, oligomers or multimers of major histocompatibility complex (MHC) molecules has revolutionized T cell analysis. For example, MHC tetramer complexes are formed by the association of four MHC monomers, for example, four MHC class I molecule/β2-microglobulin monomers, with a specific peptide antigen and a detectable label such as a fluorochrome. Such MHC class I molecule tetramer complexes bind to a distinct set of T cell receptors on a subset of CD8+ T cells, including cytotoxic T lymphocytes (CTLs). CTLs, which are effector CD8+ T cells, do not necessarily represent the whole antigen-specific pool of CD8+ T cells. In this respect, the LDA and cytokine assay both detect CTLs or subpopulations of CTLs, whereas the MHC tetramer method can detect all antigen-specific CD8+ T cells, including naive and anergic CD8+ T cells, which do not exhibit effector functions. By mixing the MHC tetramers with peripheral blood lymphocytes or whole blood, and using flow cytometry as a detection system, a count of all T cells that are specific for a peptide and its matched allele is provided. As such, the MHC tetramers allow for the measurement of a cellular response against a specific peptide.

Spectratyping of the TCR repertoire allows for each individual TCR variable CDR3 profile obtained from 24 TCR VB families to be depicted as a function of the CDR3 length. Each peak represents 3 bp coding for one amino acid residue, with 9 or 10 amino acids being identified in each CDR3 profile. In the three-dimensional spectratype, the area of the entire CDR3 analysis is estimated as 100% for each TCR VB family, and the area under the curve for each individual CDR3 peak is expressed as the percentage of the entire CDR3 area, Spectratyping reflects the structural composition of the TCR repertoire, but does not provide information pertaining to the quantity of each TCR VA plus VB family, since the PCR-based amplification of the variable regions is not quantitative.

The use of MHC tetramers to analyze T cell specificity is quantitative; it does not require the use of radioactive dyes; and it is readily adapted to high throughput assay formats. In addition, the method can be performed quickly and, therefore, can be used to examine fresh blood or tissue samples. Where the MHC tetramer complex includes a fluorescent label, a cell population including T cells can be further stained with one or more other fluorescently labeled molecules, for example, fluorescently labeled molecules specific for other cell surface molecules and analyzed using flow cytometry, thus allowing additional characterization of the responding cells. In this case, the additional fluorescent label is selected to fluoresce at a wavelength that is readily distinguishable from the label(s) used to stain the target cells. Furthermore, MHC tetramer analysis is not toxic to the labeled cells and, therefore, tetramer binding cells can be sorted into uniform populations by flow cytometry and examined by additional assays to confirm their functional ability, for example, the ability to proliferate in response to antigen.

Therefore, there is a need in the art for methods of diagnosing in humans the factors responsible for containing MTB and sustaining latency in the human lung. The ex vivo identification of anti-MTB reactive CD4+ or CD8+ T-cells is desirable in order to provide biologically meaningful surrogate markers for gauging the efficacy of novel vaccine candidates, for diagnosing and monitoring latent MTB infections, for detecting MTB exposure, for testing for eradication of MTB in the course of already established and novel treatment strategies, and for defining the immunological threshold required to maintain 'protective immunity'.

SUMMARY OF THE INVENTION

The invention solves these and other problems in the art by providing isolated human HLA-DR4-restricted T-cell epitopes derived from *Mycobacterium tuberculosis* (MTB). The epitopes comprise an amino acid sequence as set forth in SEQ ID NOS: 3, 6, 7 or 8, for example.

In one embodiment, the invention provides isolated polynucleotides encoding a polypeptide having an amino acid sequence as set forth in SEQ ID NO:3, 4, 5, 6, 7, or 8.

In another embodiment, the invention provides methods for diagnosing the presence of an infection by, or exposure to MTB in a human subject. The method includes contacting peripheral blood lymphocytes (PBLs) obtained from the subject with multimers or oligomers of HLA-DR4 monomers or modified monomers, having a bound HLA-binding peptide having an amino acid sequence as set forth in SEQ ID NO:8, and detecting binding of the multimers or oligomers to the PBLs wherein the binding of the tetramers to PBLs is indicative of the presence of MTB infection or exposure in the subject.

In another embodiment, the invention provides methods for diagnosing the presence of an infection by, or exposure to, MTB in a human subject. The method includes contacting PBL obtained of the subject with tetramers, oligomers or multimers of HLA-A2 monomers, or modified monomers, having a bound HLA-binding peptide comprising an amino acid sequence as set forth in SEQ ID NO:3, and detecting binding of the tetramers, oligomers or multimers to the PBLs wherein the binding of the tetramers to PBLs is indicative of the presence of MTB infection or exposure in the subject.

In another embodiment, the invention provides methods for determining efficacy of a drug for treatment or prevention of infection or latency of MTB in a human subject. The method includes obtaining a sample of PBLs from a patient with a DR4 allelle undergoing treatment for latent MTB using the drug and contacting the sample under suitable binding conditions with a solid support having bound tetramers, oligomers, or multimers of HLA monomers or modified monomers. The tetramers, oligomers, or multimers of HLA monomers or modified monomers include HLA-DR4 monomers or modified monomers having a bound HLA-binding peptide comprising an amino acid sequence selected from the amino acid sequences set forth in SEQ ID NO: 6, 7, 8; and HLA-A2 monomers or modified monomers having a bound HLA-binding peptide comprising an amino acid sequence as set forth in SEQ ID NO: 1, 2 or 3. The amount of binding of the tetramers to the PBLs is detected. After a suitable interval of treatment time, the process is repeated and the results are compared. If the comparison shows a decrease in the amount of the binding after the suitable interval of treatment time, efficacy of the drug is indicated, and a lack of decrease indicates lack of efficacy of the drug for treatment or prevention of infection or latency of MTB in the human.

In another embodiment, the invention provides methods for determining efficacy of a drug for treatment of infection or latency of MTB in a human subject. The method includes obtaining a sample comprising PBLs from a patient with a DR4 allelle undergoing treatment for MTB using the drug and contacting the sample under suitable binding conditions with a solid support having bound tetramers, oligomers or multimers of HLA monomers or modified monomers. The tetramers, oligomers, or multimers of HLA monomers or modified monomers include HLA-DR4 monomers or modified monomers having a bound HLA-binding peptide comprising an amino acid sequence selected from the amino acid sequences set forth in SEQ ID NO: 6, 7, and 8; and HLA-A2 monomers or modified monomers having a bound HLA-binding peptide comprising an amino acid sequence as set forth in SEQ ID NO: 1, 2 or 3. The amount of binding of the tetramers to the PBLs is detected. After a suitable interval of treatment time, the process is repeated and the results are compared. If the comparison shows a decrease in the amount of the binding after the suitable interval of treatment time, efficacy of the drug is indicated, and a lack of decrease indicates lack of efficacy of the drug for treatment of infection or latency of MTB in the human.

In another embodiment, the invention provides methods in which PBLs obtained from a subject are contacted with tetramers of HLA monomers or modified monomers having a bound HLA-binding peptide. The subject has an HLA-DR4 allelle and the binding peptide comprises an amino acid sequence as set forth in SEQ ID NO:8. Alternatively, the subject has an HLA-A2 allelle and the binding peptide comprises an amino acid sequence as set forth in SEQ ID NO:3. Binding of the tetramers to the PBLs is detected to identify the presence of *M. leprae* or *M. tuberculosis* infection or exposure in the subject.

In another embodiment, the invention provides methods in which PBLs obtained from a subject are contacted with tetramers of HLA monomers or modified monomers, having a bound HLA-binding peptide. The subject has an HLA-DR4 allelle, the monomer is an HLA-DR4 monomer and the binding peptide comprises an amino acid sequence as set forth in SEQ ID NO:6 or 7. Alternatively, the subject has an HLA-A2 allelle, the monomer is an HLA-A2 monomer, and the binding peptide comprises an amino acid sequence as set forth in SEQ ID NO:1 and/or 2. Binding of the tetramers to the PBLs is detected to identify the presence of mycobacterial exposure or infection other than by *M. leprae* or *M. tuberculosis* in the subject.

A BRIEF DESCRIPTION OF THE FIGURES

Figure 1B:
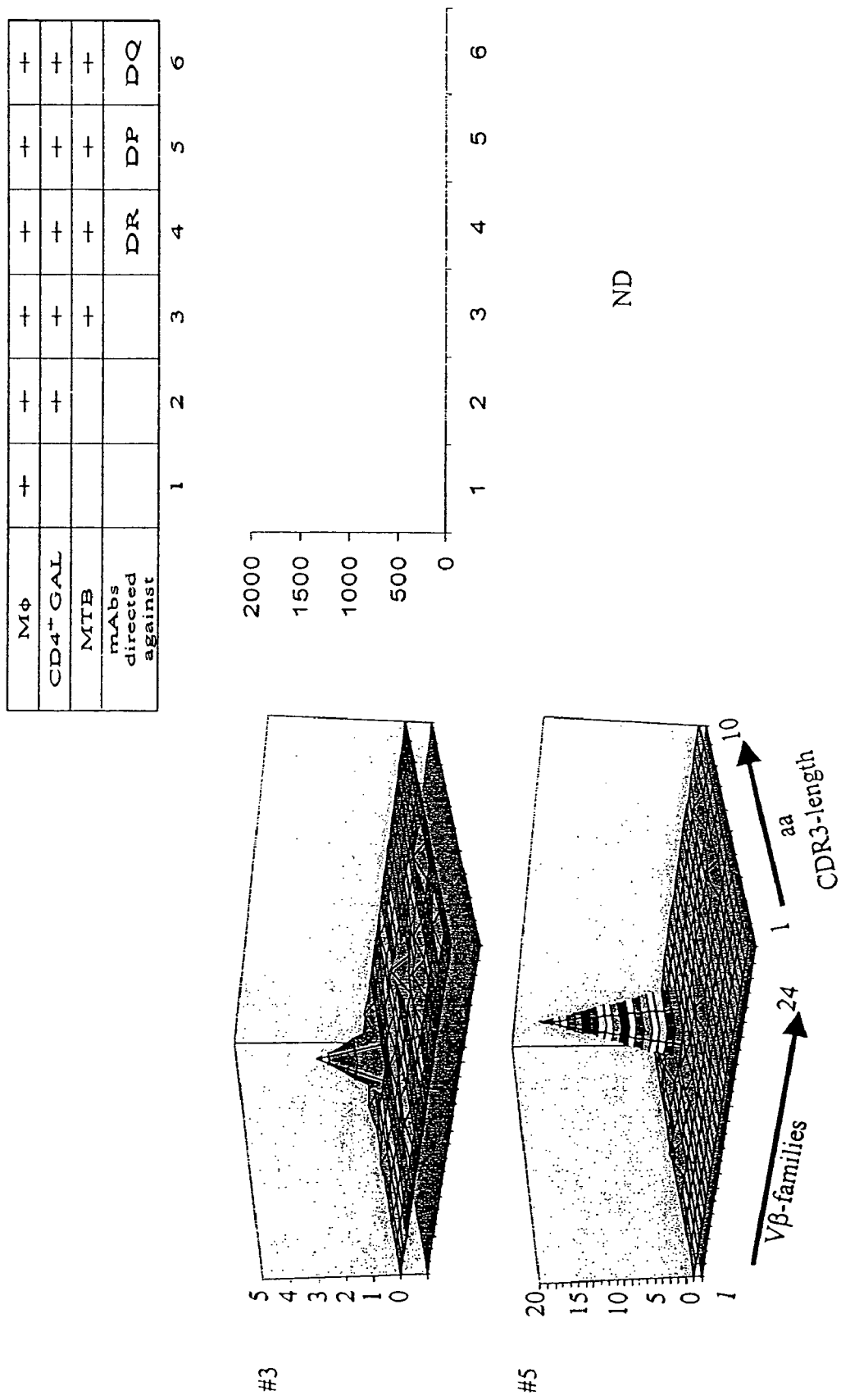
Figure 1C:
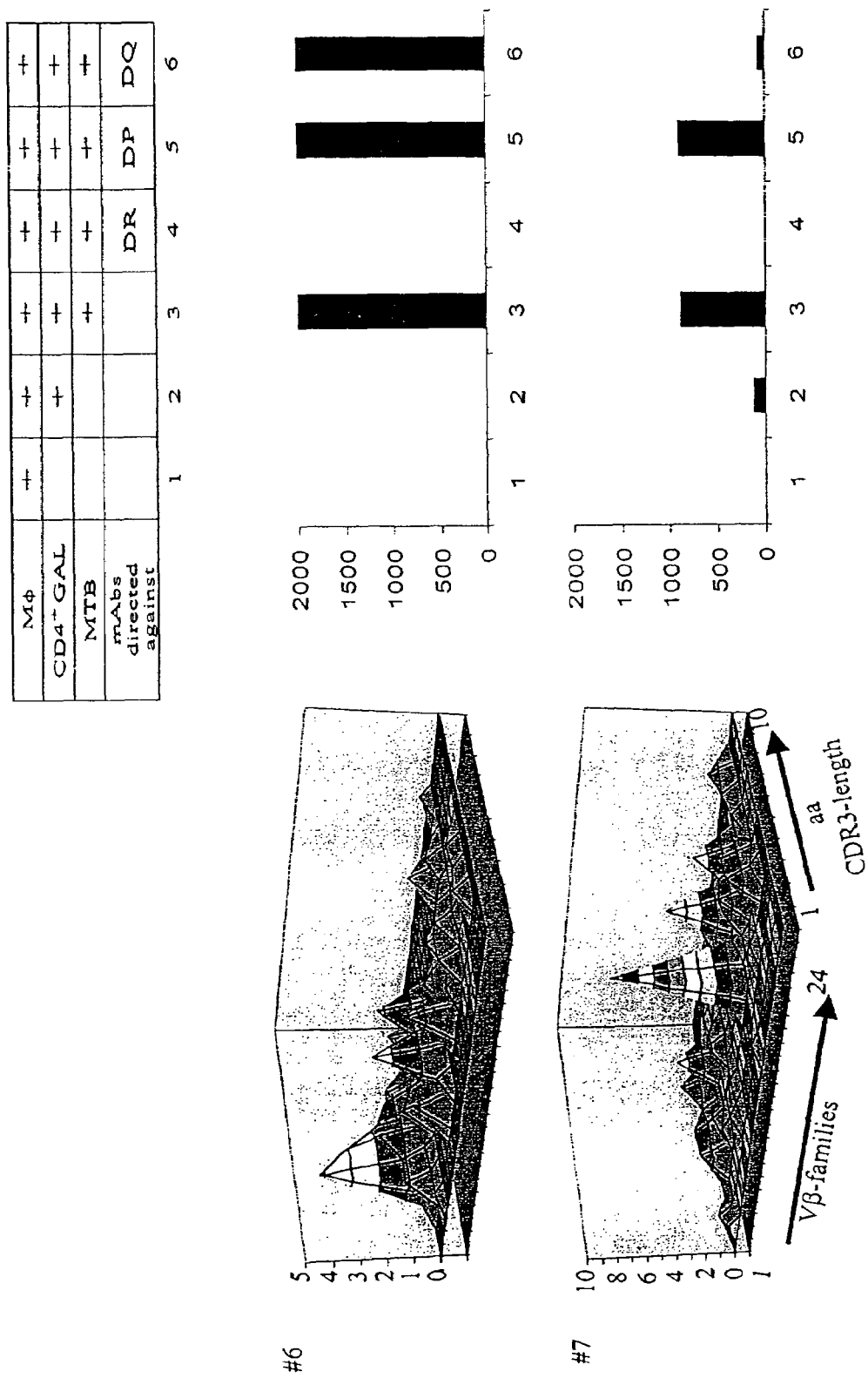

FIGS. 1A-C Granuloma associated lymphocytes (GAL) have been obtained from pulmonary lesions from patients with MTB infection who were able to contain the disease, i.e. with no clinically apparent tuberculosis. GAL were separated into CD4 (FIG. 1 A-C) and CD8 (FIG. 2A-C) and evaluated for the molecular composition (TCR landscape) and cytokine release in response to autologous macrophages infected with MTB. FIG. 1A, patients #1 and #2; DR, DP, DQ serve as restricting elements. FIG. 1B, patients #3 and #5; no IFN release. FIG. 1C, patient #6: DR-restricted response; Patient #7: DR and DQ restricted response as defined by blocking with mAbs.

Figure 2A:
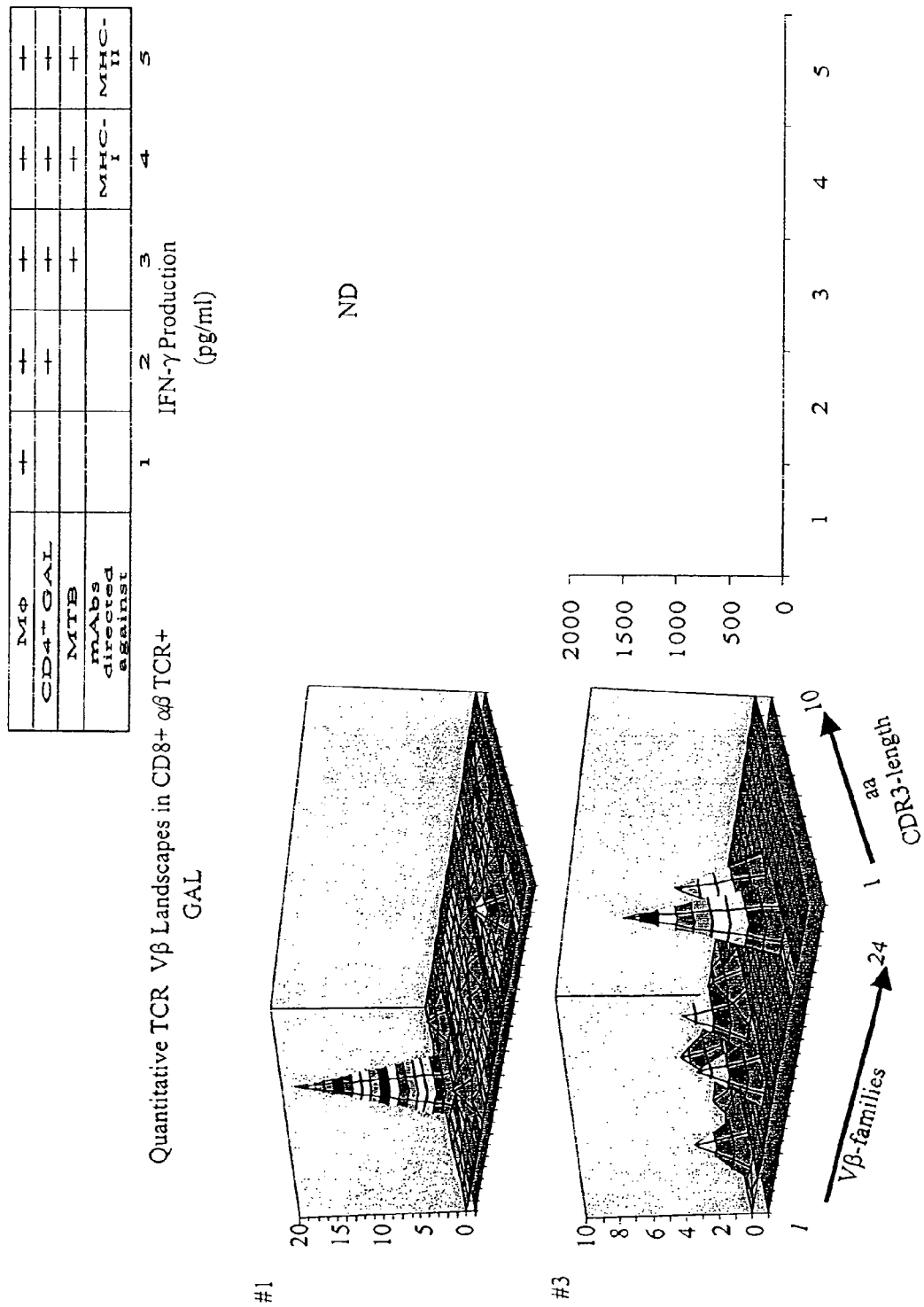
Figure 2B:
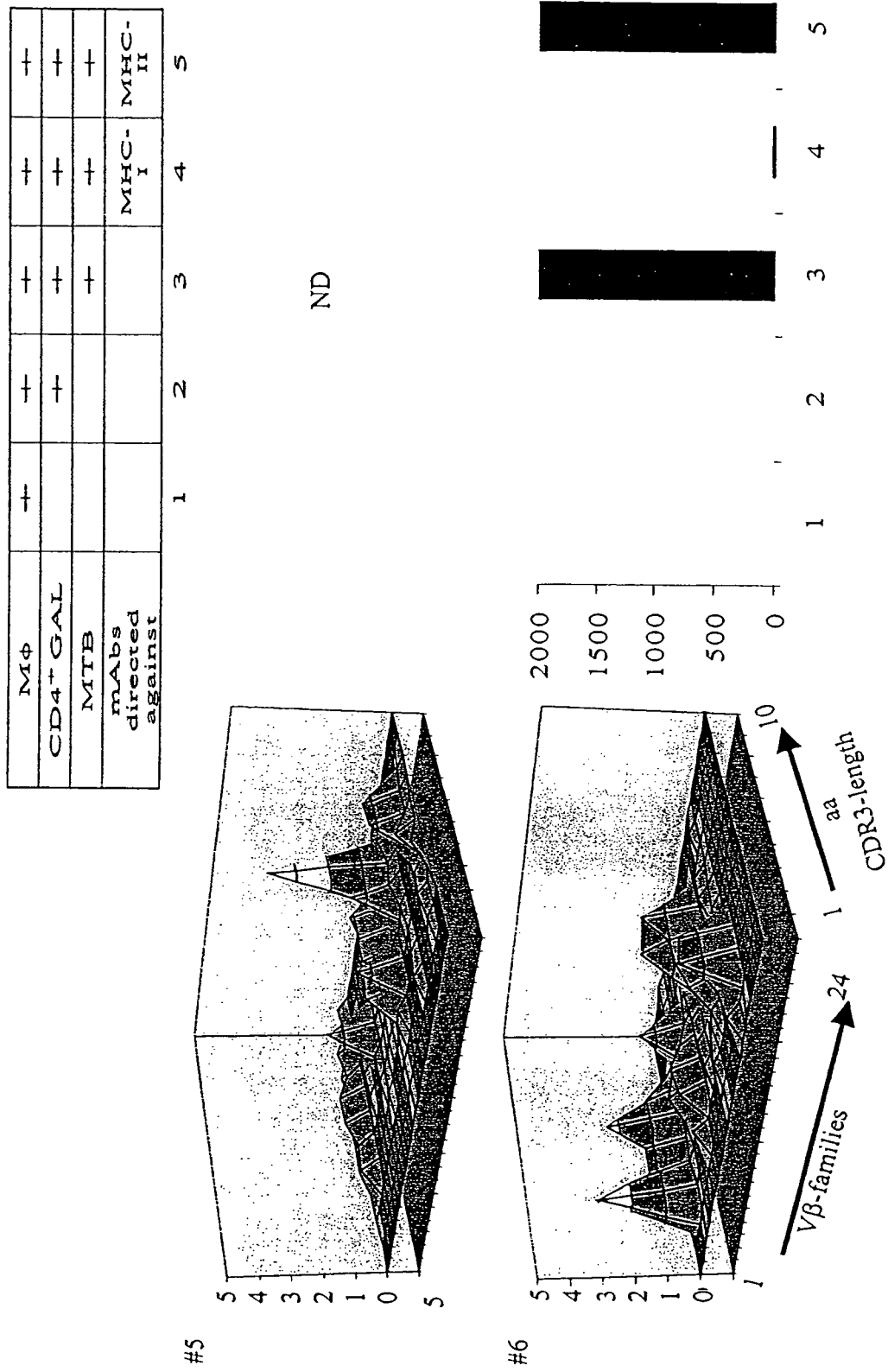
Figure 2C:
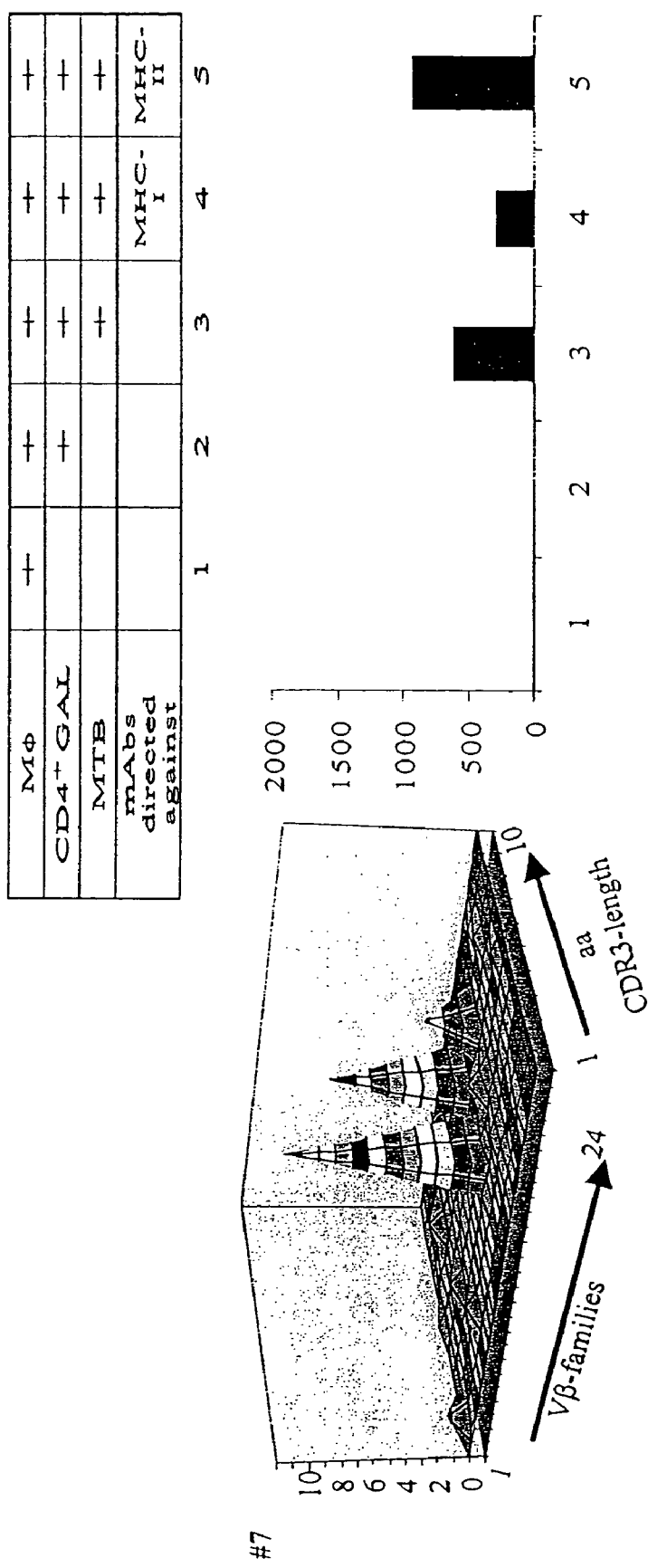

FIGS. 2A-C are a series of the 'TCR landscapes' plotted for CD8+ αβ TCR+ GAL for patients tested and corresponding graphs showing that cytokine production is MHC class I restricted and is not inhibited by mAbs directed against DR, DP, and DQ in the CD8+ GAL population. FIG. 2A, patient #1 and patient #3: no cytokine response. FIG. 2B, patients #5 and patient #6: MHC class I restricted CD8+ response defined by blocking with the anti-MHC class I w6/32 mAb. FIG. 2C, patient #7: only partial blocking with the anti-MHC directed blocking mAb.

FIGS. 3A and 3B show a spectratype analysis for patient #2. FIG. 3A shows the results of CDR3-analysis for patient #2 (for both CD4+ and CD8+ T-cells) in the GALs. FIG. 3B shows the 'TCR landscape' obtained by subtracting the results obtained in the GALs from the 'TCR landscape' obtained for PBL to visualize the percent differences in the molecular composition of CD4+ or CD8+ T-cells in different anatomic compartments (GAL vs. PBS).

FIGS. 4A and 4B show the results of spectratype analysis of data obtained for patient #5. FIG. 4A shows the 'TCR landscape' obtained by subtracting the results in the (CD4+, CD8+, unsorted) GAL 'TCR landscape' from the 'TCR landscape' obtained for PBL to visualize the percent differences (for total/unsorted PBL and GAL). Only the molecular composition is depicted. FIG. 4B, identical data, except that the values are corrected by the TCR VB frequencies defined by flow-cytometry: Amplification of individual VB families in GAL vs. PBL.

Figure 5C:
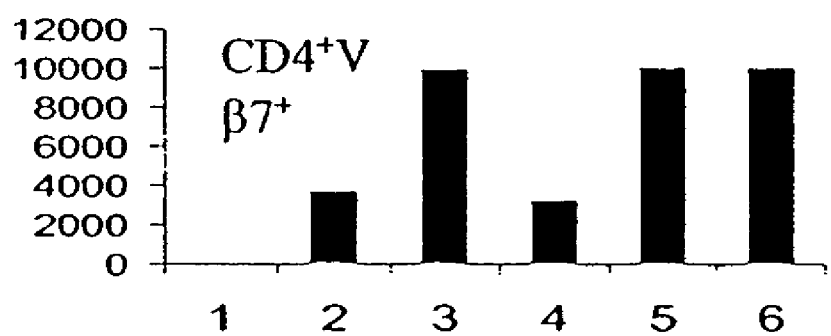

FIGS. 5A-C show a series of graphs and tabular representations of the production of IFN-γ by patient T-cells were at higher concentrations than were produced by the whole population of GALs at comparative cell counts. T-cell effector populations have been sorted using specific TCR-VB mAbs, i.e. data from VB9+ or VB14+ T-cells in the CD4+ or from VB3+ T-cells in the CD8+ T-cell population. FIG. 5A=patient #1; FIG. 5B=patient #2; FIG. 5C=patient #5.

FIGS. 6A-F show an analysis of the ability of Vβ-sorted T-cells to recognize MTB derived peptide $ESAT-6_{1-20}$ and $ESAT-6_{72-95}$ to narrow down the epitope recognized by GAL in ESAT-6. After these results, we created the DR4/ESAT-6 tetramer-complex. Thus, we have 2 peptides pulsed on DCs $ESAT_{1-20}$ and $ESAT_{72-95}$, and the respective DR4 binding peptide $ESAT6_{8-22}$ which has been tetramerized (FAGIEAAASAIQGNV) (SEQ ID NO:8)). FIGS. 6A-B, patient #1, FIGS. 6C-D, patient #2; FIGS. 6E-F, patient #5. Peptide $ESAT_{1-20}$ is more frequently recognized as compared to $ESAT_{72-95}$. In addition, the $ESAT_{1-20}$ response is apparently DR-restricted since the anti-DR mAb L243 significantly abrogates T-cell recognition.

Figure 7A:
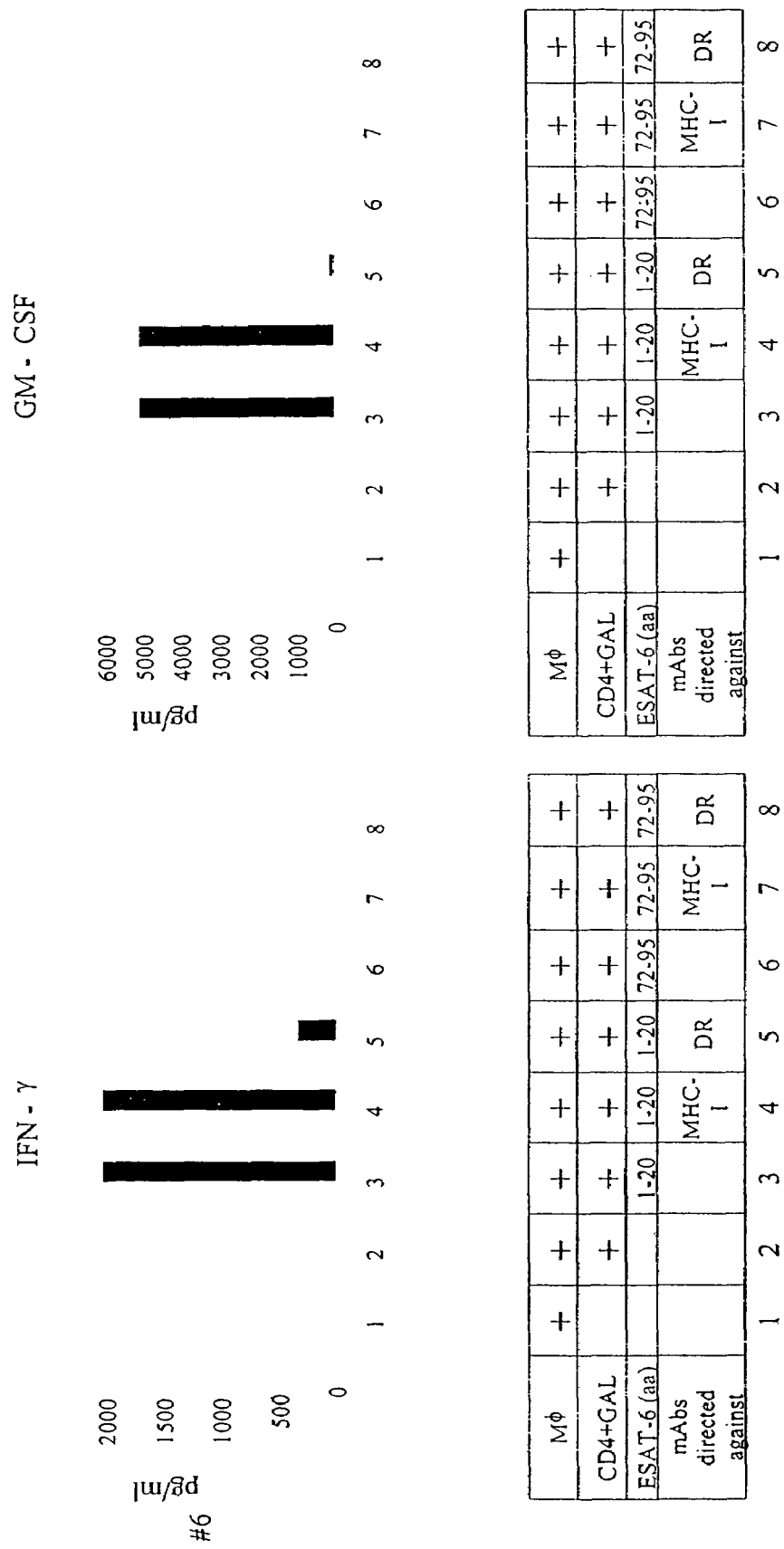
Figure 7B:
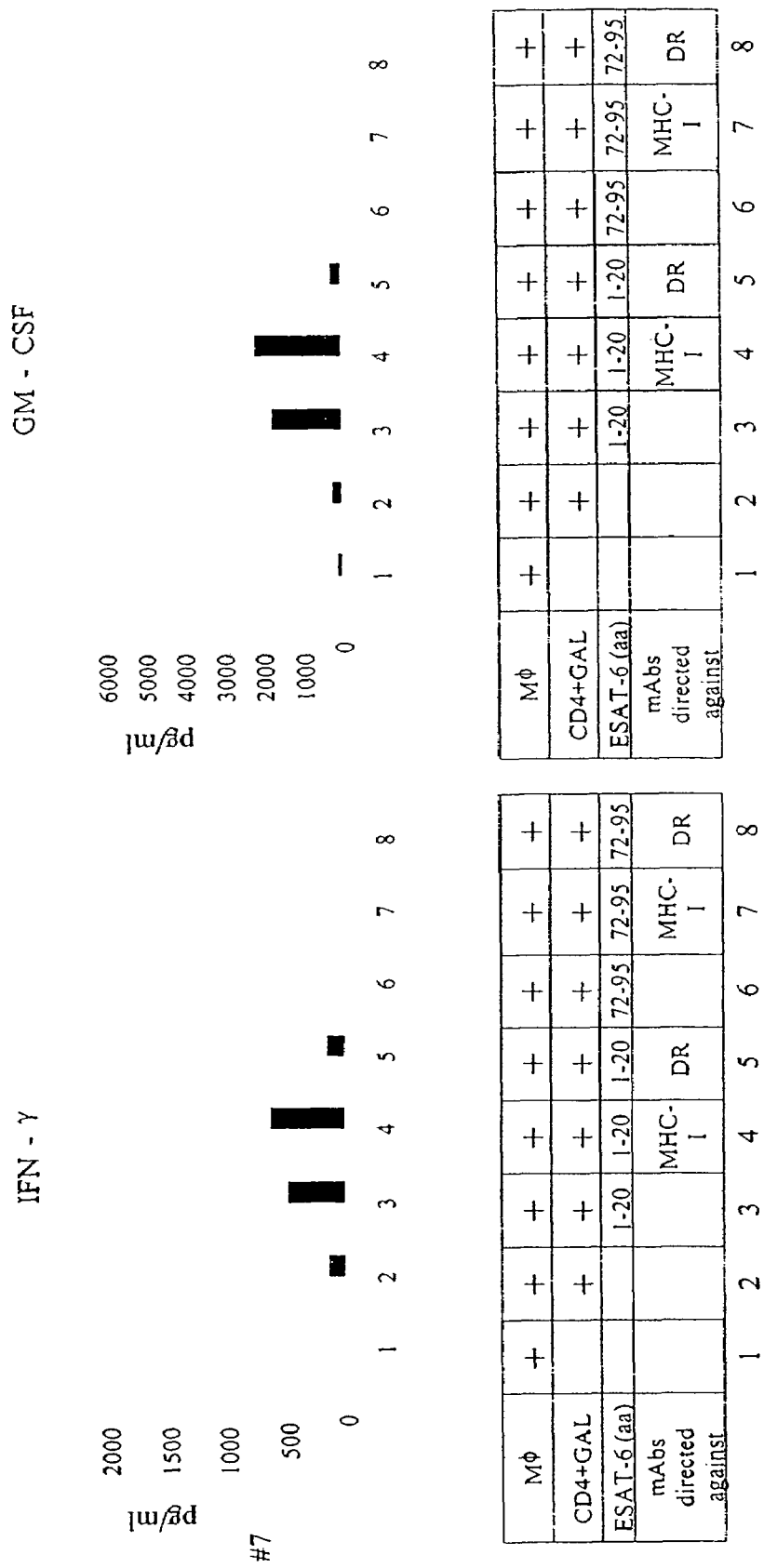

FIGS. 7A and 7B are graphs showing the ESAT-6-specific immune response to $ESAT-6_{1-20}$ in both patients without pathological lesions particular of TB in the biopsy led to production of substantial amounts of IFN-γ and GM-CSF, which could be blocked by mAbs directed against HLA-DR. FIG. 7A, patient #6, FIG. 7B, patient #7.

Figure 8A:
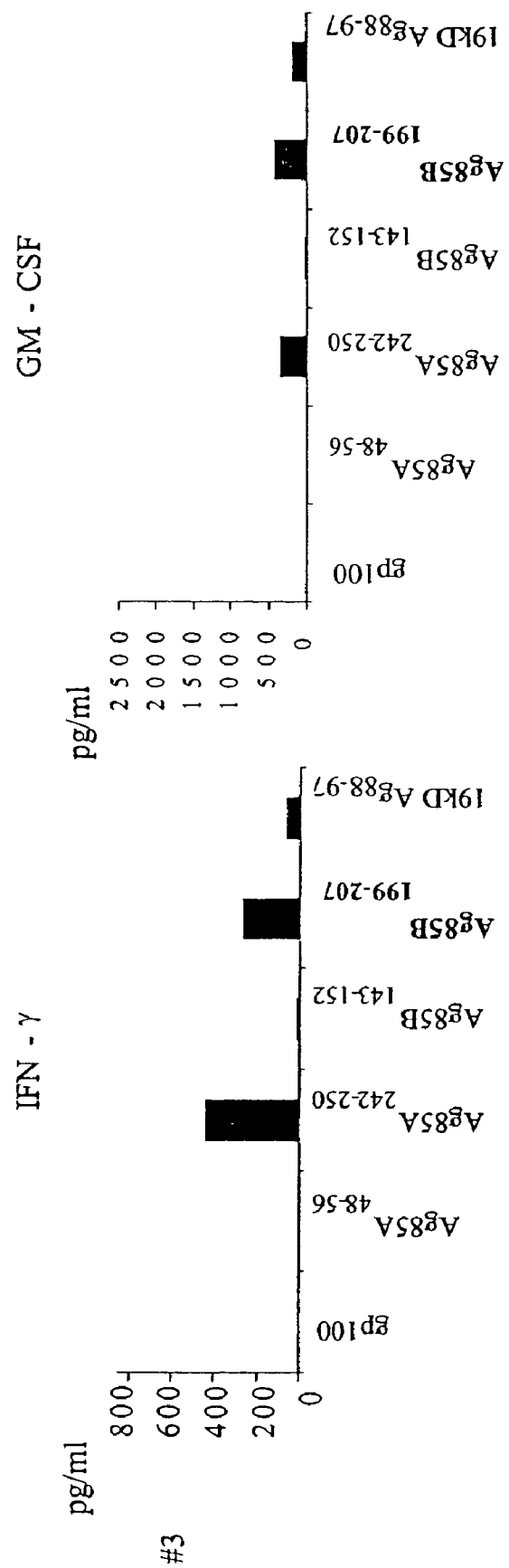
Figure 8B:
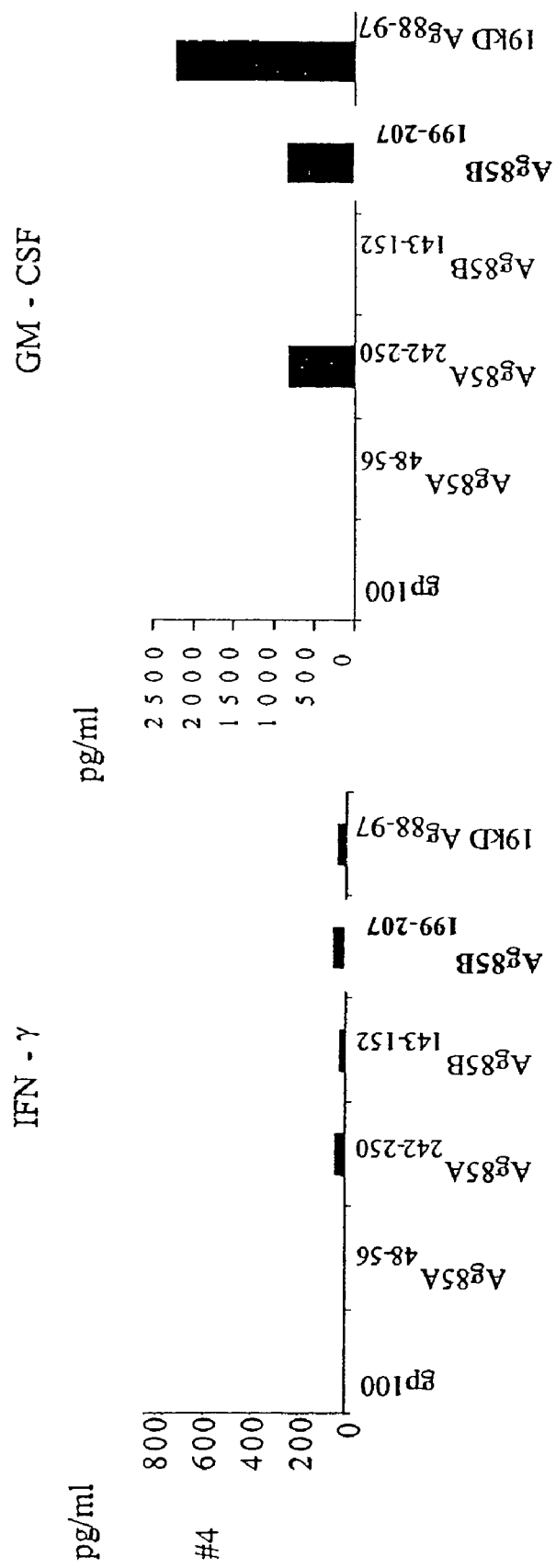
Figure 8C:
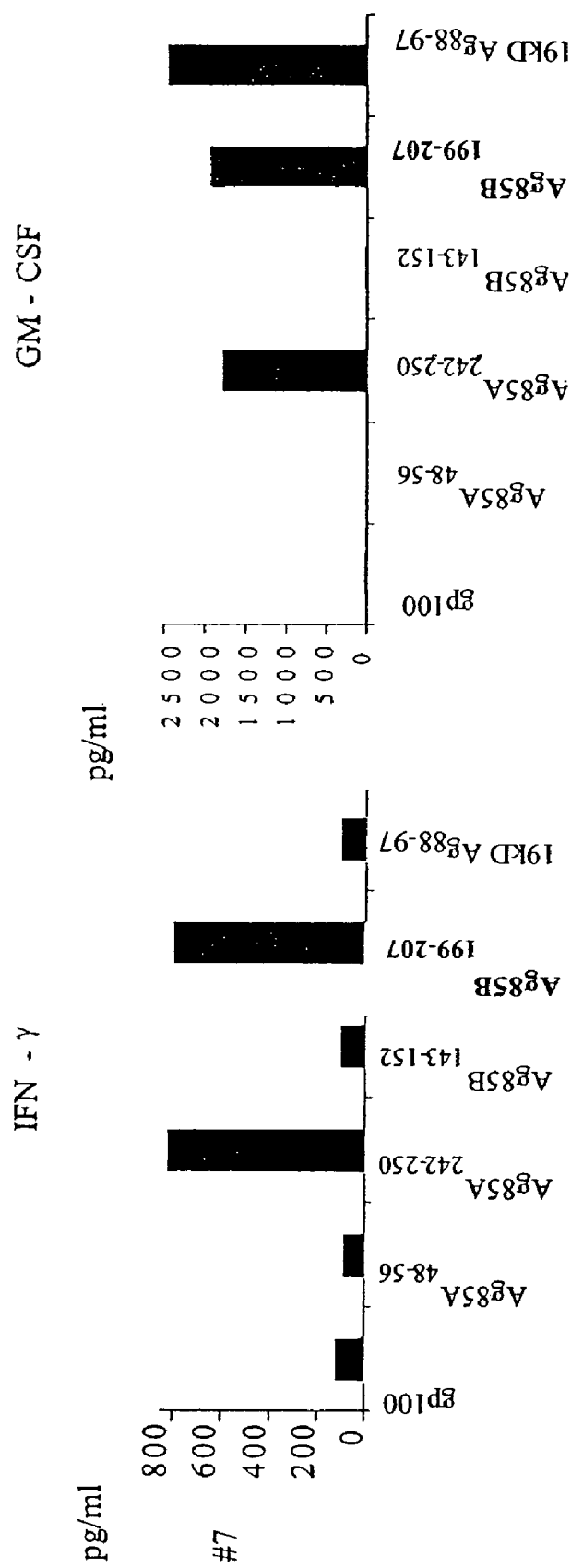

FIGS. 8A-C are graphs showing IFN-γ and GM-CSF production by CD8+ T-cells directed against the HLA-A2 binding peptides from the 19 kDa Ag, Ag85a or Ag85b target peptides in patients #3, #4 and #7. FIG. 8A, patient #3; FIG. 8B, patient #4; and FIG. 8C, patient #7. These data show that the CD8+ T-cell response in GAL is focused on the $AG85a_{242-250}$ and $Ag85b_{199-207}$, defined by IFNγ production.

Figure 9A:
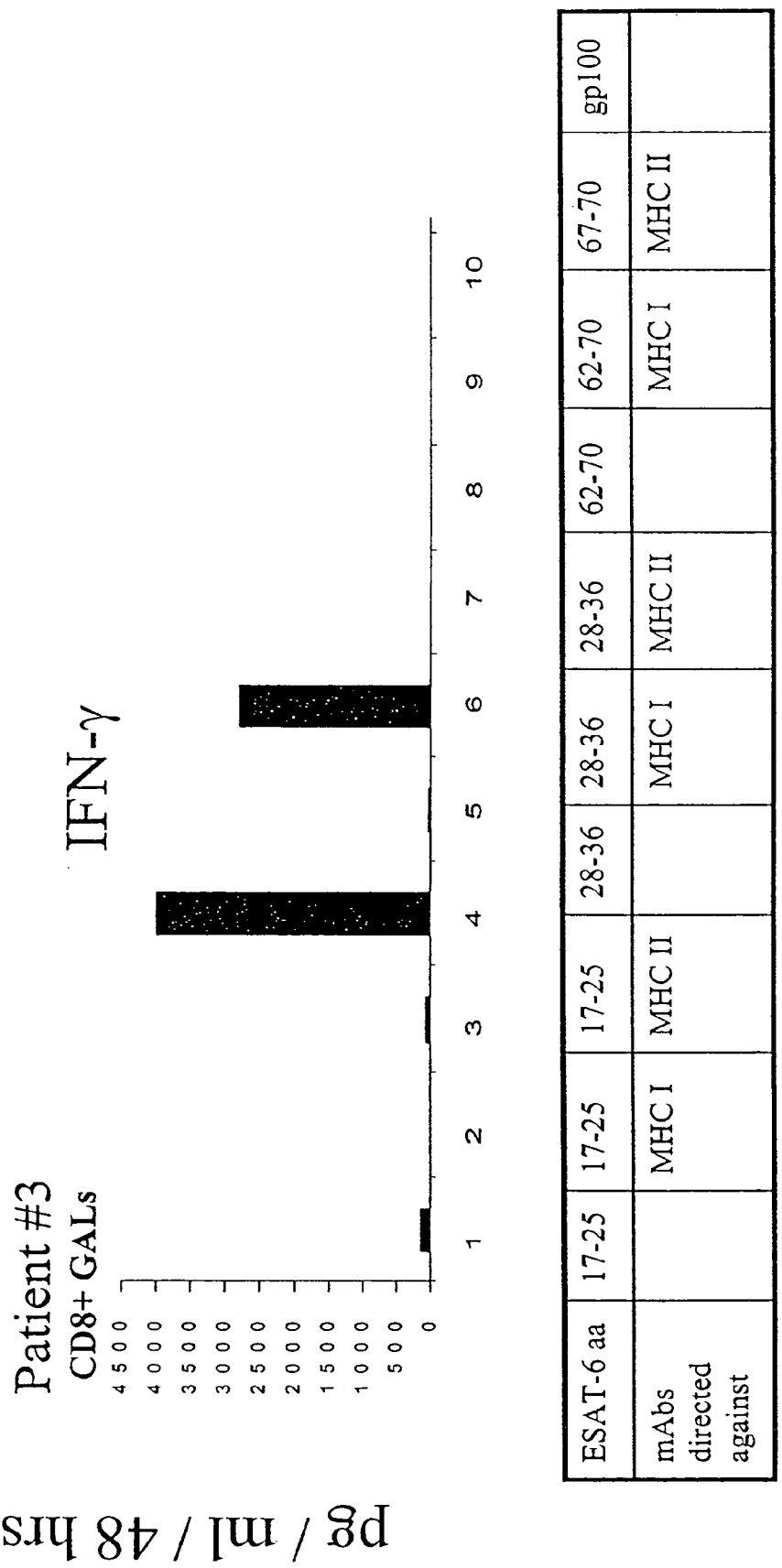
Figure 9B:
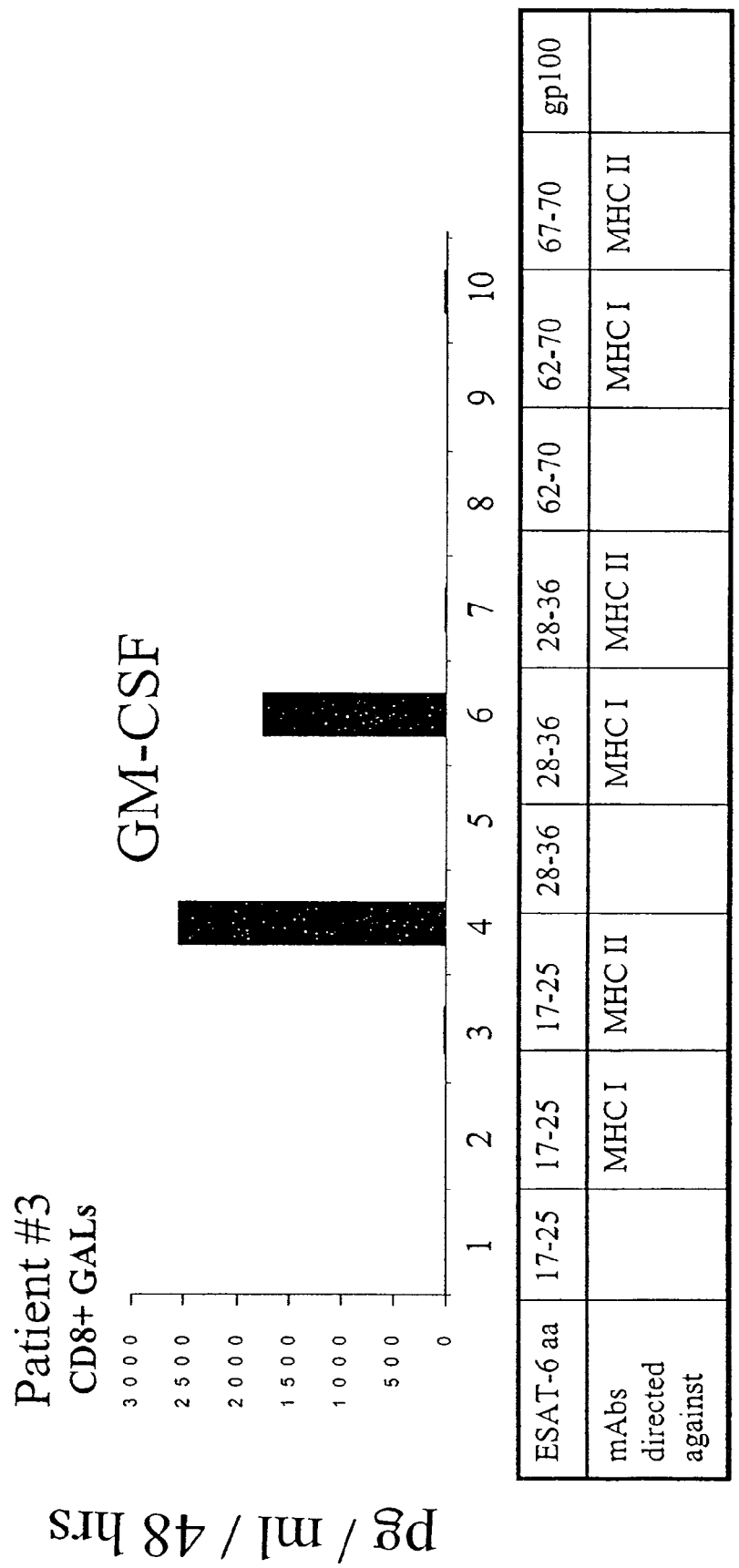

FIGS. 9A and 9B show the production of cytokine by CD8+ GAL of a patient with tuberculosis (patient #3) in response to three different candidate peptides from the MTB associated protein ESAT-6. $ESAT-6_{28-36}$ is recognized. This response can be blocked with the anti-MHC class I directed mAb w6/32.

FIGS. 10A-D are a series of four graphs showing the results of Ex vivo analysis of tetramer-sorted CD4+ T-cells using either the Ag85b or the ESAT-6 epitope clearly showed that CD4+, HLA-DR4-restricted, and Ag85b-reactive T-cells recognized naturally processed and presented epitopes provided from *M. tuberculosis* and from *M. avium intracellulare*. Note that Ag85b-sorted T-cells recognize MTB and *M. avium intracellulare*. In contrast, DR4/ESAT-6 sorted T-cells recognize exclusively MTB bacilli.

Figure 11A:
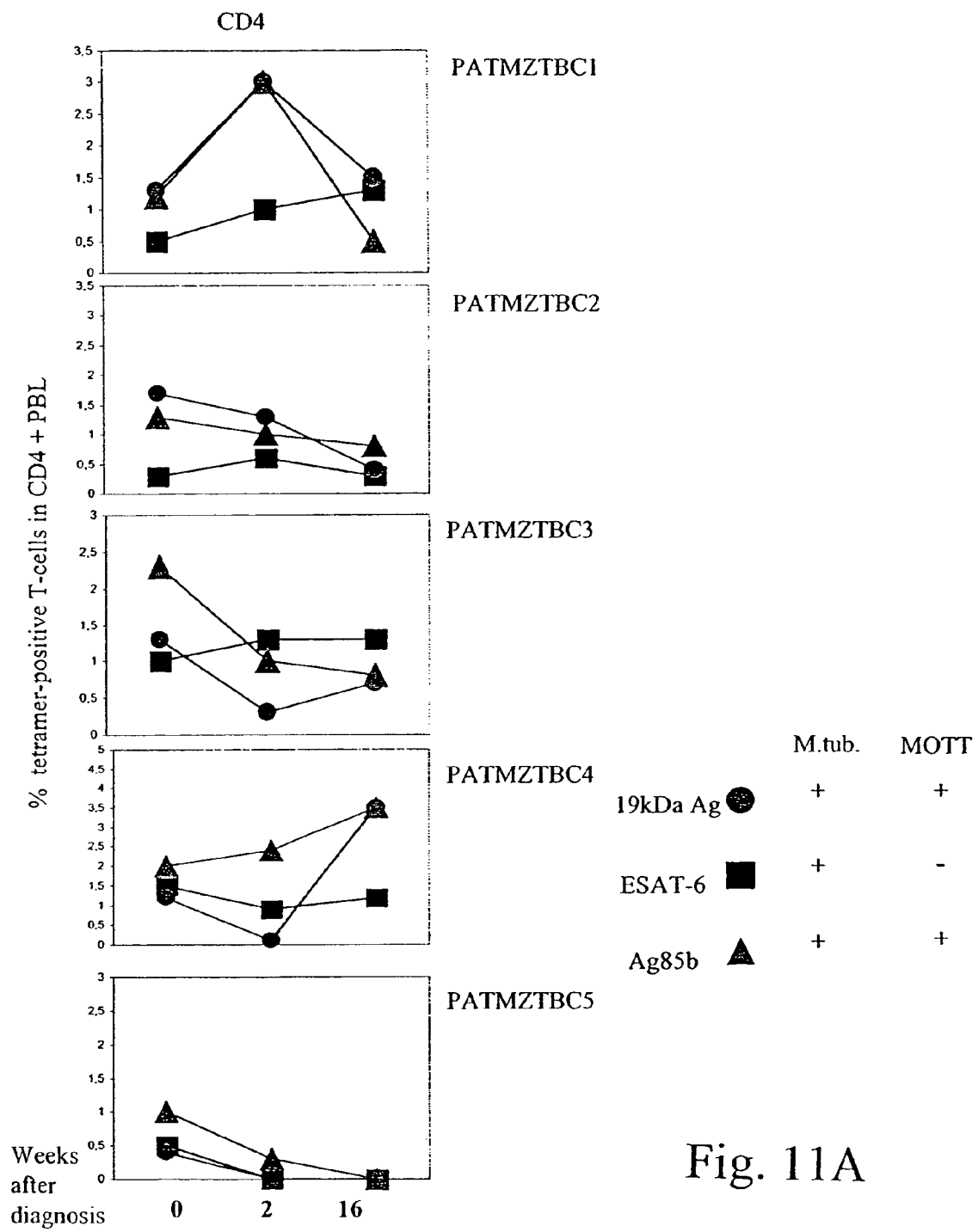

FIG. 11A is a series of graphs showing PBL reactivity to the 19 kDa antigen, the Ag85b and ESAT-6 in HLA-DR4-restricted CD4+ T-cells of five patients with pulmonary tuberculosis at the time of diagnosis and again at 2 and 16 weeks after diagnosis and concurrent initiation of therapy (horizontal axis).

Figure 11B:
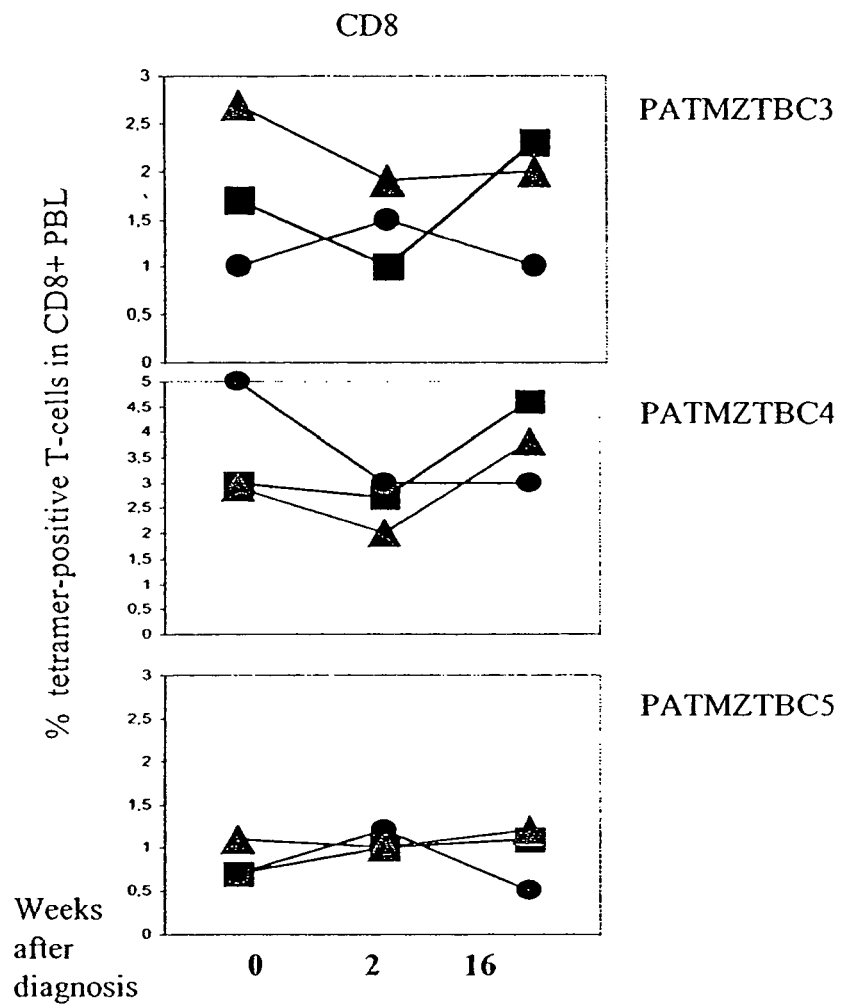
Figure 12A:
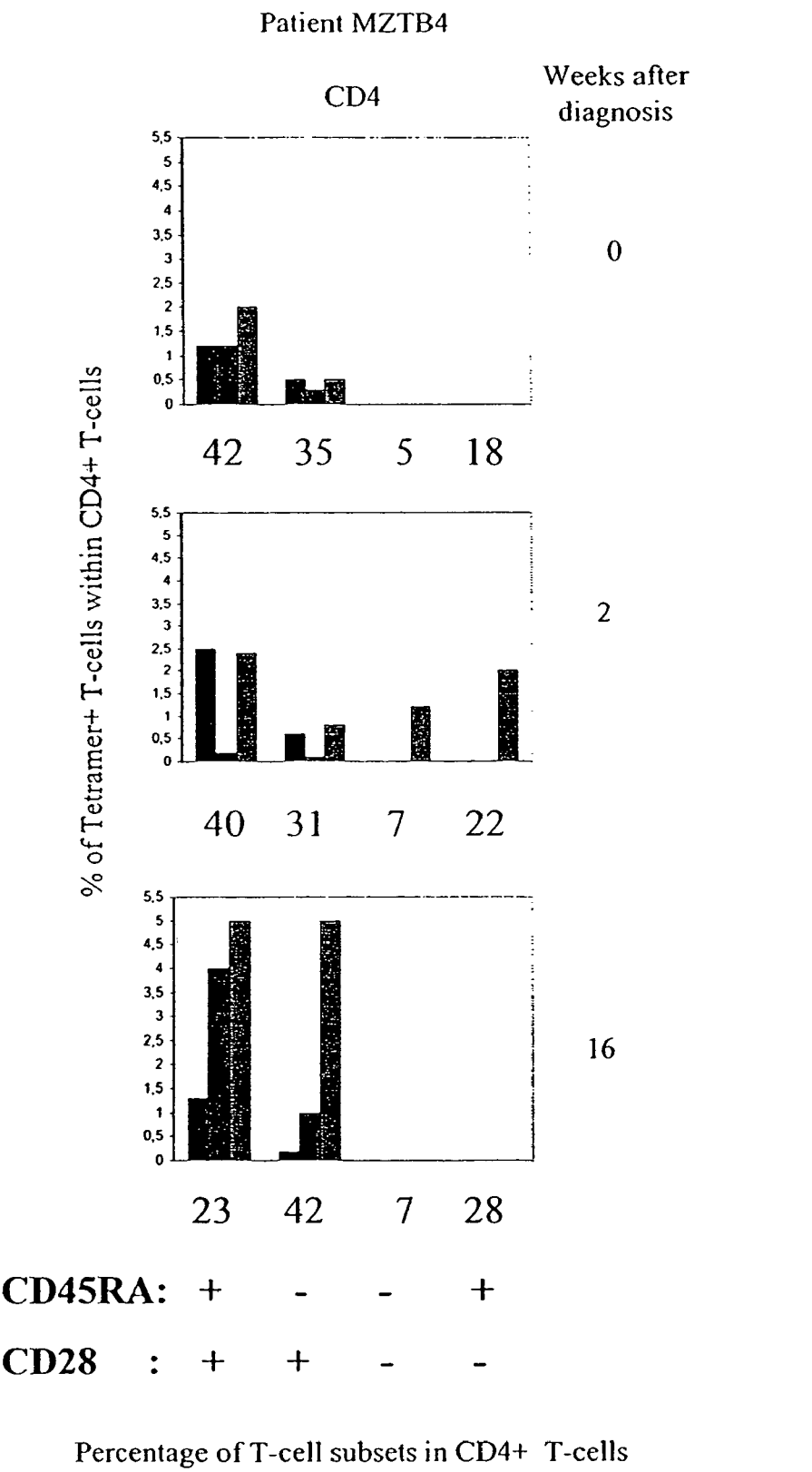
Figure 12B:
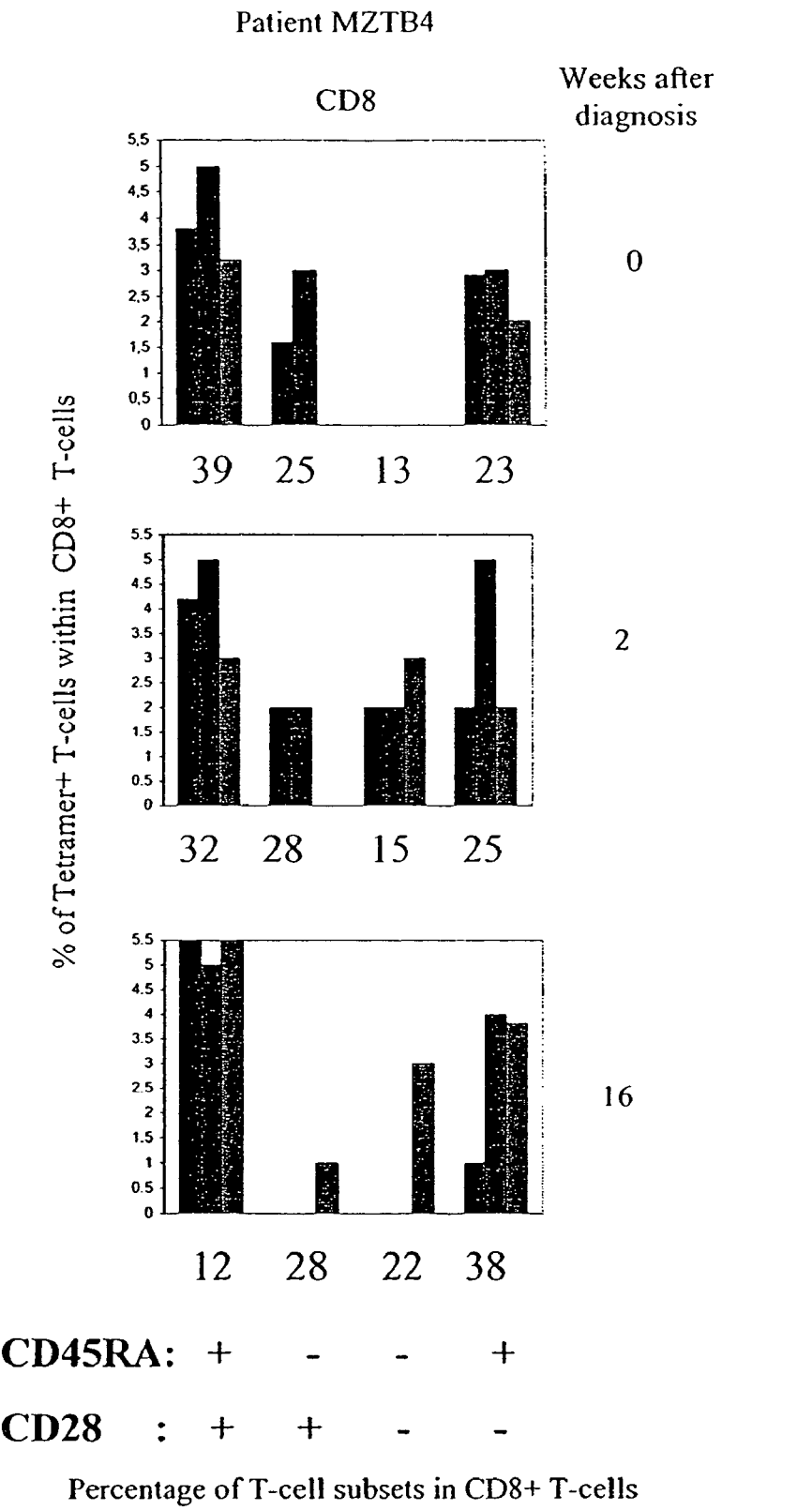

FIG. 11B are a series of graphs showing PBL reactivity to the 19 kDa antigen, the Ag85b and ESAT-6 in HLA-DR4-restricted CD8+ T-cells of three of five patients with pulmonary tuberculosis at the time of diagnosis and again at 2 and 16 weeks after diagnosis and concurrent initiation of therapy (horizontal axis). PATMZTBx=Patient MZTBx FIGS. 12A and 12B are a series of graphs showing reactivity of blood samples of Patient MZTB4 compiled in FIGS. 11A-B for the presence of mycobacterium antigen-reactive T-cells in different T-cell subsets based on differential staining with CD45RA and CD28. (In each set of three bars, bar1=ESAT-6; bar2=19 DaAg; bar3=Ag85b.)

Figure 13A:
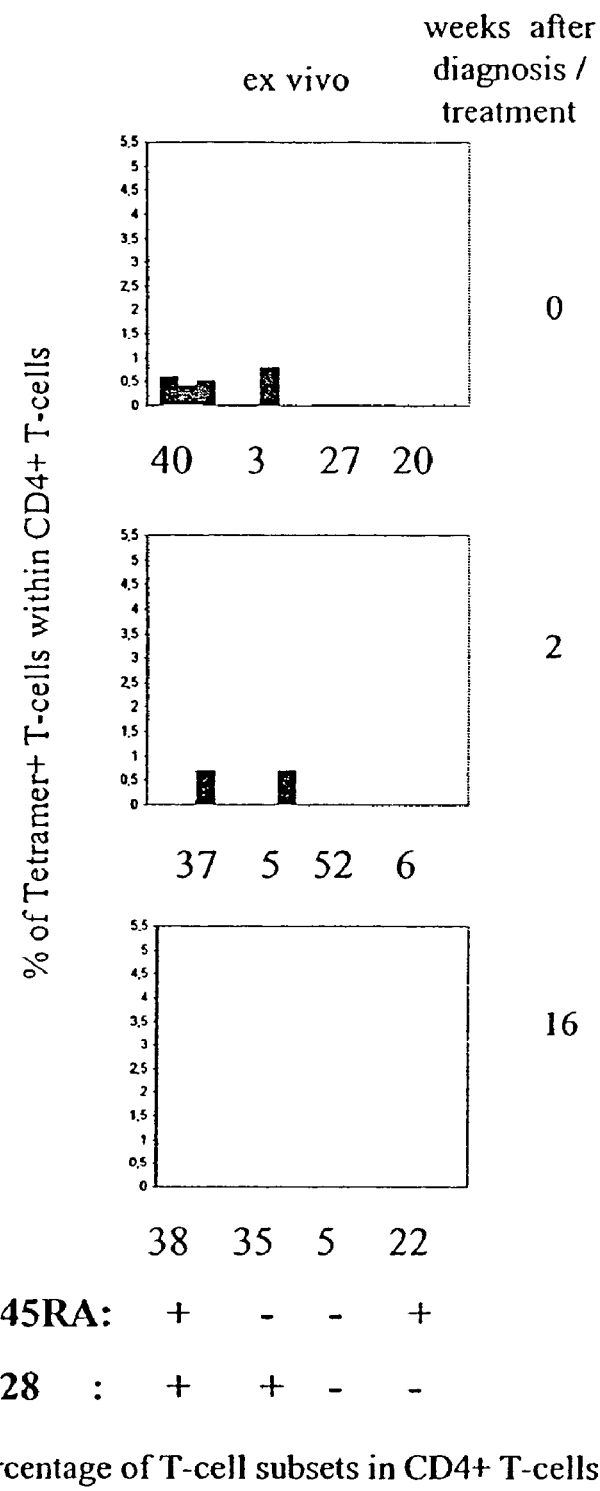
Figure 13B:
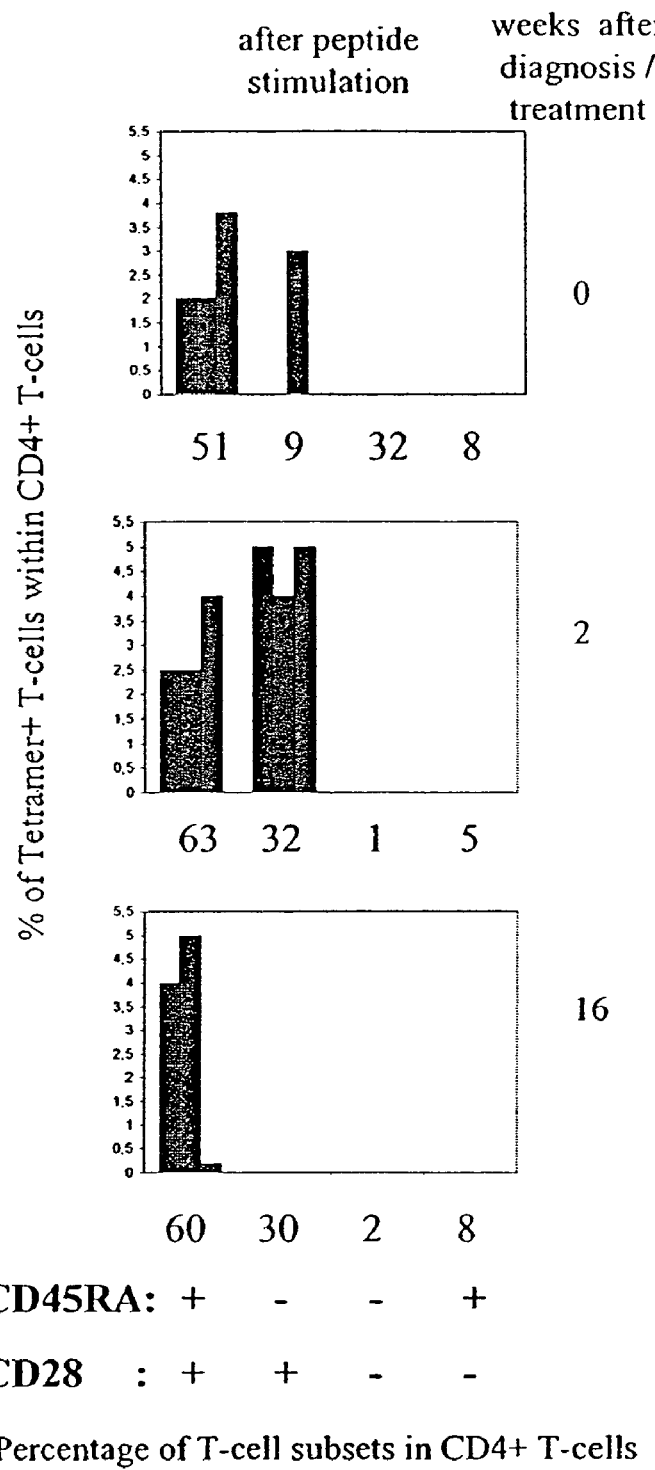

FIGS. 13A and 13B is a graph showing low or undetectable CD4+ T-cells in patients with tuberculosis (e.g. PBL from patient MZTBC5) that recognize either the AG85b, 19 kDa, or ESAT-6 antigen in the context of DR4 (FIG. 13A), could be expanded during a 7 day stimulation with the appropriate peptide in vitro: the predominant CD4+ T-cell response (FIG. 13B) is again detected within the precursor (CD45RA+, CD28+) or in the activated (CD45RA−CD28+) T-cell subset. (In each set of three bars, bar1=ESAT-6; bar2=19 DaAg; bar3=Ag85b.)

FIGS. 14A and 14B show dispersed localization of tetramer-reactive GALs through in situ tetramer staining. FIG. 14A shows HE staining for a parallel section from the tissue specimen obtained from patient #3 shows granuloma formation (magnification ×200). FIG. 14B shows 10-20 frozen sections at 10 μm thickness from lung tissue were stained with HLA A2 tetramers for $Ag85b_{199-207}$ and 19-kDa $Ag_{88-97}$ or gp100 as a negative control, co-stained with CD8 mAbs and visualized by CLSM. Tetramer-binding GALs appear dispersed within the granuloma, while a homogeneous distribution of CD8 was apparent in GALs, tetramer stained TCRs seemed localized at one or a few poles of the cell. Data presented for patients #3 and #4. Background staining for the irrelevant control (gp100) tetramer (magnification ×400). Note that tetramer-guided analysis of HLA-A2 restricted/Ag85b-reactive T-cells has been carried out in GAL from patient #3 (see FIG. 15).

FIGS. 15A-C show focused T-cell response to defined MHC/peptide complexes. FIG. 15A shows tetramer-guided sorting of HLA-A2 restricted/Ag85b-specific T-cells (left) in CD8+ GAL from patient #3 (see FIGS. 1 and 2). Sufficient CD4+ GAL could successfully be harvested from a different (HLA-DR4+) patient with latent MTB infection, not listed in Table 1, and sorted using an HLA-DR4/ESAT-6 tetramer complex (right). FIG. 15B shows TCR repertoire analysis in either CD8+, HLA-A2/Ag85b-specific (left) or CD4+, HLA-DR4/ESAT-6 specific T-cells isolated from granuloma tissue. Data are presented as % overrepresentation of TCR VB families in tetramer-sorted T-cells as compared to CD8+, or CD4+ GAL, respectively. FIG. 15C illustrates that individual VB families could be quantitatively assessed using a panel of TCR-VB-specific mAbs in CD4+ GAL. TCR VB4 and VB7 are monoclonal in HLA-DR4/ESAT-6 reactive CD4+ GAL.

DETAILED DESCRIPTION OF THE INVENTION

The present invention is based on the discovery that MHC class I and class II-restricted and MTB epitope specific T-cells can be directly visualized in peripheral blood without the need for in vitro manipulation using newly identified MHC-binding peptide epitopes provided from antigens associated with mycobacterium infection. The observation that ex vivo-sorted DR4/peptide tetramer-reactive T-cells recognize epitopes from naturally processed and presented target antigens on autologous macrophages (FIG. 10) and that DR4+/MTB peptide tetramer complexes specifically stain granuloma-associated lymphocytes in granuloma tissue from tine-test positive individuals (FIG. 14) demonstrates the biological significance of these HLA presented peptides. The simultaneous testing of antigen-specific T-cells in combination with T-cell differentiation marker analysis provides a new platform to gauge MTB-directed immune responses in latent TB.

| HLA-DR4 restricted T-cell epitopes | | |
|---|---|---|
| Antigen | DR4 | SEQ ID NO: |
| 19 kDa Ag$_{143-157}$ (e.g. NCBI protein bank NP-336818, identical to aa 122-136 from F70732, conserved lipoprotein) | QMPYQPVQSPTQVEA | SEQ. ID NO: 6 |
| Ag85b$_{7-21}$ (e.g. in the Ag85b-precursor molecule, e.g. Genbank accession # AF 198032) | PVEYLQVPSPSMGRD | SEQ. ID NO: 7 |
| ESAT-6$_{8-22}$ (e.g. in Genbank accession # 79 562) | FAGIEAAASAIQGNV | SEQ. ID NO: 8 |

| Tetramer analysis for the ESAT-6 peptide LLDEGKQSL, an HLA-A2-Restricted T-cell epitope | | |
|---|---|---|
| Antigen | A2 | SEQ ID NO: |
| 19 kDa antigen$_{88-97}$ e.g. in Genbank accession # X07945 | VLTDGNPPEV | SEQ ID NO: 1 |
| Ag85b Aa 199-207 according to Geluk et al., J. Immunol. 165: 6463-71, 2000; or aa 210-218 in the Ag85b precursor molecule, e.g. Genbank accession # AF 198032 | KLVANNTRL | SEQ ID NO: 2 |
| ESAT-6$_{28-36}$ e.g. in Genbank accession # X79 562 | LLDEGKQSL | SEQ ID NO: 3 |
| Ag85a$_{48-56}$ | GLPVEYLQV | SEQ ID NO: 21 |
| Ag85a$_{242-250}$ | KLIANNTRV | SEQ ID NO: 22 |
| Ag85b$_{143-152}$ | FIYAGSLSAL | SEQ ID NO: 23 |
| ESAT-6$_{17-25}$ | AIQGNVTSI | SEQ ID NO: 24 |
| ESAT-6$_{62-70}$ | ATAELNNA | SEQ ID NO: 25 |

These HLA A*0201-restricted peptides from 19 kDa Ag and Ag85b have already been described in PBL, we add here the evidence that the focus of the CD8+ GAL from patients with MTB is on the Ag85b epitope.

The invention provides, in one embodiment, an isolated human HLA-A2-restricted T-cell epitope derived from *Mycobacterium tuberculosis* (MTB), said epitope comprising an amino acid sequence as set forth in SEQ ID NO:3, herein, and conservative variations thereof. This T-cell epitope is associated with infection with or exposure to MTB or mycobacteria other than MTB in humans. In another embodiment, the invention provides an isolated human HLA-DR4-restricted T-cell epitope derived from *Mycobacterium tuberculosis* (MTB), said epitope comprising an amino acid sequence as set forth in SEQ ID NOS: 6, 7 or 8 herein, and conservative variations thereof.

In another embodiment, the invention provides isolated polynucleotides encoding the invention epitopes having SEQ. ID NOS: 3 and 6, 7, and 8 as well as conservative variations of the invention epitopes, including those which are degenerate as a result f the genetic code. The polynucleotides can be DNA, cDNA, RNA, mRNA and the like. The invention polynucleotides can be used to recombinantly produce the invention T-cell epitopes. Expression vectors as disclosed herein, such as viral vectors, including the invention polynucleotides that encode the invention T-cell epitopes are also provided, as are host cells stably transformed with such vectors.

In still another embodiment, the invention provides methods for diagnosing the presence of a infection by or exposure to MTB in a human subject comprising contacting peripheral blood lymphocytes (PBLs) obtained from the subject with multimers or oligomers of HLA-DR4 monomers or modified monomers, having a bound HLA-binding peptide comprising an amino acid sequence as set forth in SEQ ID NO:8, and detecting binding of the multimers or oligomers to the PBLs wherein the binding to PBLs is indicative of the presence of MTB infection or exposure in the subject. The invention methods are particularly suitable for detecting binding of the tetramers, oligomers or multimers using high throughput screening techniques as are known in the art. For example, a tetramer used in the invention methods can be labeled with a fluorophore, such as is described in the Examples herein, and the detecting comprises measuring the signal produced by the fluorophore. The invention method can further comprise contacting the PBLs with additional tetramers of HLA-DR4 monomers or modified monomers, having a bound HLA-binding peptide comprising an amino acid sequence as set forth in SEQ ID NO:6 or 7 and detecting binding of at least one of the additional tetramers to the PBLs.

In still another embodiment, the invention provides methods for diagnosing the presence of an infection by or exposure to MTB in a human subject, comprising:

a) contacting PBL obtained of the subject with tetramers of HLA-A2 monomers, or modified monomers, oligomer or multimers having a bound HLA-binding peptide comprising an amino acid sequence as set forth in SEQ ID NO:3; and b) detecting binding of the tetramers to the PBLs wherein the binding of the tetramers to PBLs is indicative of the presence of MTB infection or exposure in the subject. The method can further comprise contacting the PBLs with additional tetramers, oligomers or multimers of HLA-A2 monomers, or modified monomers, having a bound HLA-binding peptide comprising an amino acid sequence as set forth in SEQ ID NO:1 or 2 and detecting binding of at least one of the additional tetramers to the PBLs.

In another embodiment, the invention provides methods for diagnosing the presence of an infection by or exposure to MTB in a human subject by contacting PBLs obtained of the subject with tetramers, oligomers or multimers of HLA-A2 monomers, or modified monomers, having a bound HLA-binding peptide comprising an amino acid sequence as set forth in SEQ ID NO:3, and detecting binding of the tetramers, oligomers or multimers to the PBLs wherein the binding of the tetramers to PBLs is indicative of the presence of MTB infection or exposure in the subject. The method can further comprise contacting the PBLs with additional tetramers, oligomers or multimers of HLA-A2 monomers, or modified monomers, having a bound HLA-binding peptide comprising an amino acid sequence as set forth in SEQ ID NO:1 or 2 and detecting binding of at least one of the additional tetramers to the PBLs.

In yet another embodiment, the invention provides methods for determining efficacy of a drug for treatment or prevention of infection or latency of MTB in a human subject, comprising:

a) obtaining a sample comprising PBLs from a patient with a DR4 allele undergoing treatment for latent MTB using the drug;

b) contacting the sample under suitable binding conditions with a solid support having bound tetramers, oligomers, or multimers of HLA monomers or modified monomers selected from at least one of
1) HLA-DR4 monomers or modified monomers, having a bound HLA-binding peptide comprising an amino acid sequence selected from the amino acid sequences set forth in SEQ ID NO: 6, 7, 8; and
2) HLA-A2 monomers or modified monomers, having a bound HLA-binding peptide comprising an amino acid sequence as set forth in SEQ ID NO: 1, 2 or 3. The amount of binding of the tetramers to the PBLs is detected. After a suitable interval of treatment time, the process is repeated and the results are compared. If the comparison shows a decrease in the amount of the binding after the suitable interval of treatment time, efficacy of the drug is indicated, and a lack of decrease indicates lack of efficacy of the drug for treatment or prevention of infection or latency of MTB in the human. As in other embodiment of the invention methods, the method for determining the efficacy of drugs or drug candidates is well suited to any form of high thoughput screening using adaptations known in the art for drug screening drug candidates and can be used in preliminary screening of anti-TB vaccine candidates or for screening chemical compounds (i.e., "small molecules") known to decrease or arrest growth in vitro of any mycobacterium.

Still another embodiment of the invention provides methods for determining efficacy of a drug for treatment of infection or latency of MTB in a human subject by obtaining a sample comprising PBLs from a patient with a DR4 allele undergoing treatment for MTB using the drug; contacting the sample under suitable binding conditions with a solid support having bound tetramers, oligomers or multimers of HLA monomers or modified monomers selected from at least one of 1) HLA-DR4 monomers or modified monomers, having a bound HLA-binding peptide comprising an amino acid sequence selected from the amino acid sequences set forth in SEQ ID NO: 6, 7, and 8; and 2) HLA-A2 monomers or modified monomers, having a bound HLA-binding peptide comprising an amino acid sequence as set forth in SEQ ID NO: 1, 2 or 3. The amount of binding of the tetramers to the PBLs is detected. After a suitable interval of treatment time, the process is repeated and the results are compared. If the comparison shows a decrease in the amount of the binding after the suitable interval of treatment time, efficacy of the drug is indicated, and a lack of decrease indicates lack of efficacy of the drug for treatment of infection or latency of MTB in the human.

In yet another embodiment, the invention provides methods in which PBLs obtained from a subject are contacted with tetramers of HLA monomers or modified monomers, having a bound HLA-binding peptide, wherein the subject has an HLA-DR4 allele and the binding peptide comprises an amino acid sequence as set forth in SEQ ID NO:8, or wherein the subject has an HLA-A2 allele and the binding peptide comprises an amino acid sequence as set forth in SEQ ID NO:3. Binding of the tetramers to the PBLs is detected to identify the presence of *M. leprae* or *M. tuberculosis* infection or exposure in the subject.

In still another embodiment, the invention provides methods in which PBLs obtained from a subject are contacted with tetramers of HLA monomers or modified monomers, having a bound HLA-binding peptide, wherein the subject has an HLA-DR4 allele, the monomer is an HLA-DR4 monomer and the binding peptide comprises an amino acid sequence as set forth in SEQ ID NO:6 or 7, or wherein the subject has an HLA-A2 allele, the monomer is an HLA-A2 monomer, and the binding peptide comprises an amino acid sequence as set forth in SEQ ID NO:1 and/or 2. Binding of the tetramers to the PBLs is detected to identify the presence of mycobacterial exposure or infection other than by *M. leprae* or *M. tuberculosis* in the subject.

As used herein, the terms "MHC monomer" and "HLA monomer" refer to a class I MHC heavy chain that maintains the ability to assemble or is assembled into a ternary complex with an appropriate MHC-binding or HLA-binding peptide and beta-2 microglobulin (beta-2m) under renaturing conditions. The terms "MHC monomer" and HLA monomer" are also used to refer to the denatured form of the monomer that results from subjecting the ternary complex to denaturing conditions, causing the monomer to unfold and dissociate from an MHC-binding peptide and from beta-2 microglobulin.

As used herein, the terms "modified MHC monomer" and "modified HLA monomer" refer to class I monomers as described above, but which have been engineered to introduce modifications as described below. These terms also encompass functional fragments of the MHC monomer that maintain the ability to assemble into a ternary complex with an appropriate MHC-binding or HLA-binding peptide and beta-2 microglobulin under renaturing conditions and to dissociate under denaturing conditions. For example, a functional fragment can comprise only the $\alpha_1$, $\alpha_2$, $\alpha_3$, domains, or only $\alpha_1$, $\alpha_2$ domains, of the class I heavy chain, i.e., the cell surface domains, that participate in formation of the ternary complex. In another embodiment, modified MHC monomers can be class I heavy chain molecules, or functional fragments thereof, contained in a fusion protein or "single chain" molecule and may further include an amino acid sequence functioning as a linker between cell surface domains of the monomer, a detectable marker or as a ligand to attach the molecule to a solid support that is coated with a second ligand with which the ligand in the fusion protein reacts. Moreover the terms "modified MHC monomer" and "modified HLA monomer" are intended to encompass chimera containing domains of class I heavy chain molecules from more than one species or from more than one class I subclass. For example, a chimera can be prepared by substitution of a mouse beta-2m for human beta-2m in a human HLA-A2 monomer.

Minor modifications of the primary amino acid sequence for the invention epitopes of SEQ ID can result in proteins which have substantially equivalent activity as compared to the exemplified invention epitopes. Such modifications can be deliberate, such as modification introduced by a method such as site-directed mutagenesis, or can be spontaneous. All of the polypeptides produced by these modifications are encompassed within the present invention, provided the modification does not destroy the function of the epitope, e.g., its ability to bind to the corresponding T-cell restricted complex, as disclosed herein.

The polynucleotide sequence encoding an epitope of the invention includes the exemplified sequences (i.e., SEQ ID NOS:3, 6, 7 and 8 as well as conservative variations of the exemplified polypeptide sequences. The term "conservative variation" as used herein refers to a replacement of an amino acid residue by another, biologically similar amino acid residue. Examples of conservative variations include the substitution of a hydrophobic residue such as isoleucine, valine, or leucine for another, or the substitution of a polar residue for another, such as the substitution of arginine for lysine, glutamic for aspartic acid, or glutamine for asparagine, and the like. The term "conservative variation" also includes the use of a substituted amino acid in place of an unsubstituted parent amino acid, provided that an antibody that specifically interacts with the substituted epitope also is specifically immunoreactive with the unsubstituted epitope.

MHC tetramers, are complexes of four MHC monomers with streptavidin, a molecule having tetrameric binding sites for biotin, to which is bound a fluorochrome, e.g., phycoerythrin (PE). For class I monomers, the monomers also complex soluble subunits of β2-microglobulin, the peptide fragment containing a putative T-cell epitope, and of a MHC monomer corresponding to the predicted MHC subtype of the peptide fragment of interest, are obtained by expression of the polypeptides in host-cells. Under normal conditions, the MHC monomer is anchored to the cell surface of the antigen presenting cells even if the T cell expresses Class I monomers, (i.e., cross presentation). Each of the four monomers contained in the MHC tetramer is produced as a monomer by refolding these soluble subunits under conditions that favor assembly of the soluble units into reconstituted monomers, each containing a beta2-microglobulin, an MHC-binding peptide, and the corresponding MHC-molecule. An MHC tetramer is constructed from the monomers by biotinylation of the monomers and subsequent contact of the biotinylated reconstituted monomers with fluorochrome-labeled streptavidin. When contacted with a diverse population of T-cells, such as is contained in a sample of the peripheral blood lymphocytes (PBLs) of a subject, those tetramers containing reconstituted monomers that are recognized by a T-cell in the sample will bind to the matched T-cell. Contents of the reaction is analyzed using fluorescence flow cytometry, to determine, quantify and/or isolate those T-cells having a MHC tetramer, oligomer or multimer bound thereto. MHC-binding peptides are found in those tetramers, oligomers or multimers that are recognized by T-cells (See U.S. Pat. No. 5,635,363, which is incorporated herein by reference in its entirety).

An MHC monomer can further contain a peptide sequence engineered into the class I component of the monomer, for example, a signal sequence containing a biotinylation site for the BirA enzyme; and can contain a detectable label. The term "MHC multimer" or "multimeric MHC monomer or modified MHC monomer complex" is used herein to refer to a complex containing two or more MHC monomers, usually bound together via a multivalent entity. An MHC multimer can comprise an MHC dimer, MHC trimer, MHC tetramer, and the like (see, for example, U.S. Pat. No. 5,635,363, which is incorporated herein by reference). The MHC monomers in an MHC multimer can also be linked directly, for example, through a disulfide bond, or indirectly, for example, through a specific binding pair, and also can be associated through a specific interaction between secondary or tertiary structures of the monomers, such as a leucine zipper, which can be engineered, for example, into a MHC class I molecule component of the monomers. MHC tetramers are complexes of four MHC monomers, which are associated with a specific peptide antigen and contain a fluorochrome (U.S. Pat. No. 5,635,363).

MHC class I monomers have been prepared by substituting the transmembrane and cytoplasmic domains of the heavy chain with a peptide sequence that can be biotinylated, and MHC class I tetramers have been formed by contacting such monomers with streptavidin, which can bind four biotin moieties (see, for example, Altman et al., *Science* 274:94-96, 1996; Ogg and McMichael, *Curr. Opin. Immunol.* 10:393-396, 1998, each of which is incorporated herein by reference; see, also, U.S. Pat. No. 5,635,363), and are commercially available (Immunomics/Beckman Coulter, Inc.).

MHC tetramers have been prepared using MHC class 1 molecules, including mutated class IA HLA molecules, including HLA-A*0201, HLA-B*3501, HLA-A*1101, HLA-B*0801, and HLA-B*2705 to minimize binding of the HLA molecules to cell surface CD8 (Ogg and McMichael, supra, 1998). The designation "m" is used to indicate that the class IA molecule is a mutant; for example, HLA-A*0201m is generated from HLA-A*0201 by introducing an A245V substitution (see, for example, Bodinier et al., *Nat. Med.* 6:707-710, 2000). MHC tetramers containing mutated HLA molecules have a greatly diminished binding to the general population of CD8 cells, but retain peptide-specific binding, thus facilitating accurate discrimination of rare, specific T cells (less than 1% of CD8+; Altman et al., supra, 1996). For example, MHC tetramers composed of four HLA-A*0201 MHC class IA molecules, each bound to a specific peptide and conjugated with phycoerythrin (PE), have been prepared ("ITAG™ MHC Tetramer"); Immunomics/Beckman Coulter, Inc.). The HLA-A0201 allele is found in about 40% to 50% of the global population, and has been modified to minimize CD8 mediated binding (Bodinier et al., *Nat. Med.* 6:707-710, 2000, which is incorporated herein by reference). These complexes bind to a distinct set of T cell receptors (TCRs) on a subset of CD8+ T cells (McMichael and O'Callaghan, *J. Exp. Med.* 187:1367-1371, 1998, which is incorporated herein by reference). The ITAG™ MHC Tetramer complexes, for example, recognize human CD8+ T cells that are specific for the particular peptide and HLA molecule in the complex. Since specific binding does not depend on a functional pathway, the population identified by these tetramers includes all specific CD8+ cells, regardless of functional status.

The monomers of an MHC tetramer or other MHC multimer can be operatively linked together, covalently or non-covalently, and directly through a physical association or chemical bond or indirectly through the use of a specific binding pair or by attachment to a multivalent entity through the use of a specific binding pair. Alternatively, the monomers of an MHC multimer can be operatively linked to a multivalent entity containing multiple specific attachment sites for MHC monomers. As used herein, the term "operatively linked" or "operatively associated" means that a first molecule and at least a second molecule are joined together, covalently or non-covalently, such that each molecule substantially maintains its original or natural function. For example, where two or more MHC monomers, each of which can specifically bind a peptide antigen, are operatively linked to form an MHC multimer, each of the two or more MHC monomers in the MHC multimer maintains its ability to specifically bind the peptide antigen. Any means can be used for operatively linking the monomers, provided it does not substantially reduce or inhibit the ability of an MHC multimer to present an antigenic peptide to a T cell. Generally, the MHC monomers are linked together or to a multimeric moiety through the heavy chain component of the monomers. Thus, the monomers can be linked, for example, through an interchain peptide bond formed between reactive side groups of the amino acids comprising the heavy chains, through interchain disulfide bonds formed between cysteine residues in the heavy chains, or through any other type of bond that can generally be formed between the chemical groups represented by the amino acid side chains. A convenient means for operatively linking the monomers of an MHC multimer to a multivalent entity utilizes specific attachment sites that are each part of a binding pair. Where the MHC multimer is formed by attachment of the MHC monomers to a multimeric moiety, the monomers and the multivalent entity each provide one of the specific attachment sites that make up a binding pair.

For example, the heavy chains of the monomers can be biotinylated and formed into tetramers by chemical coupling to streptavidin, which naturally has 4 biotin-binding sites (FIG. 1). As used herein, the term "specific binding pair" refers to two molecules that can specifically interact with each other. The two molecules of a specific binding pair can be referred to as "members of a specific binding pair" or as "binding partners." A specific binding pairs is selected such that the interaction is stable under conditions generally used to perform an immunoassay. Numerous specific binding pairs are well known in the art and include, for example, an antibody that specifically interacts with an epitope and the epitope, for example, an anti-FLAG antibody and a FLAG peptide (Hopp et al., *BioTechnology* 6:1204 (1988); U.S. Pat. No. 5,011,912); glutathione and glutathione S-transferase (GST); a divalent metal ion such as nickel ion or cobalt ion and a polyhistidine peptide; or the like.

Biotin and streptavidin have been used to prepare MHC tetramers (streptavidin acting as a multivalent entity providing four specific attachment sites for biotin), and biotin and avidin also can be used. These specific binding pairs provide the advantage that a single avidin or streptavidin molecule can bind four biotin moieties, thus providing a convenient means to prepare MHC multimers, such as tetramers. Biotin can be bound chemically to the lysine residues of an MHC heavy chain or can be bound using an enzymatic reaction, wherein the heavy chain is modified to contain a peptide signal sequence comprising a biotinylation site for the enzyme BirA (see Altman et al., supra, 1996; Ogg and McMichael, supra, 1998). Alternatively, biotin can be linked to the θ2-microglobulin, which has fewer lysine residues than an MHC heavy chain, or can be linked to a mutant beta-2 microglobulin, which has been mutagenized to contain only a single accessible lysine residue.

In another embodiment, the multivalent entity can be a lipid surface, such as the surface of a liposome containing multiple attachment sites for the monomer and antibody. For example, the multivalent entity can be a liposome containing a lipid modified to bind to a histidine tag and at least one MHC monomer or modified MHC monomer and the antibody or antibody fragment, each having a carboxy terminal histidine tag, can be bound to the surface of the liposome via the histidine tag. For example, lipids containing Ni-iminodiacetic acid (Ni-IDA) or Ni-nitriloacetic acid (Ni-NTA) are binding partners for polyhistidine. An example of a lipid modified to bind to a histidine tag is 1,2-dioleoyl-sn-glycero-3-[N-95 amino-1-carboxypentyl) iminodiacetic acid) succinyl] with covalently attached nickel-chelating group, N",N"-bis[carboxymethyl]-L-lysine (nitriloacetic acid) (DOGS-Ni-NTA).

In another embodiment, the multivalent entity can be a yeast cell that expresses at least one, and preferably a plurality of the MHC monomers or modified MHC monomers, on the surface of the cell. An antibody can be attached to the yeast cell surface and a plurality of the antibodies are attached to (e.g. expressed on) the surface of the cell. Alternativley still, the multivalent entity can be a hybridoma and the MHC monomers or modified MHC monomers can be expressed on the surface of the hybridoma. In yet another embodiment, the non TCR-bearing target cell in the bridging complex can be a hybridoma that expresses on its cell surface a peptide for which the antibody is specific.

As used herein, the phrase "infection and/or exposure" includes such diverse conditions in a patient as mycobacterial infection or latency, response to anti mycobacterial vaccination, close contact with an individual having or suspected of having a mycobacterial infection or with a mycobacterium that causes disease in humans, especially in immunocompromised humans.

In the examples described herein granuloma associated lymphocytes were cultivated from lung biopsies of seven patients (See Table 1 below) that presented with a lung lesion of unknown etiology. Pathological diagnosis revealed tuberculosis in five patients and sarcoidosis- or rheumatoid arthritis-associated lesion of the lung in the two other patients. No viable mycobacteria could be isolated from sputum, broncholavage, or the biopsy itself.

TABLE 1

| Patient # | Sex/Age | MHC class I Haplotype | MHC class II Haplotype | Pathological Diagnosis | ESAT-6-reactivity |
|---|---|---|---|---|---|
| 1 | M/65 | A*26, A*29, B*45, B*52, Cw*06, Cw*12 | DRB1*15, DRB1*12, DRB3* DRB5*, DQB1*06, DQB1*03 | TB | + |
| 2 | M/63 | A*03, A*11, B*52, B*53, Cw*04, Cw*12 | DRB1*01, DRB1*11, DRB3*, DQB1*05, DQB1*03 | TB | + |
| 3 | M/37 | A*02, A*68, B*07, B*13, Cw*01, Cw*16 | DRB1*04, DRB1*15, DRB4*, DRB5*, DQB1*02, DQB1*06 | TB | + |
| 4 | F/41 | A*02, B*18, B*40 Cw*02, Cw*07 | DRB1*11, DRB1*16, DRB3*, DRB4*, DRB5* DQB1*03, DQB1*05 | TB | + |
| 5 | F/50 | A*02, B*44, Cw*05, Cw*16 | DRB1*04, DRB1*07, DRB4*, DQB1*03, | TB | + |
| 6 | F/67 | A*01, A*26, B*38, B*57, Cw*06, Cw*12 | DRB1*13, DRB1*07, DRB3*, DRB4*, DQB1*05, DQB1*03 | Rheumatoid arthritis | + |
| 7 | M/46 | A*02, B*18, B*44, Cw*05, Cw*07 | DRB1*04, DRB1*11, DRB3*, DRB4*, DQB1*03 | Sarcoidosis | + |

The aim of the experiments described herein was to ascertain the aspects involved in sustaining latency in the human lung by analyzing a) the quality of the T-cell responses, as determined by T-cell receptor (TCR) CDR3-spectratyping, b) the quantity of the T-cells in each TCR Vβ-family, as determined in flow cytometry analysis, and c) the function of the GALs, as defined by cytokine release assays.

CD4+ GALs and CD8+ GALs are oligoclonal, composed of highly expanded families and constitute an idiosyncratic population as compared to PBL. After magnetic bead sorting, CD4+ and CD8+ GAL populations were analyzed separately for the 'objective' structural composition of their TCR repertoire, defined by TCR CDR3 spectratyping complemented by a quantitative assessment of the TCR repertoire measured by flow cytometry. In FIG. 1 and FIG. 2A the 'TCR landscapes' have been plotted showing 24 Vβ families on the x-axis, the CDR3-lengths within the family as amino acid counts on the z-axis, and the percentage of CDR3 lengths within the lymphocyte population as a combination of the flow cytometrical enumeration and the area under the curve as determined by spectratyping on the y-axis.

An augmentation of a single CDR3 length within a Vβ family is commonly considered to be due to a clonal expansion of T lymphocytes that are possibly involved in a specific immune response. Each patient showed an individual, particular TCR Vβ profile for both the predominately oligoclonal CD4+ and CD8+ GAL populations. The Vβ families were not only oligoclonal, but few families of the altogether 24 Vβ families analyzed were expanded in the GAL populations. In some patients the T-cells belonging to a distinct oligoclonal or monoclonal Vβ family constituted a major fraction of the lymphocyte population. For example, in patient #1 Vβ 14 positive CD4+ lymphocytes and in patient #5 Vβ 7 positive T-cells accounted for 27% and 19%, respectively, of all CD4+ GAL. CDR3-spectratyping revealed these Vβ families to be characterized by an expansion of a single CDR3 length, thus indicating that these Vβ families were composed of a single T-cell clone. The TCRs (see Table 2 below) of these clones were sequenced using known methods in order to analyze their function in latent TB.

TABLE 2

| Patient/ GAL | End of V-Region (aa sequence) | CDR3 - Region (nucleotide and aa sequence) | Joining-Region (aa sequence) | | Reactivity against |
|---|---|---|---|---|---|
| #1 CD4+ Vb14+ | PSPNQTSLYFC (SEQ ID NO: 9) | gcagcagttctcgggccgggg cggtgggt-5' (SEQ ID NO: 10) ASSSRAGAVG (SEQ ID NO: 11) | EQFFGPGTRLTVLE (SEQ ID NO: 12) | BJ 2-1 | MTB |
| #1 CD8+ Vb3+ | ASTNQTSMYLC (SEQ ID NO: 13) | gccagcagtttaattcaagggg gc-5' (SEQ ID NO: 14) ASSLIQGG (SEQ ID NO: 15) | NQPQHFGDG (SEQ ID NO: 16) | BJ 1-5 | MTB |
| #5 CD4+ Vb7+ | SALYLC (SEQ ID NO: 17) | gccagcagccaagatacggc gggggccttccgg-5' (SEQ ID NO: 18) ASSQDTAGAFR (SEQ ID NO: 19) | ETQYFGPGTRL (SEQ ID NO: 20) | BJ 2-5 | ESAT-6$_{1-20}$ |

Major expansions could also be found in CD8+ GALs: monoclonal Vβ 3 positive T-cells in patient #1 (see Table 2 for TCR sequence), oligoclonal Vβ 17 positive lymphocytes in patient #3 and Vβ13 positive CD8+ GAL in patient #7 constituted up to 17%, 9%, and 12%, respectively of all CD8+ GAL.

No common expansion of a Vβ family could be identified in comparing the individual patients or HLA-type which might have indicated a preferential Vβ usage in human MTB containment.

As the panel of 24 Vβ-specific antibodies commercially available covers over 80%, but not the complete Vβ repertoire, it was not possible to identify all T-cells quantitatively that may be involved in controlling MTB. For example, in patient #1 20% of CD4+ and 55% of CD8+ GAL could not be quantitatively assessed for Vβ expression in flow cytometry. These T-cells, for which Vβ frequencies could not be measured, comprised only few additional Vβ families by molecular assessment, and thus may also have been clonally expanded.

In order to determine if the TCR repertoire of the lung is a mere mirror image of the peripheral blood or if the lung acquires a distinct TCR repertoire, both anatomical compartments of the test patients were analyzed (except PBL for patient #1 due to limited material). The data obtained for patient #2 (for both CD4+ and CD8+ T-cells) and for patient #5 (for total/unsorted PBL and GAL) is presented as a proof of principle in FIG. 3. By subtracting the GAL 'TCR landscape' from the 'TCR landscape' obtained for PBL, it was possible to visualize the percent differences, as shown in FIGS. 3A (molecular TCR-CDR3-analysis) and 3B (CDR3-analysis corrected by analysis of TCR Vβ frequencies). The perturbed landscapes indicate that the two compartments were indeed composed of a dissimilar TCR-repertoire and that individual TCR families are preferentially expanded within granuloma tissue. Had the repertoires been identical, a flat landscape would have resulted. GALs identified as characterized by an expanded Vβ family were selected for further study.

GALs Show a Th1/Tc1 Cytokine Secretion Pattern in Response to MTB

Before addressing the function of those GALs characterized by an expanded Vβ family, a more general approach was used to determine the function of the heterogenous CD4+ and CD8+ GAL populations in a cytokine release assay, using autologous macrophages as antigen presenting cells (APCs) that had been infected in vitro overnight with viable MTB. Of the five patients analyzed, CD4+ GALs of four patients produced IFN-γ at levels of 769 to >2000 pg/ml (FIG. 1B), while GM-CSF was measurable at levels of 38 to 2031 pg/ml in all three patients analyzed for the production of this cytokine (#3, #6, and #7; data not shown). Regarding CD8+ TCR+ GALs, two of three analyzed patients produced 614 and >2000 pg/ml of IFN-γ, respectively (FIG. 2B), and all three CD8+ GAL populations showed an immune response in respect to GM-CSF production with levels of 35 to 1262 pg/ml while IL-4 was not measurable in any patient (data not shown). Remarkably, even patients without TB-specific lesions in the biopsy (patients #6 and #7), but with a positive 'immunological diagnosis' on account of their ESAT-6 responsiveness (see below), were capable of mounting a strong cell-mediated immune response within 48 hours to MTB, as well. Of note, prior in vitro stimulation of the analyzed lymphocytes using MTB-antigens had not been done.

In patient #3 no IFN-γ or IL-4 was measurable as a response to naturally processed and presented MTB epitopes on autologous APCs. However, GALs of this patient were capable of producing substantial amounts of IFN-γ in response to MTB-derived peptides in a different experimental setting (See FIGS. 7 and 8), suggesting that these cells were functionally capable of secreting cytokines.

In order to confirm MHC-restriction, additional experiments were performed using blocking monoclonal antibodies (mAbs) directed against MHC class I or class II. Cytokine production was either partially or completely inhibited by mAbs directed against DR, DP, and DQ in the CD4+ GAL population (FIGS. 1A-C) (but not the CD8+ GAL population; (FIGS. 2A-C), indicating that MTB peptides were presented on MHC class II molecules. On the other hand, MHC class-I mAbs inhibited cytokine production partially or completely of the CD8+ TCR+ population (FIG. 2B) while showing no effect on CD4+ GALs (data not shown).

Preparation of Monomers

The Class I MHC in humans is located on chromosome 6 and has three loci, HLA-, HLA-B, and HLA-C. The first two loci have a large number of alleles encoding alloantigens. These are found to consist of a 44 Kd heavy chain subunit and a 12 Kd beta-2-microglobulin subunit which is common to all antigenic specificities. For example, soluble HLA-A2 can be purified after papain digestion of plasma membranes from the homozygous human lymphoblastoid cell line J-Y as described by Turner, M. J. et al., J. Biol. Chem. (1977) 252: 7555-7567. Papain cleaves the 44 Kd heavy chain close to the transmembrane region, yielding a molecule comprised of $\alpha_1$, $\alpha_2$, $\alpha_3$ domains and beta-2 microglobulin.

The MHC monomers can be isolated from appropriate cells or can be recombinantly produced, for example as described by Paul et al, Fundamental Immunology, 2d Ed., W. E. Paul, ed., Ravens Press N.Y. 1989, Chapters 16-18) and readily modified, as described below.

The term "isolated" as applied to MHC monomers herein refers to an MHC glycoprotein heavy chain of MHC class I, which is in other than its native state, for example, not associated with the cell membrane of a cell that normally expresses MHC. This term embraces a full length subunit chain, as well as a functional fragment of the MHC monomer. A functional fragment is one comprising an antigen binding site and sequences necessary for recognition by the appropriate T cell receptor. It typically comprises at least about 60-80%, typically 90-95% of the sequence of the full-length chain. As described herein, the "isolated" MHC subunit component may be recombinantly produced or solubilized from the appropriate cell source.

It is well known that native forms of "mature" MHC glycoprotein monomers will vary somewhat in length because of deletions, substitutions, and insertions or additions of one or more amino acids in the sequences. Thus, MHC monomers are subject to substantial natural modification, yet are still capable of retaining their functions. Modified protein chains can also be readily designed and manufactured utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

In general, modifications of the genes encoding the MHC monomer may be readily accomplished by a variety of well-known techniques, such as site-directed mutagenesis. The effect of any particular modification can be evaluated by routine screening in a suitable assay for the desired characteristic. For instance, a change in the immunological character of the subunit can be detected by competitive immunoassay with an appropriate antibody. The effect of a modification on the ability of the monomer to activate T cells can be tested using standard in vitro cellular assays or the methods described in the example section, below. Modifications of other properties such as redox or thermal stability, hydrophobicity, susceptibility to proteolysis, or the tendency to aggregate are all assayed according to standard techniques.

This invention provides amino acid sequence modification of MHC monomers prepared with various objectives in mind, including increasing the affinity of the subunit for antigenic peptides and/or T cell receptors, facilitating the stability, purification and preparation of the subunits. The monomers may also be modified to modify plasma half life, improve therapeutic efficacy, or to lessen the severity or occurrence of side effects during therapeutic use of complexes of the present invention. The amino acid sequence modifications of the subunits are usually predetermined variants not found in nature or naturally occurring alleles. The variants typically exhibit the same biological activity (for example, MHC-peptide binding) as the naturally occurring analogue.

Insertional modifications of the present invention are those in which one or more amino acid residues are introduced into a predetermined site in the MHC monomer and which displace the preexisting residues. For instance, insertional modifications can be fusions of heterologous proteins or polypeptides to the amino or carboxyl terminus of the subunits.

Other modifications, include fusions of the monomer with a heterologous signal sequence and fusions of the monomer to polypeptides having enhanced plasma half life (ordinarily>about 20 hours) such as immunoglobulin chains or fragments thereof as is known in the art.

Substitutional modifications are those in which at least one residue has been removed and a different residue inserted in its place. Nonnatural amino acid (i.e., amino acids not normally found in native proteins), as well as isosteric analogs (amino acid or otherwise) are also suitable for use in this invention.

Substantial changes in function or immunological identity are made by selecting substituting residues that differ in their effect on maintaining the structure of the polypeptide backbone (e.g., as a sheet or helical conformation), the charge or hydrophobicity of the molecule at the target site, or the bulk of the side chain. The substitutions which in general are expected to produce the greatest changes in function will be those in which (a) a hydrophilic residue, e.g., serine or threonine, is substituted for (or by) a hydrophobic residue, e.g. leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamine or aspartine; or (d) a residue having a bulky side chain, e.g., phenylalanine, is substituted for (or by) one not having a side chain, e.g., glycine.

Substitutional modifications of the monomers also include those where functionally homologous (having at least about 70% homology) domains of other proteins are substituted by routine methods for one or more of the MHC subunit domains. Particularly preferred proteins for this purpose are domains from other species, such as murine species.

Another class of modifications are deletional modifications. Deletions are characterized by the removal of one or more amino acid residues from the MHC monomer sequence. Typically, the transmembrane and cytoplasmic domains are deleted. Deletions of cysteine or other labile residues also may be desirable, for example in increasing the oxidative stability of the MHC complex. Deletion or substitution of potential proteolysis sites, e.g., ArgArg, is accomplished by deleting one of the basic residues or substituting one by glutaminyl or histidyl residues.

A preferred class of substitutional or deletional modifications comprises those involving the transmembrane region of the subunit. Transmembrane regions of MHC monomers are highly hydrophobic or lipophilic domains that are the proper size to span the lipid bilayer of the cellular membrane. They are believed to anchor the MHC molecule in the cell membrane. Inactivation of the transmembrane domain, typically by deletion or substitution of transmembrane domain hydroxylation residues, will facilitate recovery and formulation by reducing its cellular or membrane lipid affinity and improving its aqueous solubility. Alternatively, the transmembrane and cytoplasmic domains can be deleted to avoid the introduction of potentially immunogenic epitopes. Inactivation of the membrane binding function is accomplished by deletion of sufficient residues to produce a substantially hydrophilic hydropathy profile at this site or by substitution with heterologous residues which accomplish the same result.

A principal advantage of the transmembrane-inactivated MHC monomer is that it may be secreted into the culture medium of recombinant hosts. This variant is soluble in body fluids such as blood and does not have an appreciable affinity for cell membrane lipids, thus considerably simplifying its recovery from recombinant cell culture. Typically, modified MHC monomers of this invention will not have a functional transmembrane domain and preferably will not have a functional cytoplasmic sequence. Such modified MHC monomers will consist essentially of the effective portion of the extracellular domain of the MHC monomer. In some circumstances, the monomer comprises sequences from the transmembrane region (up to about 10 amino acids), so long as solubility is not significantly affected.

For example, the transmembrane domain may be substituted by any amino acid sequence, e.g., a random or predetermined sequence of about 5 to 50 serine, threonine, lysine, arginine, glutamine, aspartic acid and like hydrophilic residues, which altogether exhibit a hydrophilic hydropathy profile. Like the deletional (truncated) monomer, these monomers are secreted into the culture medium of recombinant hosts.

Glycosylation variants are included within the scope of this invention. They include variants completely lacking in glycosylation (unglycosylated) and variants having at least one less glycosylated site than the native form (deglycosylated) as well as variants in which the glycosylation has been changed. Included are deglycosylated and unglycosylated amino acid sequence variants, deglycosylated and unglycosylated subunits having the native, unmodified amino acid sequence. For example, substitutional or deletional mutagenesis is employed to eliminate the N- or O-linked glycosylation sites of the subunit, e.g., the asparagine residue is deleted or substituted for by another basic residue such as lysine or histidine. Alternatively, flanking residues making up the glycosylation site are substituted or deleted, even though the asparagine residues remain unchanged, in order to prevent glycosylation by eliminating the glycosylation recognition site. Additionally, unglycosylated MHC monomers which have the amino acid sequence of the native monomers are produced in recombinant prokaryotic cell culture because prokaryotes are incapable of introducing glycosylation into polypeptides.

Glycosylation variants are conveniently produced by selecting appropriate host cells or by in vitro methods. Yeast, for example, introduce glycosylation which varies significantly from that of mammalian systems. Similarly, mammalian cells having a different species (e.g., hamster, murine, insect, porcine, bovine or ovine) or tissue origin (e.g., lung, liver, lymphoid, mesenchymal or epidermal) than the MHC source are routinely screened for the ability to introduce variant glycosylation as characterized for example by elevated levels of mannose or variant ratios of mannose, fucose, sialic acid, and other sugars typically found in mammalian glycoproteins. In vitro processing of the subunit typically is accomplished by enzymatic hydrolysis, e.g., neuraminidase digestion.

MHC glycoproteins suitable for use in the present invention have been isolated from a multiplicity of cells using a variety of techniques including solubilization by treatment with papain, by treatment with 3M KCl, and by treatment with detergent. For example, detergent extraction of Class I protein followed by affinity purification can be used. Detergent can then be removed by dialysis or selective binding beads. The molecules can be obtained by isolation from any MHC I bearing cell, for example from an individual suffering from a targeted cancer or viral disease.

Isolation of individual heavy chain from the isolated MHC glycoproteins is easily achieved using standard techniques known to those skilled in the art. For example, the heavy chain can be separated using SDS/PAGE and electroelution of the heavy chain from the gel (see, e.g., Dornmair et al., supra and Hunkapiller, et al., Methods in Enzymol. 91:227-236 (1983). Separate subunits from MHC I molecules are also isolated using SDS/PAGE followed by electroelution as described in Gorga et al. J. Biol. Chem. 262:16087-16094 (1987) and Dornmair et al. Cold Spring Harbor Symp. Quant. Biol. 54:409-416 (1989) Those of skill will recognize that a number of other standard methods of separating molecules can be used, such as ion exchange chromatography, size exclusion chromatography or affinity chromatography.

Alternatively, the amino acid sequences of a number of Class I and Class II proteins are known, and the genes have been cloned, therefore, the MHC monomers can be expressed using recombinant methods. These techniques allow a number of modifications of the MHC monomers as described above. For instance, recombinant techniques provide methods for carboxy terminal truncation, which deletes the hydrophobic transmembrane domain. The carboxy termini can also be arbitrarily chosen to facilitate the conjugation of ligands or labels, for example, by introducing cysteine and/or lysine residues into the molecule. The synthetic gene will typically include restriction sites to aid insertion into expression vectors and manipulation of the gene sequence. The genes encoding the appropriate monomers are then inserted into expression vectors, expressed in an appropriate host, such as E. coli, yeast, insect, or other suitable cells, and the recombinant proteins are obtained.

As the availability of the gene permits ready manipulation of the sequence, a second generation of construction includes chimeric constructs. For example, the $\alpha_1$, $\alpha_2$, $\alpha_3$, domains of the class I heavy chain can be linked, typically by the $\alpha_3$ domain of Class I, with beta-2 microglobulin and coexpressed to stabilize the complex. The transmembrane and intracellular domains of the Class I or Class II gene can optionally also be included.

Construction of expression vectors and recombinant production from the appropriate DNA sequences are performed by methods known in the art. Standard techniques are used for DNA and RNA isolation, amplification, and cloning. Generally enzymatic reactions involving DNA ligase, DNA polymerase, restriction endonucleases, and the like, are performed according to the manufacturer's specifications. These techniques and various other techniques are generally performed according to Sambrook et al., Molecular Cloning—A Laboratory Manual, Cold Spring Harbor Laboratory, Cold Spring Harbor, N.Y., 1989. The procedures therein are believed to be well known in the art.

Expression can be in procaryotic or eucaryotic systems. Suitable eucaryotic systems include yeast, plant and insect systems, such as the Drosophila expression vectors under an inducible promoter. Procaryotes most frequently are represented by various strains of E. coli. However, other microbial strains may also be used, such as bacilli, for example Bacillus subtilis, various species of Pseudomonas, or other bacterial strains. In such procaryotic systems, plasmid vectors which contain replication sites and control sequences derived from a species compatible with the host are used. For example, E. coli is typically transformed using derivatives of pBR322, a plasmid derived from an E. coli species by Bolivar et al., Gene (1977) 2:95. Commonly used procaryotic control sequences, which are defined herein to include promoters for transcription initiation, optionally with an operator, along with ribosome binding site sequences, including such commonly used promoters as the β-lactamase (penicillinase) and lactose (lac) promoter systems (Change et al., Nature (1977) 198:1056) and the tryptophan (trp) promoter system (Goeddel et al., Nucleic Acids Res. (1980) 8:4057) and the lambda-derived $P_L$ promoter and N-gene ribosome binding site (Shimatake et al., Nature (1981) 292:128). Any available promoter system compatible with procaryotes can be used.

The expression systems useful in the eucaryotic hosts comprise promoters derived from appropriate eucaryotic genes. A class of promoters useful in yeast, for example, include promoters for synthesis of glycolytic enzymes, including those for 3-phosphoglycerate kinase (Hitzeman, et al., J. Biol. Chem. (1980) 255:2073). Other promoters include, for example, those from the enolase gene (Holland, M. J., et al. J. Biol. Chem. (1981) 256:1385) or the Leu2 gene obtained from YEp13 (Broach, J., et al., Gene (1978) 8:121). A Drosophila expression system under an inducible promoter (Invitrogen, San Diego, Calif.) can also be used.

Suitable mammalian promoters include the early and late promoters from SV40 (Fiers, et al., Nature (1978) 273:113) or other viral promoters such as those derived from polyoma, adenovirus II, bovine papilloma virus or avian sarcoma viruses. Suitable viral and mammalian enhancers are cited above.

The expression system is constructed from the foregoing control elements operably linked to the MHC sequences using standard methods, employing standard ligation and restriction techniques which are well understood in the art. Isolated plasmids, DNA sequences, or synthesized oligonucleotides are cleaved, tailored, and religated in the form desired.

Site-specific DNA cleavage is performed by treatment with the suitable restriction enzyme (or enzymes) under conditions which are generally understood in the art, and the particulars of which are specified by the manufacturer of these commercially available restriction enzymes. In general, about 1 µg of plasmid or DNA sequence is cleaved by one unit of enzyme in about 20 µl of buffer solution; an excess of restriction enzyme may be used to insure complete digestion of the DNA substrate. After each incubation, protein is removed by extraction with phenol/chloroform, and may be followed by ether extraction, and the nucleic acid recovered from aqueous fractions by precipitation with ethanol followed by running over a SEPHADEX™ G-50 spin column. If desired, size separation of the cleaved epitopes may be performed.

Restriction cleaved epitopes may be blunt ended by treating with the large epitope of E. coli DNA polymerase I (Klenow) in the presence of the four deoxynucleotide triphosphates (dNTPs) After treatment with Klenow, the mixture is extracted with phenol/chloroform and ethanol precipitated followed by running over a SEPHADEX™ G-50 spin column.

Synthetic oligonucleotides are prepared using commercially available automated oligonucleotide synthesizers. In the proteins of the invention, however, a synthetic gene is conveniently employed. The gene design can include restriction sites which permit easy manipulation of the gene to replace coding sequence portions with these encoding analogs.

Correct ligations for plasmid construction can be confirmed by first transforming *E. coli* strain MM294 obtained from *E. coli* Genetic Stock Center, CGSC #6135, or other suitable host, with the ligation mixture. Successful transformants can be selected by ampicillin, tetracycline or other antibiotic resistance or by using other markers depending on the mode of plasmid construction, as is understood in the art. Plasmid from the transformants are then prepared, optionally following chloramphenicol amplification. The isolated DNA is analyzed by restriction and/or sequenced by the dideoxy method of Sanger, F., et al., Proc. Natl. Acad. Sci. USA (1977) 74:5463 as further described by Messing, et al., Nucleic Acids Res. (1981) 9:309, or by the method of Maxam, et al., Methods in Enzymology (1980) 65:499.

The constructed vector is then transformed into a suitable host for production of the protein. Depending on the host cell used, transformation is done using standard techniques appropriate to such cells. The calcium treatment employing calcium chloride, as described by Cohen, S. N., Proc. Natl. Acad. Sci. USA (1972) 69:2110, or the RbCl method described in Maniatis, et al., Molecular Cloning: A Laboratory Manual (1982) Cold Spring Harbor Press, p. 254 is used for procaryotes or other cells which contain substantial cell wall barriers. For mammalian cells without such cell walls, the calcium phosphate precipitation method of Graham and van der Eb, Virology (1978) 52:546 or electroporation is preferred. Transformations into yeast are carried out according to the method of Van Solingen, P., et al., J. Bacter. (1977) 130:946 and Hsiao, C. L., et al., Proc. Natl. Acad. Sci. USA (1979) 76:3829.

The transformed cells are then cultured under conditions favoring expression of the MHC sequence and the recombinantly produced protein recovered from the culture.

MHC-Binding Peptides

It is believed that the presentation of antigen by the MHC glycoprotein on the surface of antigen-presenting cells (APCs) occurs subsequent to the hydrolysis of antigenic proteins into smaller peptide units. The location of these smaller segments within the antigenic protein can be determined empirically. These MHC-binding peptides are thought to be about 8 to about 10, possibly about 8 to about 11, or about 8 to about 12 residues in length, and contain both the agretope (recognized by the MHC molecule) and the epitope (recognized by T cell receptor on the T cell). The epitope is a linear sequence of about 8 to about 10, possibly about 8 to about 11, or about 8 to about 12 residues in length, that is recognized by the antigen-specific T cell receptor. The agretope is a continuous or noncontiguous sequence that is responsible for binding of the peptide with the MHC glycoproteins. The invention provides systems, kits, and assays for evaluating putative MHC-binding peptides to determine whether such fragments can be incorporated into a ternary complex with an MHC monomer or modified MHC monomer.

It is presently preferred that the monomers are biotinylated for ease of formation of a tetramer or other multimer. Multimers of exchanged monomers are preferably tagged with a moiety than can be used to attach the tagged monomers to a multivalent core entity. For example, if the monomers used in the assay can be tagged with biotin, the multimer can then be formed by binding of the monomers to an avidinated multivalent entity, such as a cell surface, a liposome, and the like. Preferably, the multimer is formed by binding of the biotinylated exchanged monomers to streptavidin or avidin to form tetramers, which are detectably labeled with PE. Determination of tetramer "staining" of the TCR-bearing cells is readily then determined using flow cytometry, as is illustrated in the Examples herein.

CD4+ GALs and CD8+ GALs Characterized by an Expanded Vβ Family are the Major IFN-γ Producers In order to investigate if an expansion of a Vβ family within the CD4+ and the CD8+ GAL population is indeed indicative of a major functional role in disease combat, the GALs were sorted according to their expanded Vβ family and analyzed in cytokine release assays. As elaborated above, CDR3 spectratyping coupled with flow cytometry allowed us to recognize Vβ 9 and Vβ 14 in patient #1, Vβ 8 and Vβ 9 in patient #2, and Vβ 7 in patient #5 as the major represented Vβ families in the CD4+ GAL population, as well as Vβ 3 in patient #1 in CD8+ GALs. These patients had a positive pathological diagnosis for TB. We sorted and exposed T-cells, expressing the relevant Vβ families, to MTB-infected macrophages for 48 hours, as described above. The production of IFN-γ by these T-cells resulted in much higher concentrations (ranging from 1300-9955 pg/ml for CD4+ GALs, 1185 pg/ml for CD8+ GALs; FIGS. 5A-C) than were produced by the whole population of GALs at comparative cell counts. As expected, mAbs directed against MHC class I inhibited cytokine production of Vβ 3+ CD8+ GALs. In CD4+, Vβ-sorted GALs, IFN-γ production was blocked either by DR, DP, or DQ mAbs, suggesting that the sorted T-cells were restricted to a single MHC class II allele.

CD4+ GALs, Belonging to a Certain Expanded Vβ Family, Recognize ESAT-6$_{1-20}$

To determine antigen-specificity of the sorted CD4+ GALs, analysis was made of the Vβ-sorted T-cells' ability to recognize MTB derived DR-binding peptides ESAT-6$_{1-20}$ and ESAT-6$_{72-95}$. In these studies, Vβ-sorted GALs recognized ESAT-6$_{1-20}$ and produced IFN-γ in patients #1, #2, and #5; whereas ESAT-6$_{72-95}$ induced an IFN-γ production rose above background levels only in Vβ 7+ GALs of patient #5 (FIG. 6E). An increase of peptide concentration evoked a stronger cytokine response, as shown in FIGS. 6B, D, and F, but at the highest peptide concentration tested results varied, ranging from a further increase in patient #2 to suppression of IFN-γ in patient #5. When analyzing the corresponding Vβ depleted GAL population in the identical experimental setting, it was observed that these GALs did not recognize the ESAT-6$_{1-20}$ peptide, as no IFN-γ production was measurable above background levels (Vβ 9-negative GALs in patient #1: 4 pg/ml; Vβ 9-negative GAL in patient #2: below detection levels; Vβ 7-negative GALs in patient #5: 45 pg/ml; data not shown in FIG. 6A). Recognition of ESAT-6$_{1-20}$ was, therefore, restricted to a single Vβ family in these three patients or even a single Vβ 7+ T-cell clone in patient #5.

In addition, the ESAT-6-specific immune response was investigated in patients without pathological lesions particular of TB in the biopsy. Recognition of ESAT-6$_{1-20}$ in both patients led to production of substantial amounts of IFN-γ and GM-CSF, which could be blocked by mAbs directed against HLA-DR (FIGS. 8A-C). IL-4 production was not detectable (data not shown). As was seen in the other patients, ESAT-$6_{72-95}$ induced no measurable cytokine production, even of IL-4.

MTB Derived HLA A2-Binding Peptides Evoke a Tc1 Cytokine Response in CD8+ GALs

Recognition of antigenic peptides was investigated in the CD8+ GAL population of HLA A2+ patients (Table 1, FIGS. 8A-C). MTB-derived HLA A2-binding peptides Ag85A$_{48-56}$, Ag85A$_{242-250}$, Ag85B$_{143-152}$, Ag85B$_{199-207}$, and 19-kDa Ag$_{88-97}$, respectively, were loaded on T2 cells, CD8+ GALs added, and the in vitro cytokine production was measured after 48 hours of incubation. A melanoma-derived Gp100 peptide was used as a negative control.

While 19-kDa Ag$_{88-97}$ evoked a moderate immune response, the most immunogenic peptides proved to be Ag85A$_{242-250}$ and Ag85B$_{199-207}$, as determined by IFN-γ and GM-CSF production. The other peptides tested did not elicit a much higher cytokine production than the control peptide gp100 in any patient. IL-4 was not detectable in any case (data not shown). In addition, GALs derived from patient #3 were analyzed for reactivity to three candidate A2-binding target peptides provided from ESAT-6. These GALs preferentially recognized ESAT-$6_{28-36}$ in a MHC class I restricted manner and produced substantial amounts of IFN-γ and GM-CSF (FIGS. 9A-B), ESAT-$6_{17-25}$ and ESAT-$6_{62-70}$ elicited minor cytokine production.

As differences were detected between the Vβ-repertoire of GAL and PBL, the magnitude of Tet-Ag85B+ GALs in a flow cytometrical analysis was determined and compared with the frequencies those found in PBL (as exemplified in patient #7). Latent CMV infection was expected to be present in most patients, so the HLA-A2-binding pp65 peptide was used as a positive control and reference point. Frequencies for both the Tet-Ag85B+ and Tet-CMVpp65+ T-cells were similar in the GAL population and in PBLs, ranging between the high frequencies of tetramer-positive T-cells found in acute viral infections and the low frequencies found in many malignancies. The similar quantities found in these two compartments could be interpreted as somewhat in disagreement with the distinct quantitative differences seen in comparing the TCR-landscapes. However, CDR3-spectratyping revealed that the Tet-Ag85B+ GAL population consisted of T-cells belonging to a broad spectrum of different Vβ families and thus of diverse T-cell clones (data not shown). Due to limited availability of PBLs the molecular TCR-composition in GALs was not compared with that in PBLs. These data indicate that tetramer staining provides information pertaining to the enumeration of MHC-restricted and antigen-specific T-cells in different anatomic compartments, but it may be supplemented by qualitatively comparing PBL and tissue-derived lymphocytes on a clonal level, e.g. using TCR-CDR3 analysis.

Confocal Laser Scanning Microscopy (CLSM) Offers a New View of CD8+ GALs In Situ In patients #3 and #4, who presented with TB-specific lesions, antigen-specific CD8+ GALs were visualized in situ by staining lung sections with HLA A2 tetramers for Ag85B$_{199-207}$ and 19-kDa Ag$_{88-97}$. TCR bound tetramers appeared red in CLSM while mAbs directed against CD8α were FITC-labeled and appeared green. As previously observed in murine lymphoid tissue, tetramer staining visualized TCRs that seemed clustered at one (or few) pole(s) of the T-cell, giving an impression of a bright red dot or dots on the circular cell, while CD8 seemed more equally distributed, giving the cell a homogenous, annular appearance. Upon double expression, the red and green resulted in an orange-yellow coloring of the cells. Staining with gp100-MHC tetramers, as a negative control, led to mere background staining. The tetramer-positive cells were focused to several different loci within the lung sections.

The immunological situation in latent tuberculosis has been difficult to understand and research due to lack of a suitable animal model for this state of disease. Moreover, the results obtained from the analysis of PBL in humans may not necessarily reflect the immune response at the site of infection itself. Several studies report a prominence of Th2-type cytokines, such as IL-10, in PBL. On the other hand, T-cells from other compartments in patients with active TB, such as pleural effusions or T-cells isolated by bronchoalveolar lavage, showed a marked IFN-γ and/or proliferative response that was lower, or even absent, in PBL of the same analyzed patients. This phenomenon may be due to sequestration of distinctive MTB-reactive T-cells to the site of infection, possibly on account of particular chemokine receptors, such as CCR2 or CCR5. Hence, a closer look at the immunological events in the lung tissue itself may lead to better comprehension of protective immunity to MTB.

The fine specificity of TCR antigen recognition resides mostly in the complementary-determining region 3 of the TCR Vα and Vβ chain. The clonal expansion of antigen-specific T-cells in response to antigen is reflected as a single or a few overrepresented CDR3-peak(s) within a Vβ family in CDR3-spectratyping. Ultimately, this clonal expansion of T-cells can translate into an augmentation of the relevant Vβ family within the Vβ repertoire, as described for both viral and bacterial infections isolated from human lung tissue were characterized by oligoclonal or monoclonal expansions of individual Vβ families. These Vβ expansions in GAL were not observable in PBL of the patients testing, showing that the MTB-reactive T-cells had indeed been sequestered to the lung. A comparable compartmentalization has been reported in a study on active human TB, in which the Vβ repertoire of lymphocytes from pleural fluid differed from that found in PBL.

Expanded GALs readily recognized MTB-infected autologous macrophages and produced IFN-γ, a cytokine well-established in contributing to immunity against MTB. This strong production of IFN-γ by CD4+ and CD8+ GALs in the absence of measurable IL-4 in patients with latent TB indicates that in humans a cell-mediated immune response by lung tissue-residing lymphocytes is indeed involved in containing MTB.

The frequencies of expanded, MTB-specific T-cell clones were unexpectedly high in the lung tissue (reaching up to 27% of CD4+ GAL in an individual patient) as compared to previously published findings for CD8+ Tet-19 kD Ag+ reactive T-cells in PBL of patients with active TB (approximately 2% of CD8+ PBL) or in respect to tissue residing lymphocytes, as seen for Melan-A/MART1$_{27-35}$-specific tumor infiltrating T-cells (5.68% of TILs). This frequency increase for latent TB seems even more pronounced, considering that tetramer analysis or limiting dilution assays used in these studies may reflect frequencies for antigen-specific T-cells of diverse clones, as demonstrated in FIGS. 9A-B, while single clone expansions were found in GALs. On the other hand, frequencies similar to those in GALs have been detected by others when analyzing organ-specific tetramer-reactive T-cell responses in acute murine listeriosis. In listeriosis, these frequencies declined to below 8% after successful resolution of the disease. In latent TB frequencies may be expected to remain elevated as disease is not essentially cleared due to the persistence of viable MTB inside macrophages for many years. Interestingly, MTB-reactive GALs were also present in lung tissue that was free of definite TB-specific lesions, as seen in patients #6 and #7.

For three patients diagnosed with latent TB, the antigen-specificity of those cells in the CD4+ GAL population that comprised the major expanded Vβ family was defined: Vβ 9 in patient #1 and #2 and Vβ 7 in patient #5. These GALs produced increased amounts of IFN-γ in response to MTB as compared to the whole CD4+ GAL population and were all ESAT-6-specific. In patient #5, for example, a single Vβ 7 positive T-cell clone (Table 2) made up 19% of lung-residing lymphocytes that were dedicated to the recognition of an ESAT-6 epitope. The early secreted antigenic target 6 (ESAT-6) has been implicated to be sensitive and specific for the detection of active or latent MTB infection in humans due to its absence of expression in BCG and most environmental mycobacterial species. Moreover these expanded lymphocytes were the sole CD4+ T-cells that recognized the peptide derived from ESAT-$6_{1-20}$ in the whole GAL population. This finding indicates a highly focused immune response to select MTB antigens in the lung. These data show that successful MTB containment, may be highly focused and restricted to a few TCR-clonotypes. All expanded Vβ families could not be linked to the recognition of MTB associated epitopes. The immunological control of other recurring or chronic infections of the lung, such as CMV, may likely require the presence of adequately expanded T-cells, as well.

The clinical implications of these data are important. Given the observations that each organ may be equipped with a different immune response to the same pathogen in terms of quality or quantity, the understanding of the immunological situation in the lung in human TB is fundamental for the development of effective MTB vaccine strategies. An ideal vaccine should be broadly applicable and effective. Efficacy may be strongly enhanced by including the ESAT-6 Ag, as the ESAT-$6_{1-20}$ peptide-specific CD4+ lymphocytes were among the main performers in maintaining latency at the primary site of infection in the TB patients examined in this example.

ESAT-6 may certainly be a crucial antigen in the immune response to MTB and studies advocate or have already successfully implemented this antigen in vaccination in the murine model.

However, data on the immunodominant epitope(s) (potentially important for both efficacy and applicability) differ worldwide. The results obtained in the examples presented herein, which included the peptides ESAT-$6_{1-20}$ and ESAT-$6_{72-95}$, covering the aminoterminal (N-terminal) and the carboxyterminal (C-terminal) part of the antigen, and were performed on GALs of Caucasian German patients. Based on this population, the results indicate that the immunodominant epitopes reside in the N-terminal part of ESAT-6 and can be presented on various HLA DR-molecules, thereby being in accord with a study on PBL by Ulrich et al. involving German patients as well as with a report of the same group on recent PPD converters from Boston, Mass. On the other hand, studies from other regions of the world advocate other ESAT-6 epitopes: Ethiopian patients preferentially recognized the central part of the antigen (aa 42-75), while Kuwaiti and Danish patients most frequently recognized the C-terminal region (aa 72-95). As discussed by both Mustafa et al. and Ravn et al., this phenomenon may result from diversities in the genetic HLA-makeup of different ethnic groups. Similar observations have been made in regard to the ESAT-6 recall responses of genetically different mice and this genetic factor should also be taken into consideration in the development of novel TB vaccinations and/or detection systems.

Substantial evidence exists for the critical role of CD8+ lymphocytes in tuberculosis. Clonal expansions of MTB-specific CD8+ GALs were also observed in lung tissue in the studies included in the Examples herein, for example, the Vβ 3 positive T-cell clone that constituted 17% of the CD8+ GAL population in patient #1. Therefore, studies were conducted to determine the major antigenic targets of CD8+ GALs by screening a panel of HLA-A2-presented peptides derived from the secreted Ags 85A, 85B and ESAT-6 and the 19-kDa lipoprotein that had been reported in literature as key targets. In these studies of latent TB, a preferential recognition of Ag85$A_{242-250}$ and Ag85$B_{199-207}$ as well as ESAT-$6_{28-36}$ was observed, and a moderate reaction to 19-kDaAg$_{88-97}$. By contrast, Ag85$A_{48-56}$ and Ag85$B_{143-152}$ elicited little response, if any at all. Whether this observation is a general trend for lung-derived CD8+ T-cells or a distinct feature for the individual patient may need to be further studied in a larger cohort. The major importance of these data is, however, that Ag 85A- and 85B-specific as well as ESAT-6 and 19-kDaAg-specific CD8+ T-cells are indeed present as functional immunocytes in the human lung (and not only in peripheral blood) and that these antigens are involved in the maintenance of latency. To visualize these cells in ex vivo, in situ tetramer staining followed by CLSM was performed. This procedure achieved an unprecedented exposition of both Ag85b- and 19 kDaAg-specific CD8+ T-cells in human lung tissue.

In summary, we demonstrate that in human latent TB CD4+ and CD8+ MTB-reactive lymphocytes are present, highly expanded and functional in the lung tissue. In addition to CD8+ tetramer in situ staining, CD4+ and ESAT-6-reactive T-cells could also be directly visualized in granuloma tissue implementing tetramer in situ staining. CDR3 spectratyping coupled with flow cytometrical Vβ analysis is a powerful tool in their identification and has enabled us to understand that a focused lymphocyte population distinct from PBL does govern latency. Key targets are particular peptides of secreted antigens like ESAT-6 and Ags 85A and 85B. In the future, integration of these antigen into a vaccine may prove crucial for establishing protective immunity to MTB.

Thus, the ex vivo identification of anti-MTB reactive CD4+ or CD8+ T-cells is desirable in order to provide biologically meaningful surrogate markers for gauging the efficacy of novel vaccines, for testing latent MTB infections, to test for eradication of MTB in the course of already established and novel treatment strategies and potentially to define the threshold required to maintain 'protective immunity'. We report here the identification of HLA-DR4-restricted antigen specific CD4+ T-cells directed against antigens shared among MTB and mycobacteria other than tuberculosis (MOTT), i.e. the 19 kDa lipoprotein, the AG85b or the ESAT-6 protein which is exclusively present in MTB.

The invention is further illustrated by the following non-limiting examples.

Example 1

Materials and Methods

Patients diagnosed with pulmonary tuberculosis (five of seven) were recruited from the university hospital Heidelberg. Tuberculosis was diagnosed by typical lesions y X ray and PCR-based MTB-identification. Lung tissue has been obtained by surgery in order to rule out a malignant lesion. If granulomatous tissue has been identified by HE-staining, freshly isolated lung tissue has been placed in RPMI medium, supplemented with 10% FCS and antibiotics, and was processed as described earlier to obtain T-cells from colorectal cancer tissues. T-cells from lung granulomatous lung tissue were designated as granuloma associated lymphocytes (GALs). Two of seven patients were diagnosed with rheumatoid arthritis or sarcoidosis, respectively (listed in Table 2). All patients tested positive for PPD-reactivity. Blood was drawn after informed consent of the individuals enrolled in the study which has been approved by the local ethics committee.

Flow Cytometry

Heparinized blood was drawn from patients at the time of diagnosis of pulmonary tuberculosis and at different time points after initiation of a standard triple therapy (rifampicin, ethambutol and isonizide). Every patient used in these studies complied with the treatment and showed clearance of pulmonary lesions. Peripheral blood mononuclear cells (PBMCs) were obtained by separation over a FICOLL™-gradient and stored in liquid nitrogen at 1-5×10$^7$ cells/vial in 90% fetal calf serum (FCS) and 10% DMSO. Frozen peripheral blood leukocytes (PBLs) were thawed and washed in RPMI-1640 supplemented with 20% FCS, the cell pellet was resuspended in RPMI supplemented with 1% FCS and incubated with 1 µg Phycoerythrin (PE)-labeled tetramer reagent for 30 mm at room temperature (for MHC class I tetramers) followed by incubation with directly Energy-coupled dye (ECD)-labeled anti-CD45RA (clone 2H4LDH11LDB9, murine IgG1), or with the Phycoerythrin-Cyanin (PC5)-labeled anti-CD8 alpha mAb clone B9.11 (murine IgG1) and anti-CD28 mAb (FITC, clone CD28.2). Staining of antigen-specific, HLA-DR4-restricted CD4+ T-cells was achieved by incubating PBL for 2 hrs as described below. All mAbs, except for the CCR5 specific mAb (CD195), which was purchased from BD/Pharmingen (San Diego, Calif.), were obtained from Beckman/Coulter, Krefeld, Germany.

Flow Cytometry Analysis

Cells were analyzed using the Coulter EPICS™ XL and XL-system software 2.1 (Beckman-Coulter, Fullerton, Calif.). Cells were separately gated on CD8+ CD45RA+ or CD8+ CD45RA– cells, followed by gating on CD28+/– cells, and finally tetramer-binding was evaluated. The presence of antigen-reactive lymphocytes in different T-cell subpopulations including precursor (CD45RA+, CD28+), activated (CD45RA–CD28+), memory (CD45RA–,CD28–) or effector (CD45RA+,CD28–) T-lymphocytes reflecting T-cell differentiation, homing and effector functions was performed as described. GALs (granuloma associated lymphocytes) from patients suffering from pulmonary tuberculosis or sarcoidosis were prepared as described for TIL from patients with colorectal cancer (Maeurer et al., J. Exp. Med., 1996). The Tine-Test was applied according to National Center for Clinical Laboratory Standards guidelines, and the experiments were approved by the local ethics committee. MHC class I and II alleles from each individual were determined by genomic typing using known methods.

Preparation of Tetramer-Reagents

Tetramer complexes were prepared from HLA-A2 wild-type (wt) or HLA-A2 mutant (HLA-A2m, alanine→valine at position 245 in the MHC class I-alpha 3 domain, resulting in reduced background-staining due to less efficient interaction of CD8 with the MHC class I heavy chain. The HLA monomers were loaded either with the HLA-A2 presented MTB epitopes from the 19 kDa antigen (VLTDGNPPEV) (aa 88-97) (SEQ ID NO:1), Ag85b (KLVANNTRL) (SEQ ID NO:2) or ESAT-6 (aa 28-36) (LLDEGKQSL) (SEQ ID NO:3) The CMVpp65 antigen epitope (NLVPMVATV) (SEQ ID NO:4) or the melanoma associated antigen gp100 (YLEPGPVTV) (SEQ ID NO:5) was used as a control. HLA-DR4 tetramer complexes were loaded with either (QMPYQPVQSPTQVEA) (19 kDA Ag) (SEQ ID NO:6), (PVEYLQYPSPSMGRD) (Ag85b) (SEQ ID NO:7) or (FAGIEAAASAIQGNV)(ESAT-$_{8-22}$) (SEQ ID NO:8). The tetramer complexes were directly coupled to PE and incubated for 2 hrs with PBL, either at room temperature (Ag85b and the 19 kDa Ag derived peptide) or 4° C. (ESAT-6) followed by staining with T-cell markers as described herein.

MHC class I (HLA-A2) restricted T-cell responses were tested using the peptides from the MTB Ag85 complex: Ag85a, aa 48-56: GLPVEYLQV (SEQ ID NO:21), Ag85a, aa 242-250: KLIANNTRV (SEQ ID NO:22) Ag85b aa 143-152: FIYAGSLSAL (SEQ ID NO:23), Ag85b aa 199-207, KLVANNTRL (SEQ ID NO:2), the 19 kDa antigen peptide VLTDGNPPEV (SEQ ID NO:1) (aa 88-97) and the candidate target ESAT-6 derived peptides AIQGNVTSI (SEQ ID NO:24) (aa 17-25), LLDEGKQSL (SEQ ID NO:3) (aa 28-36) and ATAELNNA (SEQ ID NO:25) (aa 62-70).

Immunomagnetic Cell Sorting and Functional Assays

CD4+ T-cells were separated from 3-5×10$^7$ PMBCs using anti-CD8 coated immunomagnetic beads (Miltenyi, Bergisch Gladbach, Germany). The CD8+ T-cell-depleted PBMC population was incubated with the respective PE-labeled tetramer reagents (1 µg tetramer/2×10$^7$ cells) for 2 hrs as indicated, washed once, and incubated for 15 mm with an anti-PE-directed mAb attached to immunomagnetic beads (Miltenyi, Bergisch Gladbach, Germany). Positive selected cells were rested for 24 hrs in 96-well plates containing 50% AIM-V-medium, 50% DMEM (high glucose) obtained from GIBCO™ (Eggenstein, Germany) supplemented with 10% FCS and 50 ng/ml human recombinant IL-7 (provided by Dr. Natalio Vita, Sanofi, France).

Tetramer-sorted cells were exposed to autologous macophages which had been infected either with *M. tuberculosis* or with *M. avium intracellulare* as described in detail previously for 72 hrs. The anti-DR directed mAb L243 was used to block MHC class II-restricted T-cell recognition of naturally processed and presented antigens, and the (anti-MHC class I directed mAb w6/32 was used as a negative control. Supernatants were harvested and tested for IFNγ or GM-CSF using and ELISA-system (Diaclone, Besancon, France). For peptide restimulation, PBL (5×10$^6$ cells/ml) were incubated with the appropriate peptide at 1 µg/ml in serum-free medium containing 50% AIM-V and 50% DMEM (high glucose) supplemented with 10 ng/ml IL-7 and 1 IU IL-2/ml for 7 days.

Tetramer In Situ Staining

Fresh frozen 5 µm thick sections from lung granuloma tissues from Tine+ individuals with no evidence of clinical tuberculosis (they underwent thoracotomy for diagnostic purposes to rule out lung cancer) were incubated on a shaker at 4° C., over night with HLA-A2 or DR4 tetramers complexes loaded with the appropriate peptides (final concentration 1 µg/ml) and a goat anti CD8 Ab directed against a peptide mapping at the carboxy terminal of the human CD8 alpha chain (final concentration 0.002 µg/ml, Santa Cruz, sc-1141) diluted in DAKO antibody diluent CHEMMATE™ dilution buffer (DAKO, Hamburg, Germany). The anti CD4 antibody (goat) has also been obtained from DAKO. The following steps were performed at room temperature (RT): wash 3×PBS for 2 mm, fixation in 2% formaldehyde solution buffered in PBS for 5 mm and 3×PBS for 2 mm, followed by mouse anti-PE (final concentration 0.001·mu·g/ml; Miltenyi, Germany) in dilution buffer for 30 mm followed by 3×PBS for 5 mm Biotinylated F(ab)$_2$ epitopes (final concentration 3.25

μg/ml, Dianova, Hamburg, Germany) were added in dilution buffer for 30 mm. ALEXA FLUOR™ 594-conjugated streptavidin (final concentration 1.25 μg/ml, Molecular Probes, Mobitec, Göttingen, Germany) and ALEXA FLUOR™ 488 donkey anti goat (final concentration 5 μg/ml) were added in dilution buffer for 30 mm followed by 3× washing steps with PBS for 5 mm and 3× with distilled water. Samples were air-dried and mounted in VectaShield mounting medium (Vector Laboratories, Burlinghame, Calif., USA). Slides were analyzed using a ZEISS AXIOSKOP™ 2 (Zeiss, Oberkochen, Germany) and documented with a Colorview-XS DIGITAL Camera (Olympus, Hamburg, Germany).

Example 2

HLA-DR4-Restricted ESAT-6 or AG85b-Tetramer-Sorted CD4+ T-Cells Recognize Naturally Processed and Presented Mycobacterial Antigens and are Present in Pulmonary Granuloma Lesions PBL from healthy HLA-DR4+ blood donors were tested for reactivity with HLA-DR4 tetramers loaded with peptides provided from the Ag85b, 19 kDAg and the *M. tuberculosis* specific antigen ESAT-6. Exclusively Tine-Test positive individuals tested positive for reactivity to any of the above listed antigens in the CD4+ T-cell population. In vitro expansion of CD4+ PBL in the presence of the nominal T-cell epitopes resulted in an expansion of CD4+ tetramer-reactive T-cells in Tine-Test positive and negative individuals. Both prior to and after in vitro stimulation, these T-cells were members of in the precursor CD4+CD45RA+CD28+ T-cell subset. Ex vivo analysis of tetramer-sorted CD4+ T-cells using either the Ag85b or the ESAT-6 epitope clearly showed that CD4+, HLA-DR4-restricted, and Ag85b-reactive T-cells recognized naturally processed and presented epitopes provided from *M. tuberculosis* and from *M. avium intracellulare* (FIGS. 11A-D). In contrast, DR-4-restricted and ESAT-6 specific T-cells recognized exclusively autologous macrophages infected with *M. tuberculosis*, but not with *M. avium intracellulare*. In order to examine whether DR4-restricted and *mycobacterium* species specific CD4+ T-cells are also present in granuloma lesions from the lung of Tine+positive individuals, tetramer-in-situ-staining and ex vivo analysis of granuloma associated lymphocytes (GAL) by flow cytometry was used to detect CD4+ and *mycobacterium* species antigen-specific T-cells. Costaining of tetramer-reactive and CD4+ T-cells in lung tissue showed the presence of HLA-DR4-restricted and 19 kDA antigen- or ESAT-6-specific T-cells consolidated by staining of GAL from the same specimens by flow cytometry: 0.1% of CD4+ GAL stained positive for the ESAT-6 epitope; 0.3% for the 19 kDa antigen; and 0.2% for the Ag85b antigen. A similar ex vivo-situation was found to be true for the HLA-A2 presented ESAT-6 epitope: costaining with ESAT-6 or 19 kDa tetramer complexes and CD8 detected antigen-specific and HLA-A2-restricted T-cells within the granuloma lesion. No tetramer-staining could be detected with an irrelevant control (melanoma gp100 antigen) tetramer reagent.

A more detailed analysis of ex vivo isolated GAL revealed that the majority of HLA-A2 or DR4-restricted T-cells directed against the 19 kDa antigen, the antigen 85b or ESAT-6 were found predominantly within the CD45RA+, CD28+ T-cell population.

Example 3

HLA-DR4-Restricted and Mycobacterium-Specific T-Cells Reside in the CD45RA+CD28+ and CD45RA−CD28− T-Cell Population and Show Different Dynamics Associated with Antigen-Specificity For longitudinal analysis, PBL were harvested from five patients with pulmonary tuberculosis at the time of diagnosis and after 2 and 16 weeks after diagnosis/initiation of therapy and tested for the reactivity to the 19 kDA antigen, the Ag85b and ESAT-6 in HLA-DR4 restricted CD4+ T-cells (FIG. 11A). The corresponding CD8+ and HLA-A2 restricted T-cell responses have been evaluated in three patients. Three of five patients showed an increase of DR4-restricted T-cells over time for ESAT-6 reactivity (patients MZTB1, -3 and -4). Patients MZTBC-3 and -4 showed also a corresponding increase for the HLA-A2 restricted epitope for ESAT-6, the CD8+ T-cell response in patient MZTBC-1 has not been tested. Four of 5 patients (except patient MZTBC-4) showed a decrease of DR4 restricted T-cells for the Ag85b epitope over time. The pattern of MHC class II-restricted and Ag85-reactive T-cells was found to be similar in the HLA-A2 restricted CD8+ immune response: Patient MZTBC-3 showed a decrease and patient MZTBC-4 showed an increase in both DR4 and A2 restricted Ag85b specific T-cell responses.

The DR-4 restricted CD4+ T-cell response against the 19 kDa lipoprotein exhibited a more complex pattern. Except for an increase in Ag-specific T-cells at 2 weeks after initiation of treatment in patient MZTBC1, four out of five patients exhibited a decrease of DR4/19 kDa Ag-reactive T-cells over time, patient MZTBC4 showed an increase of these T-cells over a 16 week period after initiation of therapy. The CD8+ T-cell response directed against the HLA-A2 presented 19 kDa Ag showed a similar pattern in patients MZTBC-3 and -5, i.e. decreased numbers of Ag-reactive T-cells, but revealed different dynamics in patient MZTBC-4: 19 kDa antigen-reactive DR4 restricted T-cells increased over time, but decreased if the 19 kDa antigen response is measured in the HLA-A2 restricted CD8+ T-cell population.

A more detailed analysis tested all blood samples compiled in FIG. 11 for the presence of mycobacterium antigen-reactive T-cells in different T-cell subsets based on differential staining with CD45RA and CD28. A typical example of the results is provided in FIGS. 13A-F. 7: ESAT-6, AG85b and 19 kDa antigen reactivity was found in all 4 different T-cell subsets in the CD8+ T-cell pool, while MHC class II (DR4)-restricted T-cell antigen-reactive CD4+ T-cells were predominantly found in either the precursor (CD45RA+, CD28+) or in the activated (CD45RA−, CD28+) T-cell subset. Since CCR5+ T-cells have been reported to be associated with homing to the broncho-alveolar system, the presence of mycobacterium-reactive and HLA-A2 or HLA-DR4-restricted T-cells in CCR5 neg. and CCR5 pos.+ T-cell subsets was also assayed. Irrespective of the low number of CCR5+ T-cells in peripheral blood, independent of the time point after initiation of therapy, CD4+ T-cells directed against ESAT-6, the 19 kDa Ag or Ag85b were present at least in equal numbers or were even elevated in the CCR5+ T-cell population as compared to CCR5-staining cells.

Example 4

In Vitro Expansion of Mycobacterium-Specific and HLA-DR4-Restricted T-Cells does not Impact on the T-Cell Differentiation Phenotype Similarly to the situation in healthy, tine-test positive individuals, low or undetectable CD4+ T-cells in patients with tuberculosis (e.g. PBL from patient MZTBC5) that recognize either the AG85b, 19 kDa, or ESAT-6 antigen in the context of DR4, could be expanded during a 7 day stimulation with the appropriate peptide in vitro: the predominant CD4+ T-cell response is again detected within the precursor (CD45RA+CD28+) or in the activated (CD45RA−CD28+) T-cell subset (FIGS. 13A and B). Of note, however, in vitro expansion of antigen-reactive CD4+ T-cells in the presence of the nominal peptide epitope drastically decreases the CD45RA−CD28− and CD45RA+CD28− T-cell subset and increases the CD45RA+CD28+ and CD45RA−CD28+ T-cell population irrespective of the time point of the blood harvest after initiation of therapy. The same pattern was found to be true for CD8+ T-cells cells subjected to in vitro expansion with HLA-A2 presented mycobacterial peptides (data not shown).

Noteworthy, individual patients (e.g. MZTBC4 and MZTBC5, FIG. 5) showed a strong CD8+ mycobacterium-reactive Ag85b-specific T-cell response, despite low numbers of CD4+ T-cells reactive to the same antigen. Recent reports suggested that functional CD8+ T-cell memory is dependent on CD4 T-cell help), although data from murine models of pulmonary MTB infections suggested that expansion and IFN production from CD8+ T-cells does not depend on CD4+ T-cell help except for acquisition of cytolytic activity. In general, the dynamic pattern in PBL of the CD4+ T-cell response turned out to be dependent on the nature of the antigen and may also be different from patient to patient as observed in other studies using a mix of different ESAT-6 peptides in ELISPOT assays. This may be due to different homing scenarios of T-cells in the peripheral circulation or to the differential availability of antigen required for restimulation and T-cell maintenance, since the MTB-associated 19 kDA lipoprotein is able to interfere with effective MHC class I and class II antigen processing and presentation in macrophages and may therefore affect T-cell memory.

To date, assays gauging anti-TBC directed T-cell reactivity have been limited by the fact that PBL are used as a source for measuring T-cell responses. The peripheral T-cell repertoire represents only 2% of the entire lymphocyte pool and assay systems have been based on the presumption that this pool is in equilibrium with the other 98% of T-cells present in tissue. However, chemokine receptor 5 (CCR5) positive T-cells represent a memory T-cell subset that is infrequent in blood, spleen and lymph nodes, but is present in tissues, including the mucosal surface of the intestine, and the respiratory and reproductive tracts. In all patients examined in the Examples herein, only a small fraction (up to 3%) of peripheral lymphocytes stained positive for CCR5. Despite the low number of CCR5+ T-cells in peripheral circulation, it has been found that HLA-DR4-restricted CD4+ T-cells do not reside exclusively in the CCR5 negative T-cell population and HLA-A2-restricted and tetramer-reactive T-cells show either equal or higher numbers of tetramer reactive T-cells in CCR5+ T-cells. This observation was not restricted to antigens provided from MTB, but could also be identified in HLA-A2-restricted CMVpp65 specific T-cells. The CCR5+ cells stained negative for CD25, a marker for T-cell activation (data not shown). Thus, if CCR5 is associated with T-cell homing, at least 50% of all MTB MHC class I and class II-restricted T-cells in PBL reside in lymphocytes capable of homing to the respiratory tract.

One of the key discoveries that form the basis for this invention is that the majority of the HLA-DR4-restricted responses are found in the 'precursor' CD45RA+CD28+ and the activated CD45RA−CD28+ CD4+ T-cell populations, whether in pulmonary granuloma associated lymphocytes from patients who were able to contain the infection, in patients with pulmonary tuberculosis at different time intervals after diagnosis and initiation of treatment, after in vitro expansion, or ex vivo in PBL from TST+, healthy individuals: These data are consistent with a murine model of MTB infection, in which adaptive CD4+ T-cell transfer experiments suggested that memory effector T-cells are indeed able to revert to a 'naïve' phenotype, which ability may contribute to a 'precursor' T-cell pool crucial for long-term immune surveillance and protection. This phenomenon is also important for the in situ containment of bacilli in granuloma lesions (see FIG. 3). This finding has been substantiated in more recent data from CD4+ T-cell phenotype in life-long infections, e.g. in patients with EBV infection. Individual CD4+ T-cell populations directed against EBV latent and lytic cycle proteins express CD27 and CD28 and CD45RA. Thus, it has been shown that only ex vivo analysis using MHC class II tetramer complexes in combination with T-cell marker analysis provides a determination of the protective and peptide antigen-specific immune response in latent MTB infection.

Example 5

Highly Focused T-Cell Responses in Latent Human Pulmonary *M. tuberculosis* Infection Disease containment in TB involves a complex network of different T-cell subsets and their ability to mount and maintain effective immune responses. Our knowledge of all engaged immune events is yet to be complete. The essential role of MHC class 11 restricted CD4+ and MHC class I restricted CD8+ T cells is well established. One of their major weapons is the production of cytokines, e.g. IFN-γ and TNF-α, that can activate macrophages and induce production of bacteriocidal molecules. Nonclassically restricted CD8+ lymphocytes, CD4− CD8− and CD 1-restricted T cells, γδ+ T-cells and NK cells have also been reported to recognize MTB-associated antigens and to be involved in disease control.

This knowledge is derived largely from studies in mice. Most studies on active or latent human TB to date are limited to the analysis of peripheral blood lymphocytes (PBL) and do not address the immunological situation at the primary site of MTB infection, the lung. Our objective was to determine which factors are responsible for containing MTB and sustaining latency in the human lung. In Five patients with latent MTB infection we cultivated GALs from lung biopsies and analyzed these cells in regard to their molecular composition, phenotype, frequency, antigen-specificity, and function. Furthermore, we took a direct look at the in vivo immunological situation in the lung tissue by CLSM, utilizing tetramer technology.

Patients

Five patients were recruited from the university hospital Heidelberg who underwent explorative surgery to rule out a malignant lesion of the lung. The surgical specimens (approximately 10 mm×8 mm) were analyzed by HE-staining and revealed no evidence of cancer, but granuloma formation associated with a strong T-cell infiltrate. No major areas of calcification or caseous alterations were identified. Sputum (obtained after surgery) as well as aliquots from the surgical specimens were cultured according to NCCLS standards for 6 weeks in a liquid (BACTEC MGIT™ 960, Becton Dickinson, Heidelberg, Germany) and using a solid (Lowenstein-Jenssen, Becton Dickinson, Heidelberg, Germany) medium. No viable mycobacteria could be identified. Aliquots from the surgical specimens tested positive by PCR for MTB (COBAS AMPLICOR™ *mycobacterium tuberculosis* test, Roche, Düsseldorf, Germany). Thus, patients were diagnosed for latent MTB infection based on i) typical pulmonary lesions by x-ray, ii) PCR-based MTB detection and iii) typical granuloma formation defined by HE-staining. This pattern (in the absence of cultivable bacteria) is consistent with 'latent MTB infection' as reviewed recently in which is in accordance with in situ PCR analysis of human lung tissue obtained from individuals (at autopsy) with no clinical evidence of MTB. An aliquot of each surgical specimen was cut into small (1 mm×1 mm) pieces as described earlier for specimens from patients with colorectal cancer. Briefly, tissue sections were placed into 48-well plates supplemented with RPMI, 10% FCS and antibiotics plus 50 ng recombinant human IL-7/ml, kindly provided by Dr. Adrian Minty, Sanofi, France.

T-cells from lung granulomatous lung tissue grew out within 48 h and, designated as granuloma associated lymphocytes (GALs), were subjected to further analysis. For some patients, only a limited number of T-lymphocytes could be obtained which did not allow a comprehensive CD4+ or CD8+ T-cell analysis in each case. Of note, T-cells were not restimulated with peptides or autologous macrophages. All patients tested positive for PPD-reactivity according to NCCLS guidelines. Blood was drawn after informed consent of the individuals enrolled in the study which has been approved by the local ethics committee (on file with the reference no. 837.327.99 (2272) from Nov. 15, 1999).

Flow Cytometry and Tetramer Analysis

Heparinized blood from patients was drawn and PBMCs were obtained by separation over a FICOLL™-gradient and stored in liquid nitrogen at $1-5\times10^7$ cells/vial in 90% fetal calf serum and 10% DMSO. Tetramer-reagents loaded with the HLA-A2 binding *M. tuberculosis* 19 kDa peptide VLTDGN-PPEV (SEQ ID NO:1), the *M. tuberculosis* peptide MTB Ag85b, KLVANNTRL (SEQ ID NO:2), the ESAT-6 peptide LLDEGKQSL (SEQ ID NO:3), or the HLA-DR4 tetramer complex loaded with the ESAT-6 peptide FAGIEAAA-SAIQGNV (SEQ ID NO:8) were prepared and obtained from the Immunomics Corporation (Beckman Coulter, San Diego, USA). HLA-A2 tetramer complexes loaded with the CMVpp65 epitope NLVPMVATV (SEQ ID NO:4) or the melanoma associated gp100 peptide YLEPGPVTV (SEQ ID NO:5) (Beckman/Coulter) served as controls. Frozen PBL were thawed, washed, and tetramer analysis or TCR VB frequency was performed as described earlier in detail.

Tetramer In Situ Staining

Tetramer in-situ staining was performed using the identical granuloma lesions subjected to TCR-CDR3 analysis. We only had sufficient amounts of tissue from patients #3 and #4 available to perform T-cell in situ detection. 10-20 frozen sections at 10 μm thickness from lung tissue were obtained and incubated at 4° C., (final concentration 1 μg/mL diluted in 2% normal goat serum in PBS) overnight either with PE-labeled HLA-A2 tetramers loaded with the *M. tuberculosis* 19 kDa or the Ag85b epitope as listed above. The following steps were all performed at room temperature and primary and secondary antisera were diluted in antibody diluent buffer (DAKO, Hamburg, Germany). Sections were washed three times in PBS, fixated in 2% formaldehyde solution buffered in PBS for 5 mm, followed by three washing steps using PBS. Mouse anti-PE (Sigma, Deisenhofen, Germany) was incubated at 1:100 for 2 h followed by three washing steps with PBS. Cy3-labeled donkey anti-mouse (Dianova, Hamburg, Germany) was used at a dilution of 1:800 for 1 h. Double staining with mouse anti-human CD8alpha (DAKO, clone C8/144B) was performed at a dilution of 1:50 for 1 h. Prior to this incubation, a biotinylation step with the ARK™-Kit (DAKO) was applied according to the manufacturer's instructions to avoid cross recognition. FITC-labeled streptavidin (DAKO) was applied at 1:50 to detect CD8+ T-cells. Tetramer-positive cells appear in red and CD8+ T-cells in green. Specimens were photographed with ColorViewXS (Olympus, Hamburg, Germany) attached to a ZEISS AXIOSKOP™ microscope (Zeiss, Oberkochen, Germany).

Immunomagnetic Cell Sorting and Functional Assays

CD4+ or CD8+ T-cells were separated from $3-5\times10^6$ PMBCs or GALs using anti-CD4 or CD8 coated immunomagnetic beads (Miltenyi, Bergisch Gladbach, Germany). TCR VB-sorted T-cells were obtained using VB-specific mAbs (Beckman Coulter, Krefeld, Germany) directly labeled with PE, followed by anti-PE directed immunomagnetic bead sorting. T-cells were cultured for 48 h in 96-well plates containing 50% A1M-V-medium, 50% DMEM (high glucose) obtained from GIBCO™ (Eggenstein, Germany) supplemented with 10% FCS and 50 ng/ml human recombinant IL-7. CD4+, CD8+ or TCR-VB-sorted cells were admixed with T2-cells pulsed with the appropriate peptide epitope in order to determine MHC class I restricted cytokine production for HLA-A2+ patients. T2-cells loaded either with diluent alone (10% DMSO, 90% RPMI) or 1 μg of peptides as indicated, supplemented with human beta-2 microglobulin (20 μg/$10^6$ cells/ml) obtained from SIGMA (Deisenhofen, Germany) served as the target cell population. 50 μl of this target cell suspension was used per well, effect on target ratio was 1:1. Autologous irradiated PBMCs were used to detect MHC class II responses. PBMCs from individual patients were pulsed with ESAT-6 derived peptides (aa 1-20 MTE-QQWNFAGIEAAASAIQG (SEQ ID NO:26) and an 72-95 LARTISEAGQAMASTEGNVT-GMFA) (SEQ ID NO: 27) as indicated for 2 hrs at 37° C., followed by 48 hr incubation with CD4+ responder T-cells. These ESAT-6 derived peptides have been described to be recognized by the majority of T-cells from patients with tuberculosis and appear to bind promiscuously to most HLA-DR alleles. For testing of *M. tuberculosis* infected autologous macrophages, macrophages were selected by PBMC adherence to plastic for 2 h followed by 2 careful washing steps with medium supplemented with FCS. Macrophages were infected with a freshly isolated *M. tuberculosis* strain, designated as M.tub MZ#610, from the sputum of patient suffering from pulmonary tuberculosis 24 hrs prior to assay as described previously. Effector T-cells were incubated with targets for 48 h (E:T ration=1:1), supernatants harvested and tested for IFNγ, IL-4 or GM-CSF using the ELISA-system obtained from Diaclone, Besancon, France. In order to compare results using different effector populations (e.g. CD4+ or CD8+ GAL versus TCR-VB-sorted GAL), we implemented the same batch of APCs in all experiments MHC class I-restricted T-cell responses were blocked with 10 μg/well of the anti-MHC class I specific mAb W6/32, the anti-DR specific mAb L243 was used to block MHC class II-restricted (HLA-DR) T-cell responses. Clone H143 was directed against DP and clone TU169 against DQ class II alleles. Both were obtained from BD/Pharmingen, Hamburg, Germany.

MHC class I (HLA-A2) restricted T-cell responses were tested as described earlier using the peptides from the MTB Ag85 complex: Ag85a, aa 48-56: GLPVEYLQV (SEQ ID NO:21), Ag85a, aa 242-250: KLIANNTRV (SEQ ID NO:22) Ag85b aa 143-152: FIYAGSLSAL (SEQ ID NO:23), Ag85b aa 199-207, KLVANNTRL (SEQ ID NO:2), the 19 kDa antigen peptide VLTDGNPPEV (SEQ ID NO:1) (aa 88-97) and the candidate target ESAT-6 derived peptides AIQGNVTSI (SEQ ID NO:24) (aa 17-25), LLDEGKQSL (SEQ ID NO:3) (aa 28-36) and ATAELNNA (SEQ ID NO:25) (aa 62-70).

TCR-CDR3-Spectratyping

The molecular TCR composition of either CD4 or CD8 positive-sorted T-cells (using immunomagnetic beads) or tetramer-sorted T-cells, using either HLA-A2/Ag85b or HLA-DR4/ESAT-6 complexes, were carried out as described. These T-cells, not restimulated in vitro, were obtained after a 48 h culture period in the presence of IL-7. Of note, IL-7 has been reported not to skew the TCR repertoire. Briefly, RNA was extracted from $2 \times 10^5$ cells and reverse transcribed into cDNA, amplified by individual TCR VB-specific primer pairs and a run-off reaction using a fluorophore-labeled TCR-CB-specific primer (PCR conditions: 94° C., 1 min/60° C., 1 min/72° C., 1 mm, 40 cycles) was performed. Labeled amplicons were analyzed by DNA epitope analysis using appropriate size-standards and a 310 sequencer and GENESCAN™ software (ABI, Weiterstadt, Germany). Serial dilutions ($10 \times 10^5$ m$\times 5 \times 10^5$, $2 \times 10^5$, $1 \times 10^5$, $0.5 \times 10^5$) of either CD4+ or CD8+ sorted T-cell populations showed that the use of at least $1 \times 10^5$ T-cells in this assay system results in highly reproducible TCR patterns pertaining to intra- and inter-assay variations and does not lead to "false positive" monoclonal TCR-CDR3 patterns. In order to identify monoclonal/oligoclonal TCR transcripts, amplicons were subcloned into the TA sequencing vector (Invitrogen, Groningen, The Netherlands). TCR VA/VB were only reported as monoclonal if either direct sequencing of the PCR amplicon or all subcloned PCR transcripts yielded the identical TCR-sequence. If the TCR VA/VB family is oligo- or polyclonal, a Gauss-distribution of the CDR3 length occurs. Each peak represents in-frame transcripts with a given CDR3 length. The area under the curve represents the frequency of a distinct CDR3 length in an individual TCR VA/VB family. In order to condense the information from a single sample analysis, the individual TCR VA or VB families were grouped into a single figure with VB1-VB24 along with the CDR3 length expressed as the number of amino acids. This TCR-CDR3 landscape provides the 'structural anatomy' as defined by the TCR-CDR3 length for each TCR-family in a T-cell subpopulation. The area under the curve of each CDR3 peak is expressed as the percentage of the entire CDR3 area (100%). For sake of visibility, differences are depicted in different colors as indicated on the scale intervals. The CDR3 pattern obtained from CD8+ or CD4+ T-cells obtained from granulomatous lesions (GALs) can be compared with the CD4+ or CD8+ sorted PBL obtained at the same time, i.e. during surgery. This TCR 'perturbation' within each CDR3 length is calculated by the areas between the CDR3 distribution in each sample and the control distribution. Positive or negative perturbations may occur in each TCR VA/VB CDR3 peak and are depicted as differences as compared to the control sample. Each perturbation yielding a 10% difference is depicted in a different color. Note that a 'flat' TCR landscape in this analysis implies that no perturbation exists, i.e. the TCR-VA/VB landscape would yield the identical picture as compared to the control sample. Comparative analysis of TCR CDR3 length measurements in CD 8+, CD4+ (unsorted) GAL was carried out using corresponding freshly harvested lung tissue obtained from 2 patients.

CDR3-Analysis and TCR-VB-Staining: Quantitative TCR Analysis

TCR-spectratyping yields only the qualitative, but not the quantitative assessment of a T-cell population. A panel of 24 individual mAbs directed against the TCR VB chain (Beckman Coulter, Krefeld, Germany) were grouped to three individual anti-VB mAbs either labeled with FITC, PE, or double-labeled with FITC/PE which can either be gated on ECD-CD4, or PC5-CD8+ T-cells. Thus, the frequency of 24 individual TCR VB families either in the CD4+ or CD8+ T-cell populations can be analyzed in eight different tubes, which yields the percentage (X % of a VB-family) in CD3+ CD8+ T-cells. This factor can now be used to correct the CDR3-VB-landscape analysis. Exclusively a mAb panel directed against TCR VB-chains, but not TCR-VA-chains is available.

Results

Granuloma associated lymphocytes were cultivated from lung biopsies of five patients that presented with a lung lesion of unknown etiology. Pathological diagnosis (typical granuloma formation) and PCR-assisted amplification of MTB revealed latent tuberculosis infection in 5/5 patients. No viable mycobacteria could be isolated from sputum, broncholavage or the biopsy itself. Thus, we had the possibility to analyze PCR-positive, culture-negative human lung granuloma tissue for T-cell reactivity to MTB-associated antigens.

The aim of this study was to ascertain the aspects involved in sustaining MTB latency in the human lung by analyzing a) the quality of the T-cell responses, as determined by T cell receptor (TCR) CDR3-spectratyping, b) the quantity of the T cells in each TCR VB-family, as determined in flow cytometry analysis, and c) the function of the GALs, as defined by cytokine production.

Example 6

CD4+ GALs and CD8+ GALs are Oligoclonal, Composed of Highly Expanded VB Families and Constitute an Idiosyncratic Population as Compared to PBL After magnetic bead sorting, CD4+ and CD8+ GAL populations were analyzed separately for the 'objective' structural composition of their TCR repertoire, defined by TCR CDR3 spectratyping complemented by a quantitative assessment of the TCR repertoire measured by flow cytometry. In FIGS. 1 and 2 the 'TCR landscapes' have been plotted showing 24 VB families on the x-axis, the CDR3-lengths within the family as amino acid counts on the z-axis, and the percentage of CDR3 lengths within the lymphocyte population as a combination of the flow cytometrical enumeration and the area under the curve as determined by CDR3 analysis on the y-axis.

An augmentation of a single CDR3 length within a VB family is considered to be due to an expansion of T lymphocytes that are possibly involved in a specific immune response. Each patient showed an individual, particular TCR VB profile for both the predominantly oligoclonal CD4+ (FIG. 1) and the CD8+ GAL population (FIG. 2). In some patients, T-cells belonging to a distinct oligoclonal or monoclonal VB family constituted a major fraction of the lymphocyte population. For example, in patient #1 VB14 positive CD4+ lymphocytes and in patient #5 VB7 positive T cells accounted for 27% and 19% of all CD4+ GALs, respectively. TCR CDR3-spectratyping suggested that these VB families were composed of a single T-cell clone. We sequenced the individual TCRs (Table 2) and proceeded to analyzing their function in latent TB.

Major T-cell expansions could also be found in CD8+ GALs: monoclonal VB3 positive T-cells in patient #1 (see Table 2 for TCR sequence) and oligoclonal VB17 positive lymphocytes in patient #3 constituted up to 17% and 9% in CD8+ GAL, respectively. No common expansion of a TCR VB family could be identified in comparing the individual patients or HLA-type which might have indicated a preferential VB usage in human MTB containment.

As the panel of 24 VB-specific antibodies commercially available covers over 80% but not the complete VB repertoire, we were as yet not able to identify all T cells (in a quantitative fashion) that may be involved in controlling MTB. For example, in patient #1 20% of CD4+ and 55% of CD8+ GAL could not be quantitatively assessed for VB expression in flow cytometry. These T cells, for which VB frequencies could not be measured, comprised only few additional VB families by molecular assessment and thus may also have been clonally expanded (data not shown).

In order to determine if the TCR repertoire of the lung is a mere mirror image of the peripheral blood or if the lung acquires its distinct repertoire, we analyzed both compartments (GAL vs. PBL) patients (except PBL for patient #1 due to limited material) and present the data obtained for patient #2 (for both CD4+ and CD8+ T cells) and for patient #5 (for total/unsorted PBL and GAL) as a proof of principle in FIGS. 3 and 4. By subtracting the GAL 'TCR landscape' from the 'TCR landscape' obtained for PBL we visualized the percent differences, as shown in FIGS. 3A-B (molecular TCR-CDR3-analysis) and FIG. 4A-B (molecular TCR-CDR3-analysis corrected by analysis of TCR VB-frequencies). The perturbed landscapes indicate that each compartment was indeed composed of a dissimilar TCR-repertoire and that individual TCR families are preferentially expanded within granuloma tissue. Had the repertoires been identical, a flat landscape would have resulted. Unsorted (48 h, IL-7 expanded) GAL showed a similar TCR composition as compared to the corresponding freshly isolated granuloma tissue section.

Example 7

CD4+ GALs Show a Th1 Cytokine Secretion Pattern in Response to MTB Epitopes Presented by Autologous Macrophages Before addressing the function of those GALs characterized by an expanded VB family, we determined, in a more general approach, the function of the heterogenous CD4+ and CD8+ GAL populations in a cytokine release assay, using autologous macrophages as antigen presenting cells (APCs) that had been infected in vitro overnight with viable MTB bacilli. CD4+ GALs from 3/5 patients could be sufficiently expanded. They produced IFN-γ at levels of 110 to >1000 pg/ml (FIG. 1), while GM-CSF was exclusively measurable in CD4+ GAL from patient #3 (data not shown). Regarding CD8+ TCR+ GALs, 0/3 analyzed patients produced IFN-γ, only CD8+ GAL from patient #3 showed an immune response in respect to GM-CSF production while IL-4 was not measurable in any patient (data not shown). Of note, prior in vitro stimulation of the analyzed lymphocytes using MTB-antigens had not been done.

In patient #3, no IFN-γ or IL-4 was measurable as a response to naturally processed and presented MTB epitopes on autologous APCs. However, GALs of this patient were capable of producing substantial amounts of IFN-γ in response to MTB-derived peptides in a different experimental setting (FIGS. 8 and 9), suggesting that these cells were functionally capable of secreting cytokines.

In order to confirm MHC-restriction, we performed additional experiments using blocking monoclonal antibodies (mAbs) directed against MHC class I or II antigens. Cytokine production was either partially or completely inhibited by mAbs directed against DR, DP, and DQ in the CD4+ GAL population (FIG. 1), indicating that MTB peptides were presented on MHC class II molecules.

Example 8

CD4+ GALs and CD8+ GALs Characterized by an Expanded VB Family are the Major IFN-γ Producers In order to investigate if an expansion of a VB family within the CD4+ and the CD8+ GAL population is indeed indicative of a major functional role in disease combat, we sorted the GALs according to their expanded VB family and analyzed them in cytokine release assays. As elaborated above, TCR-CDR3 spectratyping coupled with flow cytometry allowed us to recognize VB9 and 14 in patient #1, VB8 and VB9 in patient #2, and VB7 in patient #5 as the major represented VB families in the CD4+ GAL population as well as VB3 in patient #1 in CD8+ GALs. We sorted and exposed T-cells, expressing the relevant VB families, to MTB-infected autologous macrophages for 48 hours, as described above. The production of IFN-γ by these T cells resulted in much higher concentrations (ranging from 1300-9955 pg/ml for CD4+ GALs, 1185 pg/ml for CD8+ GALs; FIG. 5) than were produced by the whole population of GALs at comparative cell counts. As expected, mAbs directed against MHC class I inhibited cytokine production of VB3+ CD8+ GALs. In CD4+, VB-sorted GALs, IFN-γ production was blocked either by DR, DP, or DQ mAbs, suggesting that the sorted T cells were restricted to a single MHC class II allele.

Example 9

CD4+ GALs, Belonging to a Certain Expanded TCR VB Family, Recognize ESAT-$6_{1-20}$ To determine antigen-specificity of the sorted CD4+ GALs, we analyzed the ability of the individual TCR VB-sorted T cells to recognize MTB derived DR-binding peptides ESAT-$6_{1-20}$ and ESAT-$6_{72-95}$. VB-sorted GALs recognized ESAT-$6_{1-20}$ and produced IFN-γ in patients #1, #2, and #5, whereas ESAT-$6_{72-95}$ induced an IFN-γ production above background levels only in VB7+ GALs of patient #5 (FIG. 6).

An increase of peptide concentration evoked a stronger cytokine response, as shown in FIG. 4A-E, but at the highest peptide concentration tested results varied, ranging from a further increase in patient #2 to suppression of IFN-γ in patient #5. When analyzing the corresponding TCR VB-depleted GAL population in the identical experimental setting, we observed that these GALs did not recognize the ESAT-$6_{1-20}$ peptide as no IFN-γ production was measurable above background levels (VB9-negative GALs in patient #1: 4 pg/ml; VB9-negative GAL in patient #2: below detection levels; VB7-negative GALs in patient #5: 45 pg/ml; data not shown in FIG. 6). Recognition of ESAT-$6_{1-20}$ was, therefore, restricted to a single VB family in these three patients or even a single VB7+ T cell clone in patient #5.

Example 10

MTB Derived HLA A2-Binding Peptides Evoke a Tc1 Cytokine Response in CD8+ GALs Recognition of peptides provided by MTB-associated antigens ESAT-6, 19-kDa Ag or Ag85a/b was investigated in the CD8+ GAL population of HLA A2+ patients (Table 1, FIG. 8A-B). MTB-derived HLA A2-binding peptides $Ag85a_{48-56}$, $Ag85a_{242-250}$, $Ag85b_{143-152}$, $Ag85b_{199-207}$, and 19-kDa $Ag_{88-97}$, respectively, were loaded on T2 cells, CD8+ GALs added, and the in vitro cytokine production was measured after 48 hours of incubation. A melanoma-derived HLA-A2 binding gp100-derived peptide was used as a negative control.

While 19-kDa $Ag_{88-97}$ evoked moderate cytokine production, peptides $Ag85a_{242-250}$ and $Ag85b_{199-207}$ were recognized, as determined by IFN-γ and GM-CSF production. The other peptides had not elicited a much higher cytokine production than the control peptide gp100 in any patient. IL-4 was not detectable in any case (data not shown). In addition, GALs derived from patient #3 were analyzed for reactivity to three A2-binding target peptides provided from ESAT-6. These GALs recognized $ESAT-6_{28-36}$ in a MHC class I restricted manner and produced substantial amounts of IFN-γ and GM-CSF (FIG. 9A-B). $ESAT-6_{17-25}$ and $ESAT-6_{62-70}$ elicited minor cytokine production. The presence of peptide reactive GALs was substantiated by HLA-A2 tetramer staining in GAL: CD8+ GAL from patient #3 stained positive for the ESAT-6 peptide LLDEGKQSL (SEQ ID NO:3) (2.4%), 1.1% and 1.6% for the 19-kDa and the Ag85b tetramer, respectively (data not shown).

Example 11

MTB-Reactive GALs In Situ Defined by Tetramer Analysis

We have been able to obtain sufficient serial sections from the granuloma lesions from patients #3 and #4 which allowed us to visualize antigen-specific CD8+ GALs in situ by staining with HLA A2 tetramers for $Ag85b_{199-207}$ and 19-kDa $Ag_{88-97}$. TCR bound tetramers appeared red in CLSM while mAbs directed against CD8α were FITC-labeled and appeared green (FIG. 20). However, tetramer in situ staining allows to visualize the spatial arrangement of the MHC class 1/peptide-specific T-cells in situ, but does not address the molecular composition of the antigen-specific T-cell population. In order to assess the TCR usage in MHC/peptide-specific T-cells, we sorted HLA-2/Ag85b-binding CD8+ GAL from patient #3 and performed TCR-CDR3 analysis (FIG. 21). The comparison of TCR usage in tetramer-sorted and CD8+ GAL shows the presence of a few clonotypes directed against a defined T-cell epitope. T-cells have been harvested from a granuloma lesion (HE, parallel section) with marked lymphocytic infiltration (FIG. 20a). A few T-cell clonotypes constitute also the HLA-DR4 restricted, ESAT-6 specific CD4+ T-cell population isolated from a different patient with latent human pulmonary tuberculosis (FIG. 21). Tetramer in situ staining (FIG. 20b) suggests that Ag85b-reactive T-cells are focused to several loci in the granuloma tissue. As previously observed in murine lymphoid tissue, tetramer staining visualized TCRs that seemed clustered at one (or few) pole(s) of the T cell, giving an impression of a bright red dot or dots on the circular cell, while CD8 seemed more equally distributed, giving the cell a homogenous, annular appearance. Upon double expression, the red and green resulted in an orange-yellow coloring of the cells. Staining with gp100-MHC tetramers, as a negative control, lead to mere background staining. The tetramer-positive cells were focused to several different loci within the granuloma section. The HE-staining of a parallel tissue section is shown for patient #3.

Example 12

Summary

The immunological situation in latent tuberculosis has been difficult to understand and research. The results obtained from the analysis of PBL in humans may not necessarily reflect the immune response at the site of infection itself. Several studies report a prominence of Th2-type cytokines, e.g. IL-10, in PBL. On the other hand, T cells from other compartments in patients with active TB, such as pleural effusions or T-cells isolated by bronchoalveolar lavage, showed a marked IFN-γ and/or proliferative response that was lower or even absent in PBL of the same analyzed patients. This phenomenon may be due to sequestration of distinctive MTB-reactive T cells to the site of infection, possibly on account of particular chemokine receptors, such as CCR2 or CCR5. Hence, a closer look at the immunological events in the lung tissue itself is essential for a better comprehension of protective immunity to MTB.

The fine specificity of TCR antigen recognition resides in the complementary-determining region 3 of the TCR VA and VB chain. The clonal expansion of antigen-specific T cells in response to antigen is reflected as a single or a few overrepresented CDR3-peak(s) within a VB family in CDR3-spectratyping. Ultimately, this clonal expansion of T cells can translate into an augmentation of the relevant VB family within the VB repertoire, as described for both viral and bacterial infections. We showed that GALs isolated from human lung tissue were characterized by oligoclonal or monoclonal expansions of individual VB families. These TCR VB expansions in GAL could not be observed in corresponding PBL, suggesting that the MTB-reactive T cells had indeed been sequestered to the lung. A comparable compartmentalization has been reported in a study on active human TB, in which the TCR VB repertoire of lymphocytes from pleural fluid differed from that found in PBL. The fact that the TCR repertoire analysis in freshly obtained granuloma tissue exhibited a similar pattern as compared to (unsorted) 48 h expanded GAL (see FIGS. 3 and 4) and that IL-7, used for T-cell culture, does apparently not skew the TCR repertoire suggests that the functional TCR composition data indeed reflect the in situ situation.

CD4+ GALs readily recognized MTB-infected autologous macrophages and produced IFN-γ, a key cytokine well-established in contributing to immunity against MTB. In contrast, CD8+ GAL failed to produce INF in response to autologous MTB-infected targets (data not shown), despite the fact that CD8+ TCR VB3-sorted T-cells recognize the same MTB-infected antigen-presenting cells (FIG. 6A-F). Two mutually not exclusive mechanisms may account for this phenomenon: First, the effector:target ratio in the (clonal, see Table 2) TCR VB3-sorted T-cells may have been superior as compared to the unsorted CD8+ GAL population in which the VB3+ cells constituted up to 17% (FIGS. 1 and 2). Second, in vitro infection of autologous macrophages with MTB may rather facilitate presentation of MHC class II presented epitopes (see FIGS. 1 and 2).

The frequencies of expanded, MTB-specific T cell clones were unexpectedly high in the lung tissue (reaching up to 27% of CD4+ GAL in an individual patient) as compared to our previously published findings for CD8+ MTB Tet-19 kD Ag+ reactive T cells in PBL of patients with active TB (approximately 2% of CD8+ PBL) or, in respect to tissue residing lymphocytes, as seen for Melan-A/MART1$_{27-35}$-specific tumor infiltrating T-cells (5.68% of TILs). The frequency differences seem even more pronounced, considering that tetramer analysis or limiting dilution assays used in these studies may reflect frequencies for antigen-specific T-cells of diverse T-cell clones, while we had observed single T-cell clone expansions in GALs. Masopust and coworkers, on the other hand, have detected frequencies similar to those in GALs, when analyzing organ-specific tetramer-reactive T cell responses in acute murine listeriosis. These frequencies declined after successful resolution of the disease. In latent MTB infection, T-cell frequencies may remain elevated as the infection is essentially not cleared due to the persistence of bacilli inside macrophages for many years.

For three patients diagnosed with latent TB infection, we were able to define the antigen-specificity of the major expanded VB family (VB9 in patient #1 and #2 and VB7 in patient #5). These GALs produced increased amounts of IFN-γ in response to naturally processed and presented MTB epitopes as compared to the whole CD4+ GAL population. In patient #5, for example, a single VB7 positive T-cell clone (Table 2) made up 19% of lung-residing lymphocytes that were dedicated to the recognition of an ESAT-6 epitope. Of note, the same TCR VB7 clone has been identified by TCR-CDR3 typing in the corresponding freshly harvested lung lesion, suggesting that the VB7 family has been clonally expanded in situ (data not shown). The early secreted antigenic target 6 (ESAT-6) has been implicated to be sensitive and specific for the detection of active or latent MTB infection in humans due to its absence of expression in BCG and most environmental mycobacterial species. Moreover, these expanded lymphocytes were the sole CD4+ T cells that recognized ESAT-6$_{1-20}$ in the whole GAL population. This indicates a highly focused immune response to select MTB antigens in the lung. These data suggest that successful MTB containment, at least in some patients, may be highly focused and restricted to a few TCR-clonotypes: A situation which was found to be true for successful containment of HIV or more recently, for clinically effective T-cell responses in patients with cancer.

We were not able to link all expanded TCR VB families to the recognition of naturally processed and presented MTB epitopes in this report. Different repertoires of MTB epitopes may be generated, associated with environmental conditions which direct the MTB transcription machinery of genes necessary for intracellular survival. Most likely, ON infection of autologous macrophages with MTB, used as APCs in the current study, may not reflect antigen processing in granuloma lesions. In addition, we have only been able to address HLA-A2 and HLA-DR4 restricted presentation of defined T-cell epitopes; other MHC class I or class II alleles may be more effective in shaping a focused, MTB-specific T-cell response. Further studies, implementing a broader set of antigen peptides presented by different MHC alleles, are needed to ultimately address the existence of potential "immunodominant" T-cell responses. The immunological control of other recurring or chronic infections of the lung, such as CMV or other crucial MTB-associated target epitopes associated with non-replicating persistent bacilli may likely require the presence of adequately expanded T-cells as well.

These data carry implications for vaccine design as well as for the definition of novel surrogate markers associated with immune protection. Given the observations that each organ may be equipped with a different immune response to the same pathogen in terms of quality or quantity, the understanding of the immunological situation in the lung in human TB is fundamental for MTB vaccine design. Vaccine efficacy may be strongly enhanced by including the ESAT-6 Ag, as the ESAT-6$_{1-20}$ peptide-specific CD4+ lymphocytes were among the main performers as defined by IFN-γ production.

ESAT-6 may certainly be a crucial antigen in the immune response to MTB and studies advocate or have already successfully implemented this antigen in vaccination in a murine model. Data on the immunodominant epitope(s) (potentially important for both efficacy and applicability) are differing, though. Our experiments included the peptides ESAT-6$_{1-20}$ and ESAT-6$_{72-95}$, covering the aminoterminal (N-terminal) and the carboxyterminal (C-terminal) part of the antigen and had been performed on GALs of Caucasian patients. The data in the current report indicate that the epitopes reside in the N-terminal part of ESAT-6 and are preferentially recognized. They can be presented on various HLA DR-molecules in accord with a study on PBL by Ulrichs et al. involving German patients as well as with a report of the same group on recent PPD converters from Boston, Mass. On the other hand, studies from other regions of the world advocate other ESAT-6 epitopes: T-cells from Ethiopian patients preferentially recognized the central part of the antigen, while Kuwaiti and Danish patients had most frequently recognized the C-terminal region (aa 72-95). As discussed by both Mustafa et al. and Ravn et al., this phenomenon may result from diversities in the genetic HLA-makeup of different ethnic groups. Similar observations have been made in regard to the ESAT-6 recall responses of genetically different mice.

Substantial evidence exists for the critical role of CD8+ lymphocytes in tuberculosis. We have also observed clonal expansions of MTB-specific CB8+ GALs in lung tissue, as for example, the TCR VB3 positive T-cell clone that constituted 17% of the CD8+ GAL population in patient #1. Our goal was then to determine the major antigenic targets of CD8+ GALs by screening a panel of HLA-A2-presented peptides derived from the secreted Ags 85a, 85b, ESAT-6 and the 19-kDa lipoprotein that had been reported as MTB-associated targets. We observed a preferential recognition of Ag85a$_{242-250}$ and Ag85b$_{199-207}$ as well as ESAT-6$_{28-36}$ and a moderate reaction to 19-kDaAg$_{88-97}$, while Ag85a$_{48-56}$ and Ag85b$_{143-152}$ elicited little response, if any at all. Whether this observation is a general trend for lung-derived CD8+ T cells or a distinct feature for the individual patient may need to be further studied in a larger cohort. The major importance of these data is, however, that Ag85a- and Ag85b-specific as well as ESAT-6- and 19-kDaAg-specific CD8+ T-cells are indeed present in the lung (as defined by IFN-γ production upon antigenic stimulation) and not only in peripheral blood and that they are presumably involved in the maintenance of latency. In attempting to visualize these cells ex vivo we performed in situ tetramer staining followed by CLSM and, thereby, achieved an unprecedented exposition of both Ag85b- and 19 kDaAg-specific CD8+ T cells in human lung tissue without the bias of in vitro culture of T-cells. TCR analysis in HLA-A2/Ag85b or HLA-DR4/ESAT-6-sorted GAL from single patients also suggests a restricted TCR usage (FIG. 21)

In summary, we demonstrate that in human latent TB CD4+ and CD8+ MTB-reactive lymphocytes are present, highly expanded and functional in the lung tissue. CDR3 spectratyping coupled with flow cytometrical TCR VB analysis is a powerful tool in their identification and has enabled us to understand that a focused lymphocyte population, distinct from PBL, does govern latency. Key targets are peptides of MTB secreted antigens like ESAT-6 and MTB Ag85a/85b. Integration of these antigens into a vaccine should be important for protective immunity to MTB.

Although the invention has been described with reference to the above examples, it will be understood that modifications and variations are encompassed within the spirit and scope of the invention. Accordingly, the invention is limited only by the following claims.

We claim:

1. An HLA-DR4 tetramer complex wherein the complex comprises an isolated HLA-DR4 restricted epitope consisting of the amino acid sequence of SEQ ID NO: 8 or an isolated conservative variant thereof having the specific binding ability of said SEQ ID NO: 8, bound specifically to isolated HLA-DR4 monomers or isolated modified HLA-DR4 monomers having the functional ability to bind specifically to said epitope.

2. The complex of claim 1, wherein said monomers are tagged with a moiety.

3. The complex of claim 2, wherein said moiety is selected from the group consisting of biotin, FLAG peptide, glutathione, divalent metal ion and polyhistidine peptide.

4. The complex of claim 3, wherein said moiety is biotin.

5. The complex of claim 3, wherein said moiety is bound to a specific binding pair.

6. The complex of claim 5, wherein said specific binding pair is selected from the group consisting of streptavidin, anti-FLAG antibody, glutathione S-transferase (GST), Ni-iminodiacetic acid (Ni-IDA), Ni-nitriloacetic acid (Ni-NTA), 1,2-dioleoyl-sn-glycero-3-[N-(5 amino-1-carboxypentyl)-iminodiacetic acid]-succinyl with covalently attached N",N"-bis[carboxymethyl]-L-lysine (nitriloacetic acid) (DOGS-Ni-NTA).

7. The complex of claim 1, wherein said HLA-DR4 monomers or said modified HLA-DR4 monomers are obtained by expression on a yeast cell or a hybridoma.

* * * * *